US009701685B2

(12) United States Patent
Chen et al.

(10) Patent No.: US 9,701,685 B2
(45) Date of Patent: Jul. 11, 2017

(54) SPIROPYRROLIDINES AS MDM2 INHIBITORS

(71) Applicant: HUDSON BIOPHARMA INC., North Brunswick, NJ (US)

(72) Inventors: Yi Chen, Nutley, NJ (US); Qingjie (Jack) Ding, Bridgewater, NJ (US); Yang-sheng Sun, North Brunswick, NJ (US)

(73) Assignee: Hudson Biopharma Inc., North Brunswick, NJ (US)

( * ) Notice: Subject to any disclaimer, the term of this patent is extended or adjusted under 35 U.S.C. 154(b) by 0 days.

(21) Appl. No.: 14/751,671

(22) Filed: Jun. 26, 2015

(65) Prior Publication Data

US 2015/0322076 A1    Nov. 12, 2015

Related U.S. Application Data

(60) Provisional application No. 62/038,548, filed on Aug. 18, 2014.

(51) Int. Cl.
 *C07D 487/10* (2006.01)
(52) U.S. Cl.
 CPC .................... *C07D 487/10* (2013.01)
(58) Field of Classification Search
 CPC .................................................. C07D 487/10
 See application file for complete search history.

(56) References Cited

U.S. PATENT DOCUMENTS

| | | | |
|---|---|---|---|
| 7,759,383 | B2 | 7/2010 | Wang et al. |
| 8,088,815 | B2 | 1/2012 | Bartkovitz et al. |
| 8,088,931 | B2 | 1/2012 | Wang et al. |
| 8,217,044 | B2 | 7/2012 | Chu et al. |
| 8,629,133 | B2 | 1/2014 | Sugimoto et al. |
| 8,629,141 | B2 | 1/2014 | Wang et al. |
| 8,680,132 | B2 | 3/2014 | Wang et al. |
| 8,742,121 | B2 | 6/2014 | Wang et al. |
| 2011/0130398 | A1 | 6/2011 | Bartkovitz et al. |
| 2012/0046306 | A1 | 2/2012 | Bartkovitz et al. |
| 2012/0071499 | A1 | 3/2012 | Chu et al. |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.org/wiki/Cancer.*
Zhang, et al.,"Discovery of Potent and Selective Spiroindolinone MDM2 Inhibitor, RO8994, for Cancer Therapy", Bioorganic & Medicinal Chemistry, Jun. 11, 2014, vol. 22, No. 15, pp. 4001-4009.
Shu, et al., "Synthesis of a Spiroindolinone Pyrrolidinecarboxamide MDM2 Antagonist", Organic Process Research & Development, 2013, vol. 27, No. 2, pp. 247-256.
Aguilar, et al., "Design of Chemically Stable, Potent, and Efficacious MDM2 Inhibitors that Exploit the Retro-Mannich Ring-Opening-Cyclization Reaction of Mechanism in Spiro-oxindoles", Journal of Medicinal Chemistry, Dec. 12, 2014, vol. 57, No. 24, pp. 10486-10498.
International Search Report and Written Opinion mailed Feb. 29, 2016 for Application No. PCT/US2015/037974, 16 pages.
Ding et al., "Structure-Based Design of Spiro-Oxindoles as Potent, Specific Small-Molecule Inhibitors of the MDM2-p53 Interaction", Journal of Medicinal Chemistry, vol. 49, Issue 12, pp. 3432-3435, 2006.
Antonchick et al., "Highly Enantioselective Synthesis and Cellular Evaluation of Spirooxindoles Inspired by Natural Products", Nature Chemistry, vol. 2, pp. 735-740, Sep. 2010.
Voituriez et al., "AnOrganocatalytic [3+2] Cyclisation Strategy for the HighlyEnantioselective Synthesis of Spirooxindoles", Chem. Eur. J., vol. 16, Issue 42, pp. 12541-12544, Nov. 8, 2010.
Awata et al., "Catalytic Asymmetric exo'-Selective [3+2] Cycloaddition for Constructing Stereochemically Diversified Spiro[pyrrolidin-3,3'-oxindole]s", Chem. Eur. J., vol. 18, Issue 27, pp. 8278-8282, Jul. 2, 2012.
Ding et al., "Discovery of RG7388, a Potent and Selective p53-MDM2 Inhibitor in Clinical Development", Journal of Medicinal Chemistry, vol. 56, Issue 14, pp. 5979-5983, Jul. 16, 2013.
Zhang et al., "Discovery of Potent and Orally Active p53-MDM2 Inhibitors RO5353 and RO2468 for Potential Clinical Development", ACS Medicinal Chemistry Letter, vol. 5, Issue 2, pp. 124-127, Dec. 29, 2013.
Narayan et al., "Catalytic Enantioselective 1,3-Dipolar Cycloadditions of Azomethine Ylides for Biology-Oriented Synthesis", Acc. Chem. Res, vol. 47, Issue 4, pp. 1296-1310, Mar. 22, 2014.

* cited by examiner

*Primary Examiner* — Shawquia Jackson
(74) *Attorney, Agent, or Firm* — Moser Taboada

(57) ABSTRACT

Described are spiropyrrolidines (I) useful as inhibitors of MDM2/p53 interactions and provides useful agents for the treatment of diseases like cancer and retinal macular degeneration diseases. The invented compounds herein have the general Further described are pharmaceutical compositions that comprise one or more compounds of the invention, a pharmaceutically acceptable salt or pro-drug and/or a pharmaceutically acceptable carrier or excipient.

20 Claims, No Drawings

SPIROPYRROLIDINES AS MDM2 INHIBITORS

This application claims the priority of U.S. Prov. Application No. 62/038,548, filed Aug. 18, 2014, the contents of which are incorporated herein in their entirety.

The present invention relates to spiropyrrolidine compounds useful in treating diseases linked to the malfunction of p53 signal pathway such as cancer.

MDM2 is a negative regulatory protein of tumor suppressor protein p53. p53 regulates cell cycle growth, apoptosis, senescence and functions as the guardian of the cellular genomic integrity in response to various cellular stresses including DNA damage, hypoxia and oncogene activation. It acts as one of the most important defense against the development of cancer. At molecular level, MDM2 and P53 forms an auto-regulatory feedback control loop and MDM2 negatively regulates the functions of p53 through 1) direct binding to p53 and inhibits its ability to trans-activate p53 regulated genes; 2) mediating the ubiquitin dependent degradation of p53; 3) export of p53 out of the nucleus. p53 can induce the expression of MDM2 gene and hence the MDM2 protein in cells. This feedback loop control insures in normal cells that MDM2 and p53 stay at a suitable low level.

In about 50% of cancer cases, however, p53 is either mutated or deleted which result in the failure of the auto-regulatory mechanism. In the other 50% of cancer cases where p53 maintains its wild type form, the ratio of MDM2 to p53 is dyregulated and MDM2 protein is over expressed. In the latter case, an inhibitor of MDM2 should stimulate the accumulation of p53 and lead to cell cycle arrest and/or apoptosis and may provide a useful tool for cancer therapy. Literature has also indicated that MDM2 binds E2F through a conserved binding region as p53 and activates the E2F dependent transcription of cyclin A (Martin K., *Nature*, 1995, 375, 691-694; Strachan, G. D. et al, *Journal of biological Chemistry*, 2001, 456, 45677-45685), suggesting that MDM2 inhibitors might also have the prospects to treat p53 mutated cells.

SUMMARY OF INVENTION

This invention describes the discovery of spiropyrrolidines (I) as inhibitors of MDM2/p53 interactions and provides useful agents for the treatment of diseases linked to the malfunction of p53 signal pathway including cancer and age related retinal macular degeneration. The invented compounds herein have the general

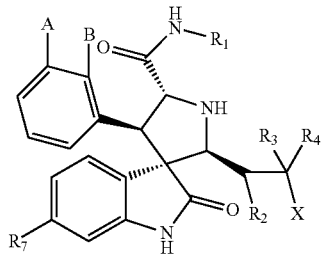

formula of I where $R_1$, $R_2$, $R_3$, $R_4$, $R_7$, A, B and X are defined in the following. The current invention also relates to pharmaceutical compositions that comprise one or more compounds of the invention, a pharmaceutically acceptable salt or pro-drug and a pharmaceutically acceptable carrier or excipient.

The present invention further relates to a method for the treatment of cancer, in particular the treatment of leukemia, solid tumors and age related retinal macular degeneration disorders.

DESCRIPTION OF THE INVENTION

The present invention describes the discovery of spiropyrrolidine derivatives of general structural formula I which are MDM2 inhibitors and are useful as anticancer agents and can also be used for the treatment of age related retinal macular degeneration disorders as well as other diseases linked to the malfunction of p53 signal pathway.

The claimed compounds are of general structural formula I

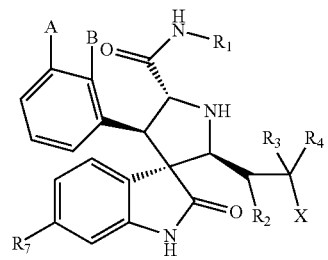

wherein A are halogens and are independently selected from Cl and F and B are independently selected from Cl, H and F; $R_1$ is aryl, substituted aryl, heteroaryl and substituted heteroaryl; $R_2$ is hydrogen or it is a carbon-carbon bond with either X, $R_3$ or $R_4$; $R_3$ and $R_4$ are independently selected from H, lower alkyl and substituted lower alkyls, cycloalkyls, substituted cycloalkyls, alkenyls, substituted alkenyls, alkyns, substituted alkyns, or they together can form a 3, 4, or 5 membered ring or one of them can form a C—C bond with $R_2$; X is independently selected from F, CN, and

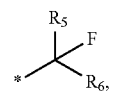

where $R_5$ and $R_6$ are independently selected from hydrogen and F; and $R_7$ is halogen and is selected independently from Cl, Br and F.

Where $R_3$ and $R_4$ form a ring, it can be, in embodiments applicable to all formulas I-IV, a carbocyclic ring.

Where one of $R_3$ and $R_4$ link back to via a bond that is $R_2$, the result can be, in embodiments applicable to all formulas I-IV, a carbocyclic ring, such as a 3-5 membered ring.

Selected examples of $R_1$ include but not limited to the following

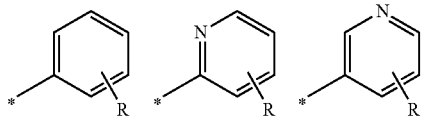

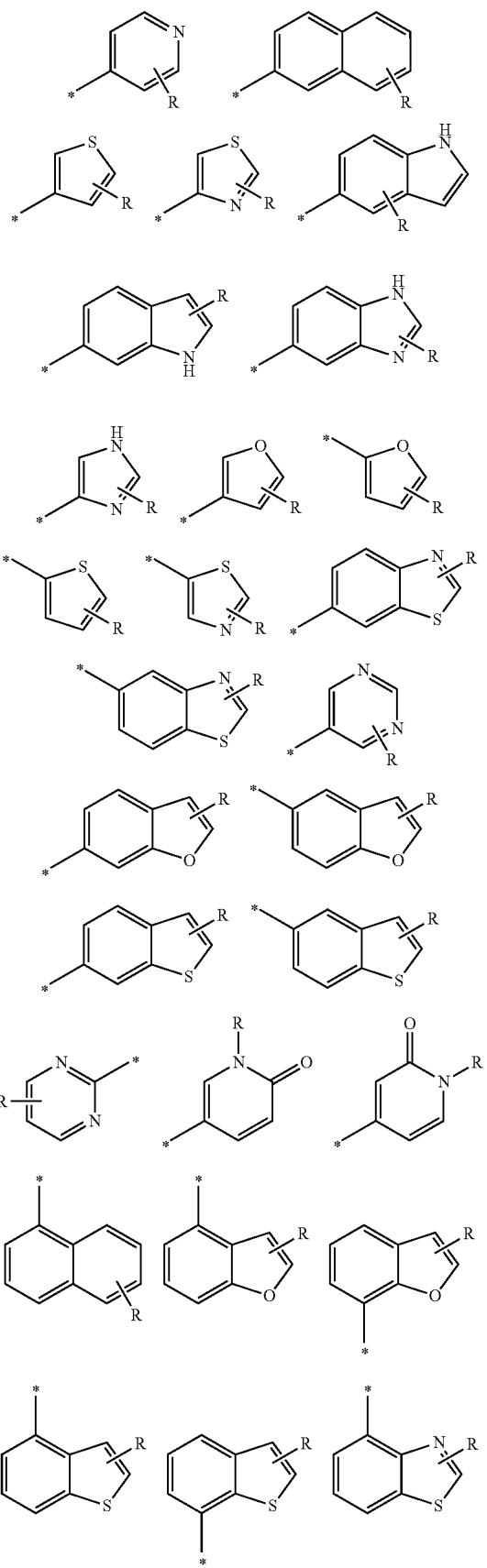

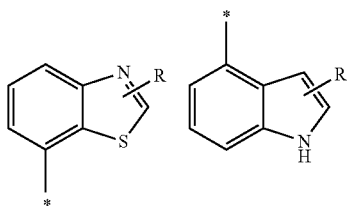

Where R is independently selected from groups of halogen, hydroxyl, hydrogen, lower alkyl, substituted lower alkyl, cycloalkyl, substituted cycloalkyl, lower alkoxy, substituted lower alkoxy, cyano, amino, substituted amino, sulfonylamino, substituted sulfonylamino, aminosulfonyl, substituted aminosulfonyl, hydroxycarbonyl, lower alkoxycarbonyl, aminocarbonyl, substituted aminocarbonyl, carbonylamino, substituted carbonylamino, amidino, substituted amidino, guanidino, substituted guanidino, tetrazoles, substituted tetrazoles and can independently substitute any single position or multiple positions of the aryl/heteroaryl ring and preferably not to exceed three positions; Or when the substitution occurs at two adjacent positions, it can form a five or six membered hetero ring;

Notable useful compounds within formula I are compounds of formula II

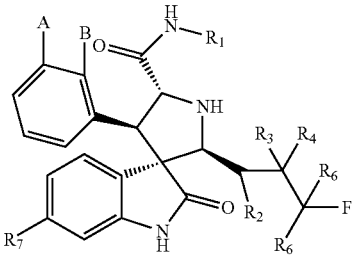

wherein A, B, $R_1$, $R_2$, $R_3$, $R_4$ and $R_7$ are as described above; and $R_5$ and $R_6$ are independently selected from hydrogen and F.

Notable useful compounds within formula I are compounds of formula III:

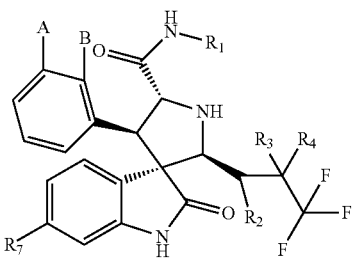

wherein A, B, $R_1$, $R_2$, $R_3$, $R_4$ and $R_7$ are as described above.

In embodiments applicable to all formulas I-IV, $R_1$ is

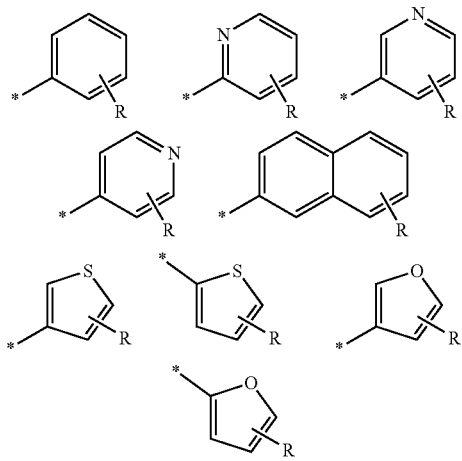

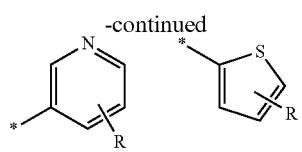

In embodiments applicable to all formulas I-IV, R is independently selected from groups of halogen, hydroxyl, hydrogen, lower alkyl, substituted lower alkyl, cycloalkyl, substituted cycloalkyl, lower alkoxy, substituted lower alkoxy, cyano, amino, substituted amino, sulfonylamino, substituted sulfonylamino, aminosulfonyl, substituted aminosulfonyl, hydroxycarbonyl, lower alkoxycarbonyl, aminocarbonyl, substituted aminocarbonyl, carbonylamino, substituted carbonylamino, amidino, substituted amidino, guanidino, substituted guanidino, tetrazoles, substituted tetrazoles and can independently substitute any single position or multiple positions of the aryl/heteroaryl ring and preferably not to exceed three positions; Or when the substitution occurs at two adjacent positions, it can form a five or six membered hetero ring;

Further notable useful compounds highly analogous to those within formula I are compounds of formula IV

IV

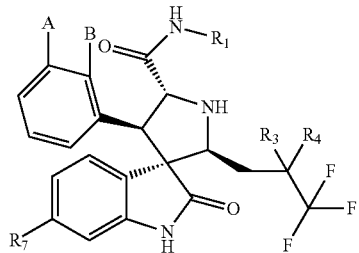

wherein $R_1$ and $R_7$ are as described above; A is independently selected from Cl, F, and Br; B is selected from F, H; and $R_3$ and $R_4$ are independently selected from H, and methyl.

In embodiments applicable to all formulas I-IV, $R_1$ is

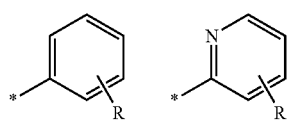

-continued

In embodiments applicable to all formulas I-IV, R is independently selected from groups of halogen, hydroxyl, hydrogen, lower alkyl, substituted lower alkyl, cycloalkyl, substituted cycloalkyl, lower alkoxy, substituted lower alkoxy, cyano, amino, substituted amino, sulfonylamino, substituted sulfonylamino, aminosulfonyl, substituted aminosulfonyl, hydroxycarbonyl, lower alkoxycarbonyl, aminocarbonyl, substituted aminocarbonyl, carbonylamino, substituted carbonylamino, amidino, substituted amidino, guanidino, substituted guanidino, tetrazoles, substituted tetrazoles and can independently substitute any single position or multiple positions of the aryl/heteroaryl ring and preferably not to exceed three positions; Or when the substitution occurs at two adjacent positions, it can form a five or six membered hetero ring.

Notable useful are compounds of Group II-A of formula II, in which: $R_2$ is hydrogen; and $R_5$ and $R_6$ are both H.

Further notable compounds of Group II-B of formula II, in which: $R_2$ is hydrogen; $R_3$ and $R_4$ are both methyl; and $R_5$ and $R_6$ are both H.

In embodiments applicable to all formulas I-IV, R is independently selected from groups of halogen, hydroxyl, hydrogen, lower alkyl, substituted lower alkyl, cycloalkyl, substituted cycloalkyl, lower alkoxy, substituted lower alkoxy, cyano, amino, substituted amino, sulfonylamino, substituted sulfonylamino, aminosulfonyl, substituted aminosulfonyl, hydroxycarbonyl, lower alkoxycarbonyl, aminocarbonyl, substituted aminocarbonyl, carbonylamino, substituted carbonylamino, amidino, substituted amidino, guanidino, substituted guanidino, tetrazoles, substituted tetrazoles and can independently substitute any single position or multiple positions of the aryl/heteroaryl ring and preferably not to exceed three positions; Or when the substitution occurs at two adjacent positions, it can form a five or six membered hetero ring.

Further notable compounds of Group II-C of formula II, in which: $R_2$ is H; $R_3$ and $R_4$ together form a 3, 4, or 5 membered aliphatic ring, such as a cyclopropyl ring; and $R_5$ and $R_6$ are both H.

Further notable compounds of Group I-A of formula I, in which: $R_2$ is H; $R_3$ and $R_4$ are both methyl; and X is CN.

Further notable compounds of Group I-B of formula I, in which: $R_2$ forms a C—C bond with X; and $R_3$ and $R_4$ are independently selected from methyl, lower alkyl, substituted lower alkyl, alkenyl and substituted lower alkenyl, or they together can form a 3, 4, or 5 membered aliphatic ring.

Further notable compounds include listed below. The claims below, unless specifically designated otherwise, cover a racemic mixture and cover the isomer designated above and compositions including a racemate that includes the above-designated isomer. The designation "racemic" in the listing below emphasizes that a racemate of that particular compound is subject matter which may be claimed. The designation "chiral" emphasizes a single enantiomer that can be synthesized either by asymmetric synthesis or alternatively by separation of a racemate by chiral technology (such as chiral HPLC, or chiral supercritical fluid chromatography) or by resolution of a racemate by common chemistry method. The compounds are:

Racemic ethyl 4-[[(2'R,3R,3'S,5'S)-6-chloro-3'-(3-chloro-2-fluoro-phenyl)-5'-(2-methylprop-1-enyl)-2-oxo-spiro[indoline-3,4'-pyrrolidine]-2'-carbonyl]amino]-3-methoxy-benzoate Racemic 4-[[(2'R,3R,3'S,5'S)-6-chloro-3'-(3-chloro-2-fluoro-phenyl)-5'-(2-methylprop-1-enyl)-2-oxo-spiro[indoline-3,4'-pyrrolidine]-2'-carbonyl]amino]-3-methoxy-benzoic acid Racemic (2'R,3R,3'S,5'S)-N-(4-carbamoyl-2-methoxy-phenyl)-6-chloro-3'-(3-chloro-2-fluoro-phenyl)-5'-(2-methylprop-1-enyl)-2-oxo-spiro[indoline-3,4'-pyrrolidine]-2'-carboxamide Racemic ethyl 4-[[(2'R,3R,3'S,5'S)-6-chloro-3'-(3-chloro-2-fluoro-phenyl)-2-oxo-5'-[(2R)-3,3,3-trifluoro-2-methyl-propyl]spiro[indoline-3,4'-pyrrolidine]-2'-carbonyl]amino]-3-methoxy-benzoate Racemic 4-[[(2'R,3R,3'S,5'S)-6-chloro-3'-(3-chloro-2-fluoro-phenyl)-2-oxo-5'-[(2S)-3,3,3-trifluoro-2-methyl-propyl]spiro[indoline-3,4'-pyrrolidine]-2'-carbonyl]amino]-3-methoxy-benzoic acid Racemic 4-[[(2'R,3R,3'S,5'S)-6-chloro-3'-(3-chloro-2-fluoro-phenyl)-2-oxo-5'-[(2R)-3,3,3-trifluoro-2-methyl-propyl]spiro[indoline-3,4'-pyrrolidine]-2'-carbonyl]amino]-3-methoxy-benzoic acid Racemic (2'R,3R,3'S,5'S)-N-(4-carbamoyl-2-methoxy-phenyl)-6-chloro-3'-(3-chloro-2-fluoro-phenyl)-2-oxo-5'-[(2S)-3,3,3-trifluoro-2-methyl-propyl]spiro[indoline-3,4'-pyrrolidine]-2'-carboxamide Racemic (2'R,3R,3'S,5'S)-N-(4-carbamoyl-2-methoxy-phenyl)-6-chloro-3'-(3-chloro-2-fluoro-phenyl)-2-oxo-5'-[(2R)-3,3,3-trifluoro-2-methyl-propyl]spiro[indoline-3,4'-pyrrolidine]-2'-carboxamide Racemic (4-ethoxycarbonyl-2-methoxy-phenyl) (2'R,3R,3'S,5'S)-6-chloro-3'-(3-chloro-2-fluoro-phenyl)-5'-(3-fluoro-2,2-dimethyl-propyl)-2-oxo-spiro[indoline-3,4'-pyrrolidine]-2'-carboxamide Racemic 4-[(2'R,3R,3'S,5'S)-6-chloro-3'-(3-chloro-2-fluoro-phenyl)-5'-(3-fluoro-2,2-dimethyl-propyl)-2-oxo-spiro[indoline-3,4'-pyrrolidine]-2'-carbonyl]amino-3-methoxy-benzoic acid Racemic (4-carbamoyl-2-methoxy-phenyl) (2'R,3R,3'S,5'S)-6-chloro-3'-(3-chloro-2-fluoro-phenyl)-5'-(3-fluoro-2,2-dimethyl-propyl)-2-oxo-spiro[indoline-3,4'-pyrrolidine]-2'-carboxamide Chiral 4-[(2'R,3R,3'S,5'S)-6-chloro-3'-(3-chloro-2-fluoro-phenyl)-5'-(3-fluoro-2,2-dimethyl-propyl)-2-oxo-spiro[indoline-3,4'-pyrrolidine]-2'-carbonyl]amino-3-methoxy-benzoic acid Chiral (4-carbamoyl-2-methoxy-phenyl) (2'R,3R,3'S,5'S)-6-chloro-3'-(3-chloro-2-fluoro-phenyl)-5'-(3-fluoro-2,2-dimethyl-propyl)-2-oxo-spiro[indoline-3,4'-pyrrolidine]-2'-carboxamide Chiral ethyl-4-[[(2'R,3'R,3'S,5'S)-6-chloro-3'(3-chloro-2-fluoro-phenyl)-2-oxo-5'-[(2R)-3,3,3-trifluoro-2-methyl-propyl]spiro[indoline-2,4'-pyrrolidine]-2'-carbonyl]amino]-3-methoxy-benzoate Chiral 4-[[(2'R,3R,3'S,5'S)-6-chloro-3'-(3-chloro-2-fluoro-phenyl)-2-oxo-5'-[(2R)-3,3,3-trifluoro-2-methyl-propyl]spiro[indoline-3,4'-pyrrolidine]-2'-carbonyl]amino]-3-methoxy-benzoic acid Chiral (2'R,3R,3'S,5'S)-N-(4-carbamoyl-2-methoxy-phenyl)-6-chloro-3'-(3-chloro-2-fluoro-phenyl)-2-oxo-5'-[(2R)-3,3,3-trifluoro-2-methyl-propyl]spiro[indoline-3,4'-pyrrolidine]-2'-carboxamide Racemic tert-butyl (2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carboxylate Racemic (2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carboxylic acid Racemic methyl 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]benzoate Racemic 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]benzoic acid Racemic (2'R,3R,3'S,5'S)-N-(4-carbamoylphenyl)-6-chloro-3'-(3-chloro-2-fluoro-phenyl)-5'-(2-cyano-2-methyl-propyl)-2-oxo-spiro[indoline-3,4'-pyrrolidine]-2'-carboxamide Racemic (2'R,3R,3'S,5'S)-6-chloro-3'-(3-chloro-2-fluoro-phenyl)-5'-(2-cyano-2-methyl-propyl)-N-[4-(2-hydroxy-ethoxy)phenyl]-2-oxo-spiro[indoline-3,4'-pyrrolidine]-2'-carboxamide Racemic methyl 5-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]thiophene-2-carboxylate Racemic 5-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]thiophene-2-carboxylic acid Racemic (2'R,3R,3'S,5'S)-N-(5-carbamoyl-2-thienyl)-6-chloro-3'-(3-chloro-2-fluoro-phenyl)-5'-(2-cyano-2-methyl-propyl)-2-oxo-spiro[indoline-3,4'-pyrrolidine]-2'-carboxamide Racemic methyl 5-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]pyridine-2-carboxylate Racemic 5-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]pyridine-2-carboxylic acid Racemic methyl 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]-3-methoxy-benzoate Racemic 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]-3-methoxy-benzoic acid Racemic (2'R,3R,3'S,5'S)-N-(4-carbamoyl-2-methoxy-phenyl)-6-chloro-3'-(3-chloro-2-fluoro-phenyl)-5'-(2-cyano-2-methyl-propyl)-2-oxo-spiro[indoline-3,4'-pyrrolidine]-2'-carboxamide Chiral 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]-3-methoxy-benzoic acid Racemic methyl 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]-3-fluoro-benzoate Racemic 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]-3-fluoro-benzoic acid Racemic methyl 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]-3-fluoro-benzoate Racemic 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]-3-chloro-benzoic acid Racemic methyl-4-[[(2'R,3'R,3'S,5'S)-6-chloro-3'(3-chloro-2-fluoro-phenyl)-2-oxo-5'-(3,3,3-trifluoro-2,2-dimethyl-propyl)spiro[indoline-3,4'-pyrrolidine]-2'-carbonyl]amino]-3-methoxy-benzoate Racemic 4-[[(2'R,3R,3'S,5'S)-6-chloro-3'-(3-chloro-2-fluoro-phenyl)-2-oxo-5'-[(3,3,3-trifluoro-2,2-dimethyl-propyl)spiro[indoline-3,4'-pyrrolidine]-2'-carbonyl]amino]-3-methoxy-benzoic acid Racemic (2'R,3R,3'S,5'S)-N-(4-carbamoyl-2-methoxy-phenyl)-6-chloro-3'-(3-chloro-2-fluoro-phenyl)-2-oxo-5'-(3,3,3-trifluoro-2,2-dimethyl-propyl)spiro[indoline-3,4'-pyrrolidine]-2'-carboxamide Chiral methyl-4-[[(2'R,3'R,3'S,5'S)-6-chloro-3'(3-chloro-2-fluoro-phenyl)-2-oxo-5'-[(2S)-3,3,3-trifluoro-2-methyl-propyl]spiro[indoline-2,4'-pyrrolidine]-2'-carbonyl]amino]-3-methoxy-benzoate Chiral 4-[[(2'R,3R,3'S,5'S)-6-chloro-3'-(3-chloro-2-fluoro-phenyl)-2-oxo-5'-[(2S)-3,3,3-trifluoro-2-methyl-propyl]spiro[indoline-3,4'-pyrrolidine]-2'-carbonyl]amino]-3-methoxy-benzoic acid Chiral (2'R,3R,3'S,5'S)-N-(4-carbamoyl-2-methoxy-phenyl)-6-chloro-3'-(3-chloro-2-fluoro-phenyl)-2-oxo-5'-[(2S)-3,3,3-trifluoro-2-methyl-propyl]spiro[indoline-3,4'-pyrrolidine]-2'-carboxamide Racemic 4-{[6-chloro-4'-(3-chloro-2-fluoro-phenyl)-2'-(1-fluoromethyl-cyclopropylmethyl)-2-oxo-1,2-dihydro-spiro[indole-3,3'-pyrrolidin]e-5'-carbonyl]-amino}-3-methoxy-benzoic acid methyl ester Racemic 4-{[6-chloro-4'-(3-chloro-2-fluoro-phenyl)-2'-(1-fluoromethyl-cyclopropyl methyl)-2-oxo-1,2-dihydro-spiro[indole-3,3'-pyrrolidin]e-5'-carbonyl]-amino}-3-methoxy-benzoic acid Racemic 6-chloro-4'-(3-chloro-2-fluoro-phenyl)-2'-(1-fluoromethyl-cyclopropyl methyl)-2-oxo-1,2-dihydro-spiro[indole-3,3'-pyrrolidine]-5'-carboxylic acid (4-carbamoyl-2-methoxy-phenyl)-amide Chiral 4-[[(2'R,3R,3'S,5'S)-6-chloro-3'-(3-chloro-2-fluoro-phenyl)-5'-[[1 (fluoromethyl)cyclopropyl]methyl]-2-oxo-spiro[indoline-3,4'-pyrrolidine]-2'-carbonyl]amino]-3-methoxy-benzoic acid Chiral (2'R,3R,3'S,5'S)-N-(4-carbamoyl-2-methoxy-phenyl)-6-chloro-3'-(3-chloro-2-fluoro-phenyl)-5'-[[1-(fluoromethyl)cyclopropyl]methyl]-2-oxo-spiro[indoline-3,4'-pyrrolidine]-2'-carboxamide The present invention is further extended to pharmaceutical compositions comprising of an effective amount of any one or more of the above claimed compounds, a pharmaceutically acceptable salt or pro-drug or a pharmaceutically acceptable carrier or excipient.

The current invention is also directed to a method for treating solid tumors, leukemia and retinal macular degeneration diseases by administering an effective amount of a compound of formula I, its salts or pro-drugs, to a patient.

TERMS AND DEFINITIONS USED IN THE INVENTION

Halogen means F, Cl, Br or I. Preferred halogens are F and Cl.

Lower alkyl means a linear chain or branched, substituted or unsubstituted, saturated aliphatic hydrocarbon having 1-6, preferably 1-4 carbon atoms. Typical lower alkyl groups include methyl, ethyl, propyl, isopropyl, butyl, isobutyl etc.

$IC_{50}$ means the concentration of a particular compound that inhibits 50% of a specific measured activity.

Cycloalkyl refers to a non-aromatic, partially or completely cyclic aliphatic hydrocarbon containing 3 to 7 atoms. Cyclopropyl, cyclobutyl, cyclopental and cyclohexyl are some of the examples.

Substituted means that the substitution can occur at one or more positions and, unless otherwise indicated, the substituents at each substitution site are independently selected from the specific options.

Pro-drug refers to a compound that may be converted under physiological conditions or by solvolysis to any of the compounds of formula I. A pro-drug may be inactive when administered but is converted to an active compound of formula I in vivo.

Pharmaceutically acceptable means pharmacologically acceptable to a subject to which a particular compound is administered.

Pharmaceutically acceptable salt means an acid-addition salts or base-addition salts which retain the biological effectiveness and properties of the compounds of formula I. Typical acid-addition salts include those that are derived from inorganic acids such as hydrochloric acid, hydrobromic acid, sulfuric acid, phosphoric acid and nitric acid and those that are derived from organic acids like formic acid, methane sulfonic acid, oxalic acid, succinic acid, citric acid, malic acid, lactic acid, fumaric acid, p-toluene sulfonic acid, salicylic acid and so on. Samples of base derived salts include those derived from ammonium, sodium, potassium and so on.

Heteroaryl groups are aromatic groups having 5-10 atoms, one or two rings and contain one or more hetero atoms.

Hetero atoms refer to N, O, S, P.

Aryls refer to aromatic groups carrying 5-10 atoms and consisting of 1 or 2 rings. Examples of aryl groups include phenyl, naphthyl.

Alkenyl means a linear or branched, substituted or unsubstituted aliphatic unsaturated hydrocarbon carrying 2-6, preferably 2-4, carbon atoms and containing double bonds.

To treat indications with a therapeutic agent, an "effective amount" of a therapeutic agent will be recognized by clinicians but includes an amount effective to treat, reduce, alleviate, ameliorate, eliminate or prevent one or more symptoms of the condition sought to be treated, or alternately, the condition sought to be avoided, or to otherwise produce a clinically recognizable favorable change in the condition or its effects.

Synthesis of Compounds of Formula I

Generally, the compounds of the invention can be prepared according to the following schemes. The key intermediates 1, 2 and 5 could be prepared as described in scheme I and Scheme II. Condensation of amine with aldehyde gave desired imine 1 and 2. The amine can also be used in the salt form (HCl or trifluoroacetic acid salt). In those cases, a base like triethylamine was used to release the free amine.

Scheme I, synthesis of imines 1 and 2.

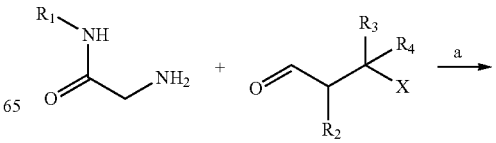

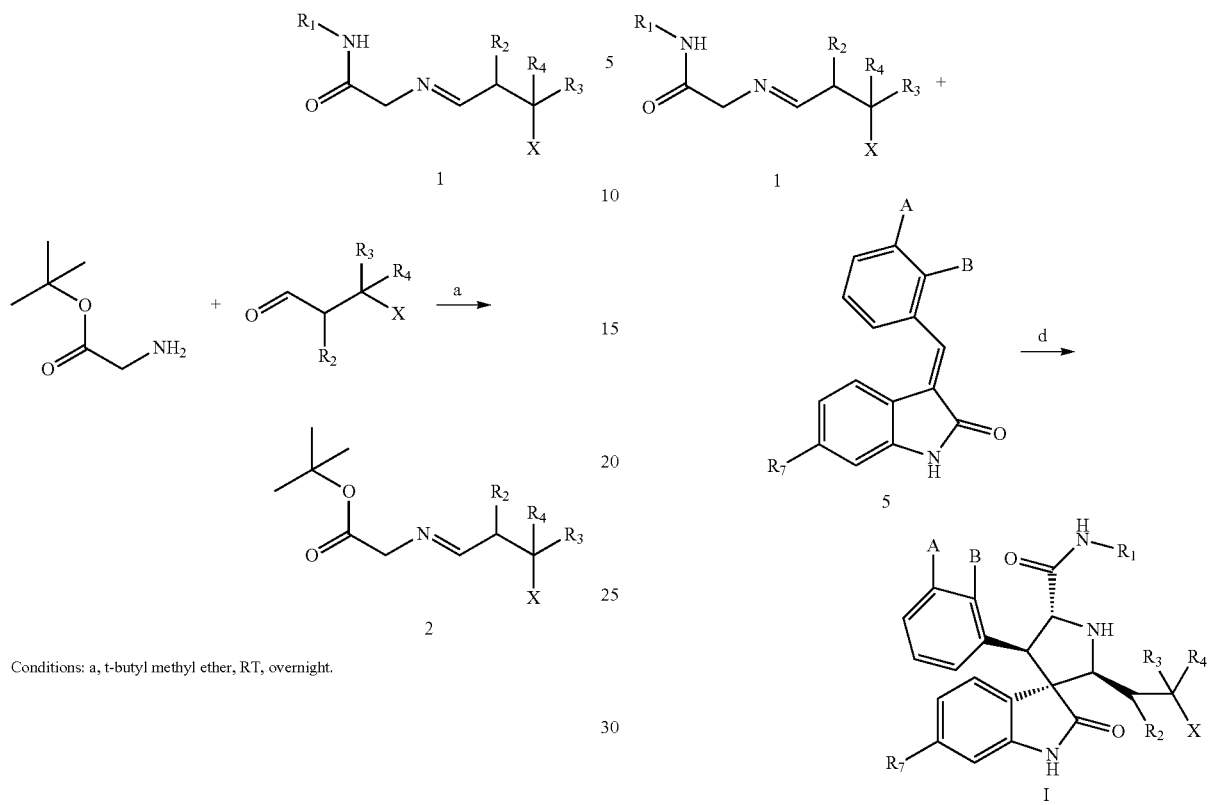

Conditions: a, t-butyl methyl ether, RT, overnight.

Conditions: d, DBU, Toluene, reflux.

Scheme II, synthesis of intermediate 5.

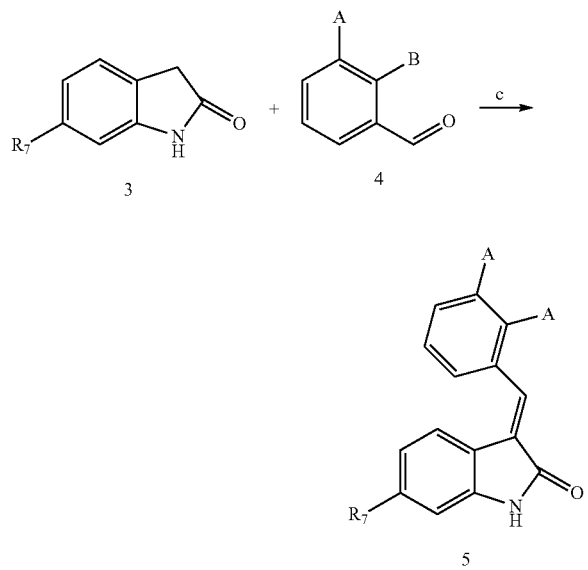

Conditions: c, Piperidine or soium methoxide, methanol, reflux

Intermediate 5 was prepared as described in Scheme II. Condensation of indolones 3 with aldehydes 4 was successfully conducted in methanol with the catalysis of a suitable base. It has been demonstrated that both piperidine and sodium methoxide were effective catalysts. Intermediate 5 was prepared in good yield with the catalysis of either piperidine or sodium methoxide (scheme II).

Compounds of formula I could be prepared according to Scheme III outlined above. Imines 1 and dipolarophiles 5 were condensed to form spiropyrrolidines I under the catalysis of DBU in toluene. The process might involve a first step 1,3 dipolar cycloaddtion followed by a base catalyzed isomerization (see, Shu et al, *Org. Process Res. Dev.* 2013, 17, 247-256). Other examples of publications describing the 1,3 dipolar cycloaddition of azomethine yilde with dipolarophiles could be found from Yuvaraj et al (*Tetrahedron lett.*, 2013, 54(8), 821-827), Stanley et al (*Chemical Review*, 2008, 108(8), 2887), Chen et al (*J. Am. Chem. Soc.* 2009, 131, 13819-13825), Shreiber et al (*J. Am. Chem. Soc.*, 2003, 125, 10174-10175), Antonchick et al (*Nature Chemistry*, 2010, 2, 735-740), Galliford et al (*Angew. Chem. Int. Ed.* (2007, 46, 8748-8758).

When chiral aldehydes were used, enantiomerically pure diasteromers of I can be obtained through general chemistry technique. Alternatively, racemic mixture of I could be separated by chiral HPLC, chiral superfluid HPLC or by common resolution methods such as the application of chiral base or chiral acid through crystallization. Desired isomers may also be prepared through asymmetric synthesis by employing chiral auxiliary, chiral ligand (for a reference, see Antonchick et al, *Nature Chemistry*, 2010, 2, 735-740).

Alternatively, compounds of formula I could then be prepared by the general procedure outline in scheme IV. Condensation of imine 2 with dipolarophiles 5 under the catalysis of LiOH in THF gave intermidiates 6, which was treated with acid to give carboxylic acid 7. Coupling of acid 7 with $R_1NH_2$ gave compounds of formula I.

Scheme IV, synthesis of formula I

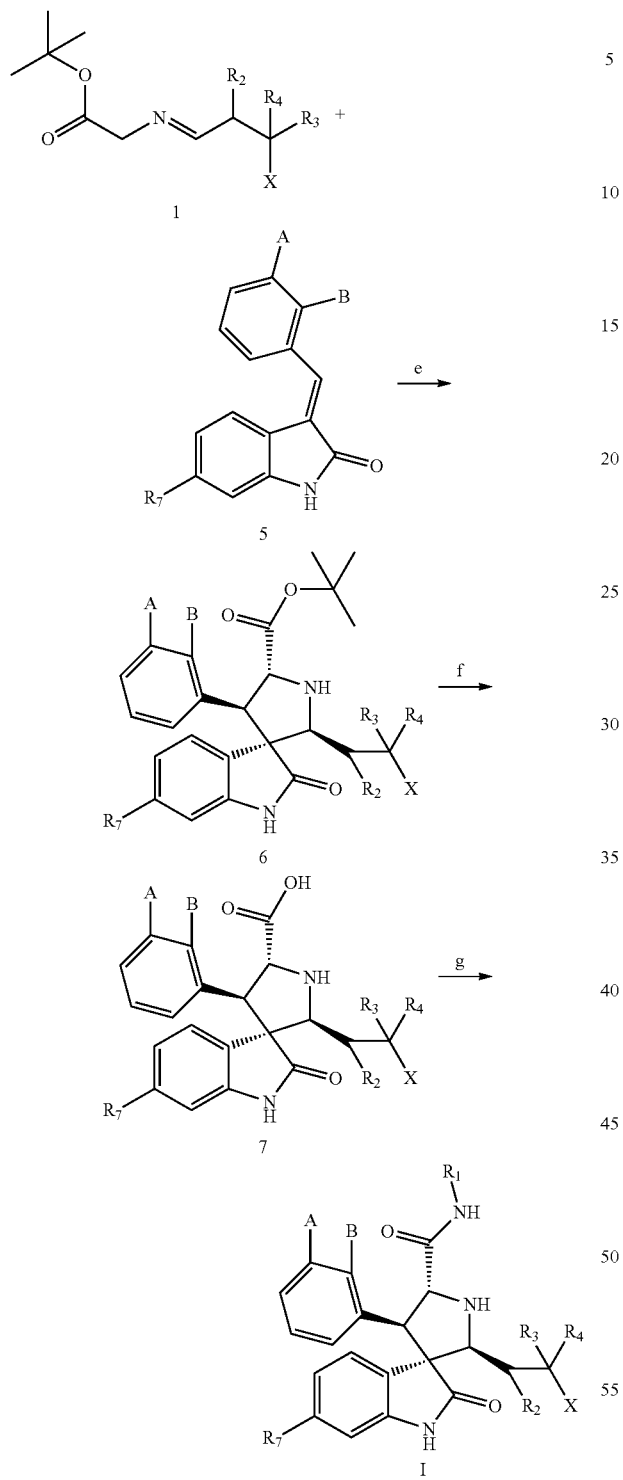

Conditions: e, LiOH, THF, Heat. f, CF$_3$COOH/DCM (30%), rt. g, HATU, DCM, R$_1$NH$_2$.
Methods of treating, Use for treating All of the compounds can be used, generally in an effective amount, to treat proliferative disorders such as cancer. An effective amount of one or more of the compounds in the art can be formulated and delivered to patients through oral, parenteral, patch, spray and other well-known art. The compounds discovered in the art can also be used together with other agents for combination therapy. Without being bound by theory, it is believed that the agents in the art can be particularly useful where the p53 protein is not mutated to a dysfunctional form and/or its signaling pathways still function. An effective amount here may vary from, without limitation, a dosage of 1 mg to 1500 mg/Kg per day for a patient with an average body weight of 70 Kg depending on any specific case. Formulation of a certain compound generally means the employment of some carriers, excipient and other material to make the dosage work more efficiently.

A subject for such treatment can be any animal subject to such proliferative disorders, such as humans.

EXAMPLES

Example 1

Preparation of (E)-tert-butyl 2-(3-cyano-3-methylbutylideneamino) acetate

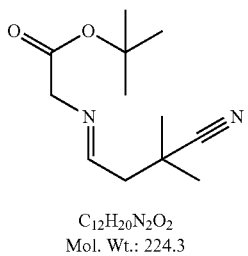 [SMILES: CC(C)(C#N)C/C=N/CC(=O)OC(C)(C)C]

C$_{12}$H$_{20}$N$_2$O$_2$
Mol. Wt.: 224.3

A mixture of glycine-tert-butyl ester (9.29 g, 0.708 mol) and 3,3-dimethyl-butyraldehyde (75 g, 0.674 mol) in DCM (1400 mL) was stirred at r.t. overnight. The reaction mixture was concentrated and the residue was dried in vacuo to give an oil (150 g, yield: 98.8%), which was used in the next step without further purification. $^1$HNMR (CDCl$_3$, 400 MHz): δ 7.77~7.79 (t, 1H), 4.15 (s, 2H), 2.56-2.57 (d, 2H), 1.46 (s, 9H), 1.44 (s, 6H).

Example 2

Preparation of methyl 4-[(2-aminoacetyl)amino]-3-methoxy-benzoate trifluoro acetic acid salt

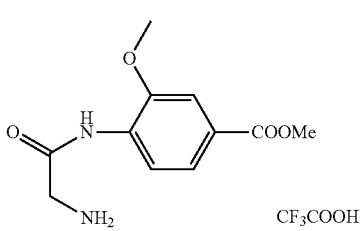

C$_{11}$H$_{14}$N$_2$O$_4$        C$_2$HF$_3$O$_4$
Mol. Wt.: 238.24        Mol. Wt.: 114.02

To a stirred solution of 2-(tert-butoxycarbonyl)acetic acid (Aldrich, 2.32 g, 13.3 mmol) in THF (12 mL), CDI (Aldrich, 2.15 g, 13.2 mmol) was added and the mixture was stirred at rt for 1 hr until the reaction went completion by TLC. Then methyl 4-amino-3-methoxybenzoate (Combi-blocks, 2.0 g, 11 mmol) was added and the mixture was stirred at 60° C. for 48 hrs. The reaction was quenched with water and diluted with EtOAc. The organic layer was separated, washed with saturated sodium bicarbonate solution and dried ($Na_2SO_4$). Removal of solvent gave an oil. The oil was dissolved in DCM (20 mL) and trifluoro acetic acid (8 mL) was added. The mixture was stirred at rt for 3 hrs until the reaction was complete. Removal of solvent under reduced pressure gave the TFA salt of the title compound. 3.94 g, 95%. $^1$HNMR ($CDCl_3$, 300 MHz): δ 10.06 (s, 1H), 8.37 (s, br, 3H), 8.25-8.28 (d, 1H, J=8.4 Hz), 7.57-7.64 (d, 1H, J=8.7 Hz), 7.59 (s, 1H), 3.96 (s, 3H), 3.94 (S, 2H), 3.88 (s, 3H), 1.33 (t, 3H, J=7.2 Hz).

Example 3

Preparation of ethyl 4-(2-aminoacetamido)-3-methoxybenzoate hydrochloride salt

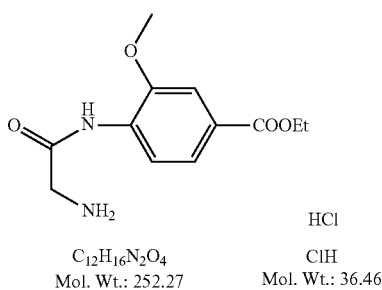 [SMILES: CCOC(=O)c1ccc(NC(=O)CN)c(OC)c1 ; Cl]

$C_{12}H_{16}N_2O_4$
Mol. Wt.: 252.27

HCl
ClH
Mol. Wt.: 36.46

To a stirred solution of ethyl 4-amino-3-methoxybenzoate (Ark Pharm, 20 g, 110.4 mmol) in THF (200 mL) at 0° C., triethylamine (Aldrich, 16.2 mL, 115.9 mmol) was added followed by 2-chloroacetyl chloride (Aldrich, 12.7 g, 112.7 mmol). The mixture was stirred at 0° C. for 1 hr until the reaction went completion by TLC (DCM). The salt was filtered out and the filtrate was concentrated to provide a solid (30 g). The solid was dissolved in NMP (260 mL) and ammonia (28%, 260 mL) was added at 0° C. The mixture was warmed to rt and stirred for 5 hrs until the reaction was complete. The excess ammonia was removed under reduced pressure and water was distilled out through azotropic distillation. The solid was filtered and dried to give a white crystal. 19 g, 63%. LC/MS MS (ES+) calculated for $C_{12}H_{16}N_2O_4$ (M+H)$^+$: 252.27, found, 252.21. $^1$HNMR ($CDCl_3$, 300 MHz): δ 10.03 (s, 1H), 8.31 (s, br, 3H), 8.23-8.26 (d, 1H, J=8.4 Hz), 7.57-7.64 (d, 1H, J=8.7 Hz), 7.57 (s, 1H), 4.29-4.36 (q, 2H, 7.2 Hz), 3.95 (s, 3H), 3.91 (s, 2H), 1.33 (t, 3H, J=7.2 Hz).

Example 4

Preparation of (E)-ethyl 3-methoxy-4-(2-(4,4,4-trifluoro-3-methylbutylideneamino)acetamido)benzoate

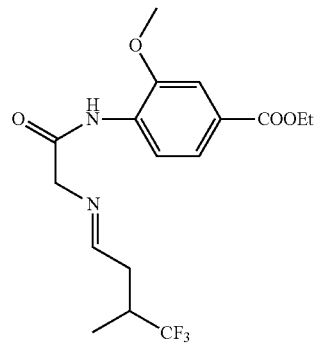

$C_{17}H_{21}F_3N_2O_4$
Mol. Wt.: 374.35

To a stirred suspension of ethyl 4-(2-aminoacetamido)-3-methoxybenzoate HCl salt (910.5 mg, 3.0 mmol) in MTBE (10 mL) was added triethylamine (363 mg, 3.6 mmol). The mixture was stirred for 30 min. at rt and 4,4,4-trifluoro-3-methylbutanal (Synquest, 420 mg, 3.0 mmol) was added. The new mixture was stirred at rt for 16 hrs. The solid was filtered and washed with MTBE. The filtrate was washed with brine and water and dried with sodium sulfate. Removal of solvent gave a pale yellow oil which solidifies upon standing. 1.10 g, 97.8%. $^1$HNMR ($CDCl_3$, 300 MHz): δ 9.53 (s, br, 1H), 8.50-8.6 (d, 1H, J=8.7 Hz), 7.89 (s, 1H), 7.50-7.75 (d, 1H, J=9.0 Hz), 7.59 (s, 1H), 4.38-4.41 (q, 2H, 7.2 Hz), 4.24 (s, 2H), 3.97 (s, 3H), 2.84-3.0 (m, 1H), 2.70-2.84 (m, 1H), 1.38-1.48 (t, 1H, J=7.2 Hz), 1.25-1.32 (d, 3H, J=6.9 Hz).

Example 5

Preparation of (E)-ethyl 3-methoxy-4-[2-(3-methyl-but-2-enylideneamino)acetamido]benzoate

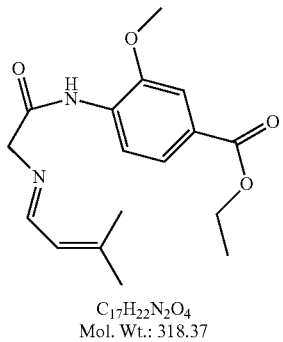 [SMILES: CCOC(=O)c1ccc(NC(=O)C/N=C/C=C(C)C)c(OC)c1]

$C_{17}H_{22}N_2O_4$
Mol. Wt.: 318.37

To a suspension of ethyl 4-(2-aminoacetamido)-3-methoxybenzoate hydrochloride salt (1.50 g, 5.18 mmol) in MTBE (8 mL) was added triethylamine (Aldrich, 628 mg, 6.22 mmol). The mixture was stirred at rt for 30 min. followed by the addition of 3-methylbut-2-enal (Aldrich, 436 mg, 5.18 mmol). The mixture was stirred at rt for 18 hrs. The solid was filtered out and the filtrate was washed with water and brine. Removal of solvent gave the crude which was crystalized from heptane to give a white powder. 1.56 g, 95%. $^1$HNMR (CDCl$_3$, 300 MHz): δ 9.54 (s, br, 1H), 8.53-8.6 (d, 1H, J=8.4 Hz), 8.25-8.30 (d, 1H, J=9.3 Hz), 7.70-7.75 (dd, 1H, J1=8.4 Hz, J2=1.5 Hz), 7.58 (d, 1H, J=1.5 Hz), 6.11 (d, 1H, J=9.3 Hz), 4.30-4.43 (q, 7.2 Hz), 4.30 (s, 1H), 4.0 (s, 3H), 1.99 (d, 6.9 Hz), 1.42 (t, 3H, J=7.2 Hz).

Example 6

Preparation of racemic ethyl 4-[[(2'R,3R,3'S,5'S)-6-chloro-3'-(3-chloro-2-fluoro-phenyl)-5'-(2-methyl-prop-1-enyl)-2-oxo-spiro[indoline-3,4'-pyrrolidine]-2'-carbonyl]amino]-3-methoxy-benzoate

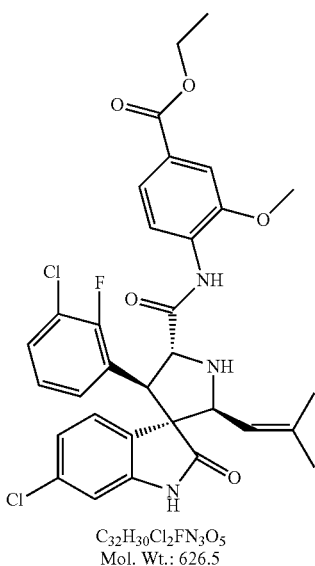 [SMILES: CCOC(=O)c1ccc(NC(=O)[C@@H]2N[C@@H](C=C(C)C)[C@@]3(C(=O)Nc4cc(Cl)ccc43)[C@H]2c2cccc(Cl)c2F)c(OC)c1]

C$_{32}$H$_{30}$Cl$_2$FN$_3$O$_5$
Mol. Wt.: 626.5

A solution of DBU (Aldrich, 0.40 mmol), (E)-ethyl 3-methoxy-4-(2-(3-methylbut-2-enylideneamino)acetamido)benzoate (614 mg, 2.0 mmol) and (E)-3-(3-chloro-2-fluorobenzylidene)-6-chloroindolin-2-one (614 mg, 2 mmol) (Shu et al, Org. Process Res. Dev. 2013, 17, 247-256) in toluene (20 mL) was stirred at gentle reflux under N$_2$ overnight. The reaction mixture was cooled and the solvent was reduced to about 6 mL. To the mixture, 1.2 mL of methanol was added followed by heptane (6 mL) in a drop-wise manner. The mixture was stirred at rt for 30 min. The solid was filtered and dried under vacuum to give an off-white solid. 950 mg, 76%. LC/MS MS(ES+) calculated for C$_{32}$H$_{30}$Cl$_2$FN$_3$O$_5$ (M+H)$^+$: 626.15, found, 626.22.

Example 7

Preparation of racemic 4-[[(2'R,3R,3'S,5'S)-6-chloro-3'-(3-chloro-2-fluoro-phenyl)-5'-(2-methyl-prop-1-enyl)-2-oxo-spiro[indoline-3,4'-pyrrolidine]-2'-carbonyl]amino]-3-methoxy-benzoic acid

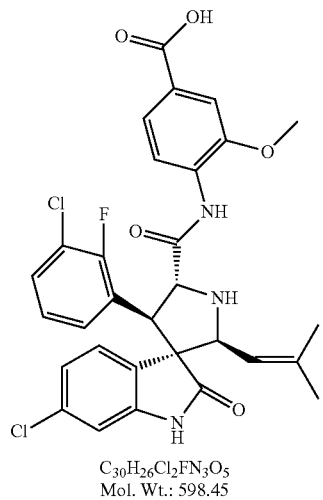 [SMILES: COc1cc(C(=O)O)ccc1NC(=O)[C@@H]1N[C@@H](C=C(C)C)[C@@]2(C(=O)Nc3cc(Cl)ccc32)[C@H]1c1cccc(Cl)c1F]

C$_{30}$H$_{26}$Cl$_2$FN$_3$O$_5$
Mol. Wt.: 598.45

To a stirred solution of ethyl 4-[[(2'R,3R,3'S,5'S)-6-chloro-3'-(3-chloro-2-fluoro-phenyl)-5'-(2-methylprop-1-enyl)-2-oxo-spiro[indoline-3,4'-pyrrolidine]-2'-carbonyl]amino]-3-methoxy-benzoate (860 mg, 1.37 mmol) in a mixture of THF/H$_2$O (4:1, 5 mL) was added NaOH solution (295 mg in 1.2 mL) along with 2 mL of THF. The mixture was stirred at 60° C. for until completion of reaction by TLC (30% EtOAc/hexanes). The media was adjusted to PH=6 with 50% citric acid solution and the mixture was extracted with EtOAc (3×10 mL). Removal of solvent under reduced pressure gave an off-white solid. 810 mg, 93%. LC/MS MS(ES+) calculated for C$_{30}$H$_{26}$Cl$_2$FN$_3$O$_5$ (M+H)$^+$: 598.12, found, 598.15. $^1$HNMR (CDCl$_3$, 300 MHz): δ 10.58 (s, 1H) m 10.48 (s, 1H), 8.37-8.40 (d, 1H, J=8.7 Hz), 7.74-7.78 (d, J=8.1 Hz), 7.5-7.70 (m, 3H), 7.36-7.42 (t, 1H, J=6.9 Hz), 7.15-7.21 (t, 1H, J=8.4 Hz), 6.99-7.03 (dd, 1H, J1=8.1 Hz, J2=1.8 Hz), 6.63-6.64 (d, 1H, J=1.8 Hz), 4.97-5.00 (d, 1H, J=8.1 Hz), 4.60-4.75 9 (m, 2H), 4.56-4.60 (d, 1H, J=10.2 Hz), 3.95 (s, 3H), 1.60 (s, 3H), 1.49 (s, 3H).

Example 8

Preparation of racemic (2'R,3R,3'S,5'S)-N-(4-carbamoyl-2-methoxy-phenyl)-6-chloro-3'-(3-chloro-2-fluoro-phenyl)-5'-(2-methylprop-1-enyl)-2-oxo-spiro[indoline-3,4'-pyrrolidine]-2'-carboxamide

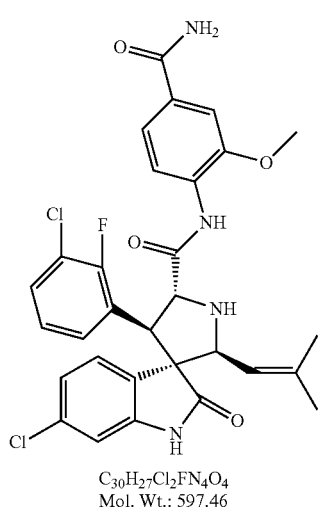 [SMILES: COc1cc(C(N)=O)ccc1NC(=O)[C@@H]1N[C@@H](C=C(C)C)[C@@]2(C(=O)Nc3cc(Cl)ccc32)[C@H]1c1cccc(Cl)c1F]

C30H27Cl2FN4O4
Mol. Wt.: 597.46

To a stirred solution of 4-[[(2'R,3R,3'S,5'S)-6-chloro-3'-(3-chloro-2-fluoro-phenyl)-5'-(2-methylprop-1-enyl)-2-oxo-spiro[indoline-3,4'-pyrrolidine]-2'-carbonyl]amino]-3-methoxy-benzoic acid (280 mg, 0.446 mmol) in THF (6 mL) was added carbodiimide (Aldrich, 145 mg, 0.892 mmol). The mixture was stirred at rt for 1.5 hr and ammonia in water (30%, 4 mL) was added. The mixture was stirred at rt for 15 min. Extraction with EtOAc (3×10 mL) and the solvent was removed under reduced. The residue was chromatographied (EtOAc/Hexane/MeOH, 70:30:3) to give an off white solid. 128 mg, 48%. LC/MS MS (ES+) calculated for $C_{30}H_{27}Cl_2FN_4O_4$ (M+H)+: 597.14. found, 597.15. $^1$HNMR (CDCl$_3$, 300 MHz): δ 10.51 (s, 1H), 10.48 (s, 1H), 8.32 (d, 1H, J=8.1 Hz), 7.95 (s, br, 1H), 7.75-7.78 (d, 1H, J=7.8 Hz), 7.59-7.66 (m, 2H, J=8.7 Hz), 7.50-7.54 (d, 1H, J=8.4 Hz), 7.37-7.40 (t, 1H, J=7.5 Hz), 7.32 (s, br, 1H), 7.16-7.22 (t, 1H, J=7.8 Hz), 6.99-7.02 (d, 1H, J=8.1 Hz), 6.65 (s, 1H), 4.98-5.01 (d, 1H, J=8.1 Hz), 4.65-4.80 (m, 2H), 4.56-4.60 (d, 1H, J=9.9 Hz), 3.95 (s, 3H), 3.85-3.89 (d, 1H, J=10.8 Hz), 1.61 (s, 3H), 1.50 (s, 3H).

Example 9a

Preparation of racemic ethyl 4-[[(2'R,3R,3'S,5'S)-6-chloro-3'-(3-chloro-2-fluoro-phenyl)-2-oxo-5'-[(2R)-3,3,3-trifluoro-2-methyl-propyl]spiro[indoline-3,4'-pyrrolidine]-2'-carbonyl]amino]-3-methoxy-benzoate

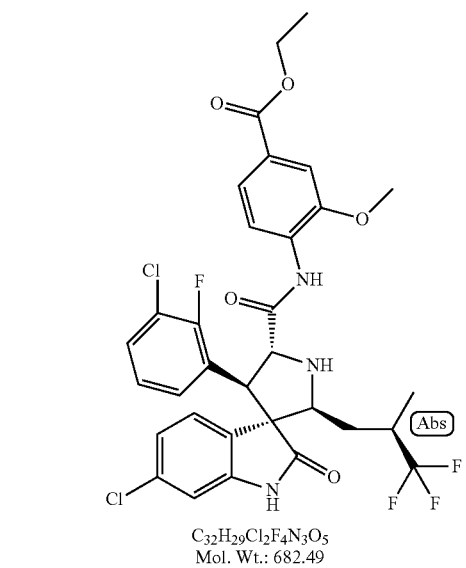 [SMILES: CCOC(=O)c1ccc(NC(=O)[C@@H]2N[C@@H](C[C@@H](C)C(F)(F)F)[C@@]3(C(=O)Nc4cc(Cl)ccc43)[C@H]2c2cccc(Cl)c2F)c(OC)c1]

C32H29Cl2F4N3O5
Mol. Wt.: 682.49

A solution of DBU (Aldrich, 0.40 mmol), (E)-ethyl 3-methoxy-4-(2-(4,4,4-trifluoro-3-methylbutylideneamino)acetamido)benzoate (793.62 mg, 2.12 mmol) and (E)-3-(3-chloro-2-fluorobenzylidene)-6-chloroindolin-2-one (614 mg, 2 mmol) (Shu et al, Org. Process Res. Dev. 2013, 17, 247-256) in toluene (10 mL) was stirred at gentle reflux under N2 for 24 hr. The reaction mixture was cooled and the solvent was reduced to about 6 mL. Chromatography (30% EtOAc/hexanes) gave three major products. The first isomer easily crystalized out from eluent and collected by filtration (170 mg) but is not the desired stereoisomer. The second (191 mg) and third (270 mg) diastereomers turned out to be desired isomers. The absolute stereo-center of the CF$_3$ connecting center was determined by using chiral aldehyde as described in the text later in this invention. Then the first isomer and other isomers were combined and dissolved in toluene (6 mL) and refluxed with DBU (47 mg) for 24 hr. Chromatography (30% EtOAc/hexanes) gave an additional amount of isomer two (240 mg) and isomer three (160 mg). Total amount of racemic ethyl 4-[[(2'R,3R,3'S,5'S)-6-chloro-3'-(3-chloro-2-fluoro-phenyl)-2-oxo-5'-[(2R)-3,3,3-trifluoro-2-methyl-propyl]spiro[indoline-3,4'-pyrrolidine]-2'-carbonyl]amino]-3-methoxy-benzoate: 431 mg. Yield, 32%. $^1$H NMR (300 MHz, CDCl3). δ 10.67 (s, 1H), 10.58 (s, 1H), 8.39-8.42 (d, 1H, J=7.8 Hz), 7.74-7.77 (d, 1H, J=8.4 Hz), 7.50-7.70 (m, 3H), 7.38-7.43 (t, 1H, J=6.9 Hz), 7.17-7.23 (t, 7.8 Hz), 7.05-7.09 (dd, 1H, J1=8.40 HZ), 6.71 (d, 1H, J=1.8 Hz), 4.64-4.70 (t, 1H, J=8.7 Hz), 4.57-4.60 (d, 1H, J=9.6 Hz), 4.28-4.35 (q, 7.2 Hz), 4.18 (m, 1H), 3.96 (s, 4H), 2.75 (m, 1H), 1.66-1.73 (t, 1H, J=9.9 Hz), 1.34 (t, 3H, J=7.2 Hz), 1.15-1.18 (d, 3H, J=6.9 Hz), 0.85-0.93 (t, 1H, J=13.4 Hz).

Example 9b

Preparation of ethyl 4-[[(2'R,3R,3'S,5'S)-6-chloro-3'-(3-chloro-2-fluoro-phenyl)-2-oxo-5'-[(2S)-3,3,3-trifluoro-2-methyl-propyl]spiro[indoline-3,4'-pyrrolidine]-2'-carbonyl]amino]-3-methoxy-benzoate

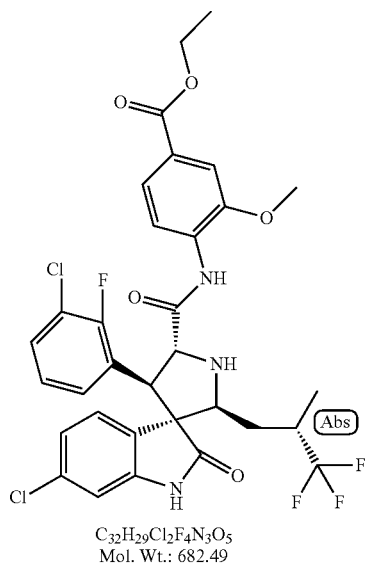 [SMILES: CCOC(=O)c1ccc(NC(=O)[C@@H]2N[C@@H](C[C@H](C)C(F)(F)F)[C@@]3(C(=O)Nc4cc(Cl)ccc43)[C@H]2c2cccc(Cl)c2F)c(OC)c1]

$C_{32}H_{29}Cl_2F_4N_3O_5$
Mol. Wt.: 682.49

Follow the experiment for the preparation of example 9a, A total amount of 430 mg of racemic ethyl 4-[[(2'R,3R,3'S,5'S)-6-chloro-3'-(3-chloro-2-fluoro-phenyl)-2-oxo-5'-[(2S)-3,3,3-trifluoro-2-methyl-propyl]spiro[indoline-3,4'-pyrrolidine]-2'-carbonyl]amino]-3-methoxy-benzoate was obtained. LC/MS MS (ES+) calculated for $C_{32}H_{29}Cl_2F_4N_3O_5$ (M+H)$^+$: 682.14, found, 682.22. $^1$H NMR (300 MHz, CDCl3). δ 10.66 (s, 1H), 10.59 (s, 1H), 8.39-8.42 (d, 1H, J=7.8 Hz), 7.69-7.72 (d, 1H, J=7.5 Hz), 7.50-7.65 (m, 3H), 7.38-7.43 (t, 1H, J=6.9 Hz), 7.17-7.23 (t, 7.8 Hz), 7.05-7.09 (dd, 1H, J1=8.40 HZ), 6.71 (d, 1H, J=1.8 Hz), 4.64-4.75 (t, 1H, J=8.7 Hz), 4.52-4.56 (d, 1H, J=9.3 Hz), 4.28-4.35 (q, 7.2 Hz), 4.18 (m, 1H), 3.95 (s, 3H), 3.85-3.95 (m, 1H), 2.3-2.4 (m, 1H), 1.4-1.55 (m, 2H), 1.30-1.35 (t, 3H, J=7.2 Hz), 1.20-1.22 (d, 3H, J=6.9 Hz).

Example 10

Preparation of racemic 4-[[(2'R,3R,3'S,5'S)-6-chloro-3'-(3-chloro-2-fluoro-phenyl)-2-oxo-5'-[(2S)-3,3,3-trifluoro-2-methyl-propyl]spiro[indoline-3,4'-pyrrolidine]-2'-carbonyl]amino]-3-methoxy-benzoic acid

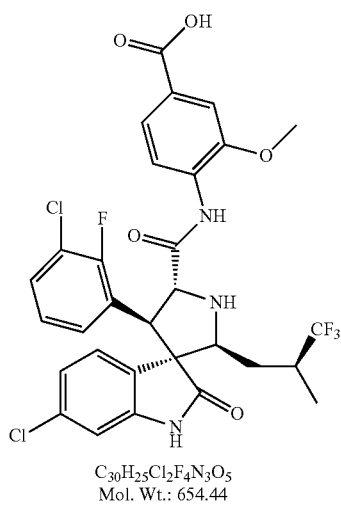 [SMILES: COc1cc(C(=O)O)ccc1NC(=O)[C@@H]1N[C@@H](C[C@H](C)C(F)(F)F)[C@@]2(C(=O)Nc3cc(Cl)ccc32)[C@H]1c1cccc(Cl)c1F]

$C_{30}H_{25}Cl_2F_4N_3O_5$
Mol. Wt.: 654.44

Racemic ethyl 4-[[(2'R,3R,3'S,5'S)-6-chloro-3'-(3-chloro-2-fluoro-phenyl)-2-oxo-5'-[(2S)-3,3,3-trifluoro-2-methyl-propyl]spiro[indoline-3,4'-pyrrolidine]-2'-carbonyl]amino]-3-methoxy-benzoate (200 mg, 0.29 mmol) was dissolved in a mixture of THF (4 mL) and NaOH solution (75 mg NaOH in 1 mL of water). The new mixture was stirred at 60° C. for 21 hrs under nitrogen. Then an additional 25 mg of NaOH in 0.5 mL of water was added and the mixture was heated and stirred under nitrogen for 24 hrs. 1 N HCl was added to PH=5. The mixture was extracted with EtOAc (3×6 mL) and dried (Na$_2$SO$_4$). Evaporation of solvent gave an off-white solid. 189 mg, 99%. (LC/MS MS (ES+) calculated for $C_{30}H_{25}Cl_2F_4N_3O_5$(M+H)$^+$: 654.11, found, 654.12. $^1$H NMR (300 MHz, CDCl3) δ 10.64 (s, 1H), 10.61 (s, 1H), 8.35-8.39 (d, 1H, J=8.7 Hz), 7.69-7.72 (d, 1H, J=8.1 Hz), 7.50-7.64 (m, 3H), 7.38-7.42 (t, 1H, J=6.9 Hz), 7.16-7.22 (t, 1H, 8.4 Hz), 7.04-7.08 (dd, 1H, J1=8.1 Hz, J2=1.8 Hz), 6.71-6.72 (d, 1H, J=1.8 Hz), 4.67-4.71 (d, 1H, 9.3 Hz), 4.56-4.60 (d, 1H, J=9.6 Hz), 4.10-4.22 (m, 1H), 3.95 (s, 3H), 3.80-4.0 (m, 1H), 2.30-2.43 (m, 1H), 1.41-1.52 (m, 1H), 1.27-1.40 (m, 1H), 1.20-1.23 (d, 3H, J=6.9 Hz).

Example 11

Preparation of racemic 4-[[(2'R,3R,3'S,5'S)-6-chloro-3'-(3-chloro-2-fluoro-phenyl)-2-oxo-5'-[(2R)-3,3,3-trifluoro-2-methyl-propyl]spiro[indoline-3,4'-pyrrolidine]-2'-carbonyl]amino]-3-methoxy-benzoic acid

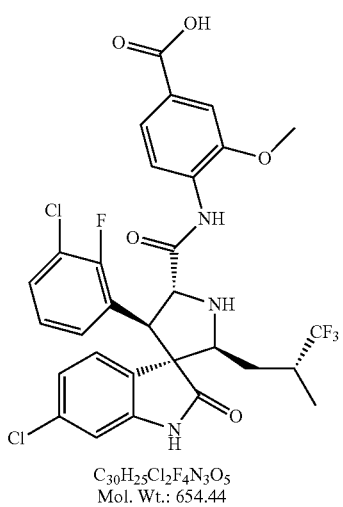 [SMILES: COc1cc(C(=O)O)ccc1NC(=O)[C@@H]1N[C@@H](C[C@@H](C)C(F)(F)F)[C@@]2(C(=O)Nc3cc(Cl)ccc32)[C@H]1c1cccc(Cl)c1F]

$C_{30}H_{25}Cl_2F_4N_3O_5$
Mol. Wt.: 654.44

By a similar procedure for the preparation of 4-[[(2'R,3R,3'S,5'S)-6-chloro-3'-(3-chloro-2-fluoro-phenyl)-2-oxo-5'-[(2S)-3,3,3-trifluoro-2-methyl-propyl]spiro[indoline-3,4'-pyrrolidine]-2'-carbonyl]amino]-3-methoxy-benzoic acid, 4-[[(2'R,3R,3'S,5'S)-6-chloro-3'-(3-chloro-2-fluoro-phenyl)-2-oxo-5'-[(2R)-3,3,3-trifluoro-2-methyl-propyl]spiro[indoline-3,4'-pyrrolidine]-2'-carbonyl]amino]-3-methoxy-benzoic acid was prepared by the hydrolysis of isomer two. (LC/MS MS (ES+) calculated for $C_{30}H_{25}Cl_2F_4N_3O_5$(M+H)$^+$: 654.11, found, 654.15. $^1$H NMR (300 MHz, CDCl3) δ 10.64 (s, 1H), 10.59 (s, 1H), 8.35-8.39 (d, 1H, J=8.7 Hz), 7.73-7.77 (d, 1H, J=8.4 Hz), 7.42-70 (m, 3H), 7.38-7.44 (t, 1H, J=7.2 Hz), 7.17-7.22 (t, 1H, 8.1 Hz), 7.04-7.08 (dd, 1H, J1=7.8 Hz, J2=1.8 Hz), 6.70-6.71 (d, 1H, J=1.8 Hz), 4.65 (d, 1H, 9.3 Hz), 4.56-4.60 (d, 1H, J=9.3 Hz), 4.10-4.22 (m, 1H), 3.95 (s, 3H), 3.80-4.0 (m, 1H), 2.60-2.80 (m, 1H), 1.70 (t, 1H, J=12.3 Hz), 1.15-1.18 (d, 3H, J=6.9 Hz), 0.84-0.90 (t, 1H, J=12.3 Hz).

Example 12

Preparation of racemic (2'R,3R,3'S,5'S)-N-(4-carbamoyl-2-methoxy-phenyl)-6-chloro-3'-(3-chloro-2-fluoro-phenyl)-2-oxo-5'-[(2S)-3,3,3-trifluoro-2-methyl-propyl]spiro[indoline-3,4'-pyrrolidine]-2'-carboxamide

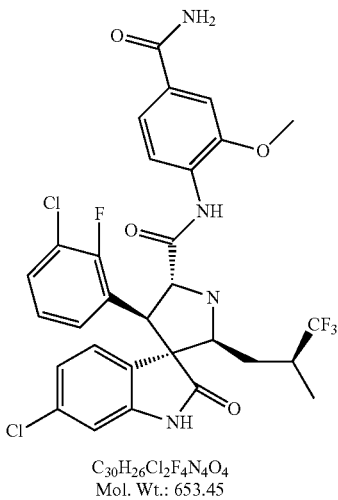 [SMILES: COc1cc(C(N)=O)ccc1NC(=O)[C@@H]1N[C@@H](C[C@H](C)C(F)(F)F)[C@@]2(C(=O)Nc3cc(Cl)ccc32)[C@H]1c1cccc(Cl)c1F]

$C_{30}H_{26}Cl_2F_4N_4O_4$
Mol. Wt.: 653.45

4-[[(2'R,3R,3'S,5'S)-6-chloro-3'-(3-chloro-2-fluoro-phenyl)-2-oxo-5'-[(2S)-3,3,3-trifluoro-2-methyl-propyl]spiro[indoline-3,4'-pyrrolidine]-2'-carbonyl]amino]-3-methoxy-benzoic acid (66 mg, 0.10 mmol) was dissolved in THF (3 mL). To the stirred solution, CDI (Aldrich, 33 mg, 0.20 mmol) was added and the mixture was stirred for 1 hr at rt. Ammonia (30%, 2 mL) was added and the new mixture was stirred for 15 min. at rt. The mixture was extracted with EtOAc (3×10 mL) and concentrated. Chromatography of the residue (70% EtOAc/hexane) gave an off-white solid. 58 mg, 89%. LC/MS MS (ES+) calculated for $C_{30}H_{26}Cl_2F_4N_4O_4$ (M+H)$^+$: 653.13, found, 653.19.

$^1$H NMR (300 MHz, CDCl3) δ 10.65 (s, 1H), 10.63 (s, 1H), 8.35-8.39 (d, 1H, J=8.7 Hz), 8.05 (s, br, 1H), 7.74-7.77 (d, 1H, J=8.1 Hz), 7.62-7.7.73 (m, 2H), 7.55-7.58 (d, 1H, J=8.1 Hz), 7.43-7.49 (t, 1H, J=7.8 Hz), 7.37 (s, br, 1H), 7.22-7.28 (t, 1H, J=8.4 Hz), 7.10-7.14 (d, 1H, J=8.4 Hz), 6.77 (s, 1H), 4.71-4.81 (m, 1H), 4.56-4.59 (d, 1H, J=9.6 Hz), 4.10-4.25 (m, 1H), 3.98 (s, 3H), 3.80-4.0 (m, 1H), 2.30-2.5 (m, 1H), 1.46-1.60 (m, 1H), 1.27-1.46 (m, 1H), 1.26-1.29 (d, 3H, J=6.9 Hz).

Example 13

Preparation of racemic (2'R,3R,3'S,5'S)-N-(4-carbamoyl-2-methoxy-phenyl)-6-chloro-3'-(3-chloro-2-fluoro-phenyl)-2-oxo-5'-[(2R)-3,3,3-trifluoro-2-methyl-propyl]spiro[indoline-3,4'-pyrrolidine]-2'-carboxamide

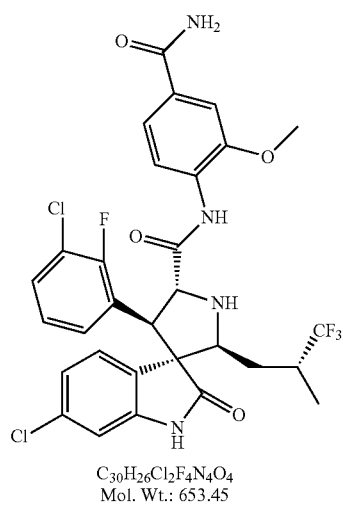 [SMILES: COc1cc(C(N)=O)ccc1NC(=O)[C@@H]1N[C@@H](C[C@@H](C)C(F)(F)F)[C@@]2(C(=O)Nc3cc(Cl)ccc32)[C@H]1c1cccc(Cl)c1F]

C30H26Cl2F4N4O4
Mol. Wt.: 653.45

4-[[(2'R,3R,3'S,5'S)-6-chloro-3'-(3-chloro-2-fluoro-phenyl)-2-oxo-5'-[(2R)-3,3,3-trifluoro-2-methyl-propyl]spiro[indoline-3,4'-pyrrolidine]-2'-carbonyl]amino]-3-methoxybenzoic acid (66 mg, 0.10 mmol) was dissolved in THF (3 mL). To the stirred solution, CDI (Aldrich, 33 mg, 0.20 mmol) was added and the mixture was stirred for 1 hr at rt. Ammonia (30%, 2 mL) was added and the new mixture was stirred for 15 min. at rt. The mixture was extracted with EtOAc (3×10 mL) and concentrated. Chromatography of the residue (70% EtOAc/hexane) gave an off-white solid. 54 mg, 83%. LC/MS MS (ES+) calculated for C30H26Cl2F4N4O4 (M+H)+: 653.13, found, 653.19. 1H NMR (300 MHz, CDCl3) δ 10.57 (s, 2H), 8.29-8.33 (d, 1H, J=7.8 Hz), 7.94 (s, br, 1H), 7.73-7.76 (d, 1H, J=8.4 Hz), 7.52-7.62 (m, 2H), 7.50-7.53 (d, 1H, J=8.4 Hz), 7.37-7.40 (t, 1H, J=6.9 Hz), 7.31 (s, br, 1H), 7.22-7.28 (t, 1H, J=8.4 Hz), 7.10-7.14 (dd, 1H, J1=7.8 Hz, J2=1.8 Hz), 6.70-6.71 (d, 1H, J=1.8 Hz), 4.60-4.71 (m, 1H), 4.54-4.58 (d, 1H, J=9.6 Hz), 4.10-4.25 (m, 1H), 3.94 (s, 3H), 3.80-4.0 (m, 1H), 2.64-2.73 (m, 1H), 1.60-1.80 (m, 1H), 1.17 (d, 3H, J=6.9 Hz), 0.80-0.95 (m, 1H).

Example 14

Preparation of 3-cyano-2,2-dimethylpropyl trifluoromethanesulfonate

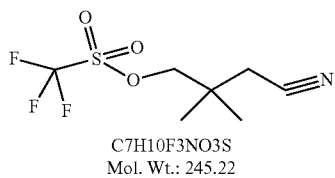

C7H10F3NO3S
Mol. Wt.: 245.22

4-Hydroxy-3,3-dimethylbutanenitrile (US2012/220767 A1) (2.40 g, 21.24 mmol) was dissolved in DCM (15 mL) and the solution was cooled to −78° C. To the stirred solution, pyridine (Aldrich, 2.1 mL, 26 mmol) and triflic anhydride (Aldrich, 4.28 mL, 25.5 mmol) were added successively and the mixture was stirred at −78° C. for 1 h. The organic layer was separated and the aqueous layer was extracted with DCM (2×5 mL). The extracts were combined and dried with sodium sulfate. Removal of solvent gave an orange oil. 4.59 g, 88%. 1H NMR (300 MHz, CDCl3) δ 4.38 (s, 2H), 2.48 (s, 2H), 1.23 (s, 6H).

Example 15

Preparation of 4-fluoro-3,3-dimethylbutanenitrile

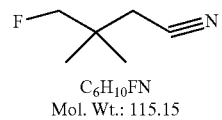

C6H10FN
Mol. Wt.: 115.15

3-Cyano-2,2-dimethylpropyl trifluoromethanesulfonate (2.49 g, 10 mmol) was dissolved in ether (10 mL) and the solution was cooled to 0° C. To the stirred solution was added tetrabutylammonium fluoride (Aldrich, 13 mL, 13 mmol, 1 M solution in THF) and the mixture was gradually warmed to rt and stirred overnight. The mixture was poured into water and extracted with ether. The extract was dried with sodium sulfate and the solvent was removed under reduced pressure (350 mmHg with bath temperature at 35° C.) to give a pale yellow liquid. 0.97 g, 84%. 1H NMR (300 MHz, CDCl3) δ 4.14-4.30 (d, 1H, J=47.4 Hz), 2.42 (s, 2H), 1.15 (d, 6H, J=1.8 Hz).

Example 16

Preparation of 4-fluoro-3,3-dimethylbutanal

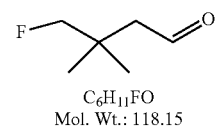

C6H11FO
Mol. Wt.: 118.15

4-Fluoro-3,3-dimethylbutanenitrile (0.72 g, 6.26 mmol) was dissolved in DCM (5 mL) and the solution was cooled to −78° C. To the stirred solution was added DIBAL (Aldrich, 9.4 mL. 9.4 mmol) in DCM and the mixture was stirred at −78° C. for 2 hr. The reaction was quenched with 20% AcOH (10 mL) at −78° C. The mixture was slowly warmed to rt and 10 mL of ammonium chloride (sat.) was added and the mixture was stirred until a clear solution formed. The organic layer was separated and washed with saturated sodium bicarbonate and dried (Na2SO4). The solvent was removed and the residue was filtered through a short pad of silica gel and eluted with diethyl ether. Removal of solvent gave a colorless oil. 0.70 g, 95%. 1H NMR (300 MHz, CDCl3). δ 9.88 (s, 1H), 4.15-4.42 (d, 1H, J=48.3 Hz), 2.44-2.24 (d, 2H, J=2.7 Hz), 1.12 (s, 6H).

Example 17

Preparation of (E)-ethyl 4-(2-(4-fluoro-3,3-dimethylbutylideneamino)acetamido)-3-methoxybenzoate

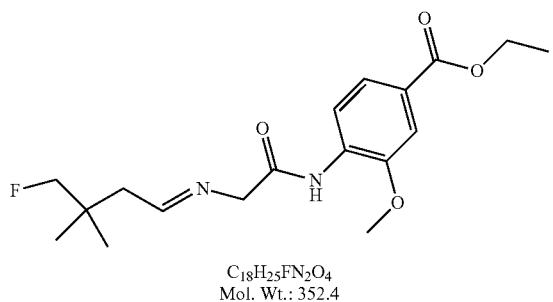 [SMILES: CCOC(=O)c1ccc(NC(=O)C/N=C/CC(C)(C)CF)c(OC)c1]

$C_{18}H_{25}FN_2O_4$
Mol. Wt.: 352.4

Ethyl 4-(2-aminoacetamido)-3-methoxybenzoate (758.75 mg, 2.5 mmol), $Et_3N$ (303 mg, 3 mmol) and 4-fluoro-3,3-dimethylbutanal (295 mg, 2.5 mmol) were suspended in MTBE (Aldrich, 7 mL) and the mixture was stirred at rt overnight. Wash with water and the organic layer was dried with sodium sulfate. Removal of solvent under reduced pressure gave a white solid. 800 mg, 99%. $^1$H NMR (300 MHz, CDCl3) δ 9.52 (s, 1H), 8.54-8.58 (d, 1H, J=8.4 Hz), 7.90 (triplet, 1H, J=5.4 Hz), 7.70-7.80 (d, 1H, J=8.4 Hz), 7.60 (s, 1H), 4.30-4.50 (q, 2H, 6.9 Hz), 4.15-4.33 (d, 2H, J=47.7), 4.26 (s, 2H), 3.98 (s, 3H), 2.42-2.45 (d, 2H, J=5.4 Hz), 1.40-1.47 (t, 3H, J=6.9 Hz), 1.10 (d, 6H, J=1.5 Hz).

Example 18

Preparation of racemic (4-ethoxycarbonyl-2-methoxy-phenyl) (2'R,3R,3'S,5'S)-6-chloro-3'-(3-chloro-2-fluoro-phenyl)-5'-(3-fluoro-2,2-dimethyl-propyl)-2-oxo-spiro[indoline-3,4'-pyrrolidine]-2'-carboxamide

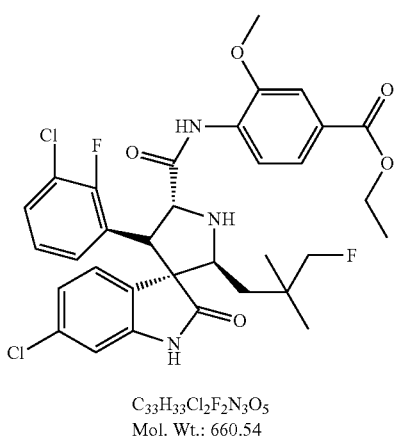

$C_{33}H_{33}Cl_2F_2N_3O_5$
Mol. Wt.: 660.54

A solution of DBU (Aldrich, 69.3 mmol), (E)-ethyl 4-(2-(4-fluoro-3,3 dimethylbutylideneamino)acetamido)-3-methoxybenzoate (807 mg, 2.51 mmol) and (E)-3-(3-chloro-2-fluorobenzylidene)-6-chloroindolin-2-one (700 mg, 2.28 mmol) (Shu et al, Org. Process Res. Dev. 2013, 17, 247-256) in toluene (12 mL) was stirred at gentle reflux under $N_2$ for 22.5 hr. The mixture was cooled and 12 mL of heptane and 2 mL of methanol were added and the new mixture was further stirred at rt for 2 hr. The solid was filtered and washed with toluene/heptane/methanol (5:5:1, 10 mL) and dried under vacuum to give an off-white solid. 1.12 g, 74%. The ester was used directly for the next step.

Example 19

Preparation of racemic 4-[(2'R,3R,3'S,5'S)-6-chloro-3'-(3-chloro-2-fluoro-phenyl)-5'-(3-fluoro-2,2-dimethyl-propyl)-2-oxo-spiro[indoline-3,4'-pyrrolidine]-2'-carbonyl]amino-3-methoxy-benzoic acid

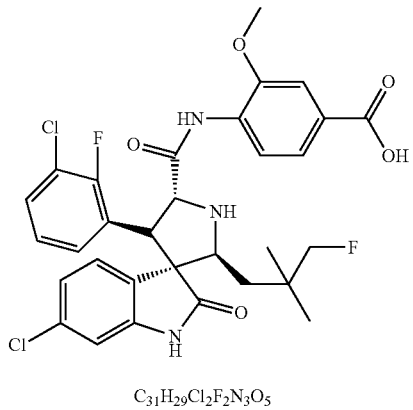

$C_{31}H_{29}Cl_2F_2N_3O_5$
Mol. Wt.: 632.48

(4-Ethoxycarbonyl-2-methoxy-phenyl) (2'R,3R,3'S,5'S)-6-chloro-3'-(3-chloro-2-fluoro-phenyl)-5'-(3-fluoro-2,2-dimethyl-propyl)-2-oxo-spiro[indoline-3,4'-pyrrolidine]-2'-carboxamide (1.12 g, 1.66 mmol) was dissolved in a mixture of THF and 50% NaOH(5 mL of THF, 1 mL of 50% NaOH) and the mixture was stirred at 70° C. for 6 hrs. The mixture was cooled and 1 mL of 50% NaOH was added and the new mixture was extracted with ether (2×20 mL). The aqueous layer (containing some solid) was acidified with 4N HCl to PH=4. The solid was filtered and dried in a vacuum oven at 50° C. to give an off-white solid. 996 mg, 93%. 1H NMR (300 MHz, DMSO). 10.73 (s, 1H), 10.53 (s, 1H), 8.40-8.45 (d, 1H, J=8.7 Hz), 7.72-7.77 (d, 1H, J=7.8 Hz), 7.55-7.70 (d, 1 H, J=8.4 Hz), 7.40 (t, 1 H, J=6.6 Hz), 7.20 (t, 1 H, J=8.1 Hz), 7.03-7.07 (dd, 1 H, J1=7.8 Hz, J2=1.8Hz), 6.71 (d, 1 H, J=1.8 Hz), 4.70 (m, 1H), 4.50-4.53 (d, 1H, J=9 Hz), 4.14-4.32 (d, 2H, J=47.7 Hz), 3.95 (s, 3H), 3.85-3.95(m, 1 H), 3.70-3.78(m, 1 H), 1.35-1.45 (dd, 1H, J1=13.8 Hz, J2=9.9 Hz), 0.99 (s, 3 H), 0.91 (s, 3H), 0.84-0.90 (d, 1H, J=14 Hz).

Example 20

Preparation of racemic (4-carbamoyl-2-methoxy-phenyl) (2'R,3R,3'S,5'S)-6-chloro-3'-(3-chloro-2-fluoro-phenyl)-5'-(3-fluoro-2,2-dimethyl-propyl)-2-oxo-spiro[indoline-3,4'-pyrrolidine]-2'-carboxamide

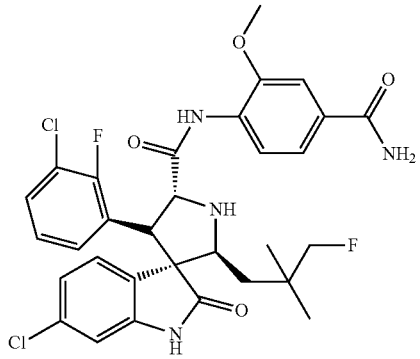

C$_{31}$H$_{30}$Cl$_2$F$_2$N$_4$O$_4$
Mol. Wt.: 631.5

To a stirred solution of 4-[(2'R,3R,3'S,5'S)-6-chloro-3'-(3-chloro-2-fluoro-phenyl)-5'-(3-fluoro-2,2-dimethyl-propyl)-2-oxo-spiro[indoline-3,4'-pyrrolidine]-2'-carbonyl]amino-3-methoxy-benzoic acid (65 mg, 0.10 mmol) in THF (3 mL), CDI (Aldrich, 34 mg, 0.20 mmol) was added and the mixture was stirred at rt for 1 hr. To the stirred solution, concentrated ammonia (38%, 2 mL) was added and the new mixture was stirred at rt for 15 min. The mixture was extracted with DCM (2×5 mL). The extract was washed with 1N HCl and dried with sodium sulfate. Removal of solvent gave an off-white solid. 60 mg, 92%. $^1$H NMR (300 MHz, DMSO). 10.65 (s, 1H), 10.54 (s, 1 H), 8.33-8.40 (d, 1H, J=9.0 Hz), 7.96 (s, 1 H), 7.72-7.75(d, 1 H, J=7.8 Hz), 7.725 (s, 1H), 7.55-7.70 (m, 3 H, J=8.4 Hz), 7.5-7.55 (dd, 1H, J1=8.40, J2=1.5Hz), 7.30-7.44 (t, 1 H, J=7.2 Hz), 7.33 (s, br, 1 H), 7.20 (t, 1 H, J=8.4 Hz), 7.03-7.07 (dd, 1 H, J1=8.4 Hz, J2=1.8Hz), 6.71 (d, 1 H, J=2.1Hz), 4.60-4.80 (m, 1H), 4.49-4.53 (d, 1 H, J=9.0 Hz), 4.14-4.40 (d, 2H, J=47.7 Hz), 3.95 (s, 3H), 3.85-3.95(m, 1 H), 3.70-3.78(m, 1 H), 1.35-1.45 (dd, 1H, J1=13.8 Hz, J2=9.9Hz), 0.99 (s, 3 H), 0.91 (s, 3H), 0.84-0.90 (d, 1H, J=14 Hz).

Example 21

Preparation of chiral 4-[(2'R,3R,3'S,5'S)-6-chloro-3'-(3-chloro-2-fluoro-phenyl)-5'-(3-fluoro-2,2-dimethyl-propyl)-2-oxo-spiro[indoline-3,4'-pyrrolidine]-2'-carbonyl]amino-3-methoxy-benzoic acid

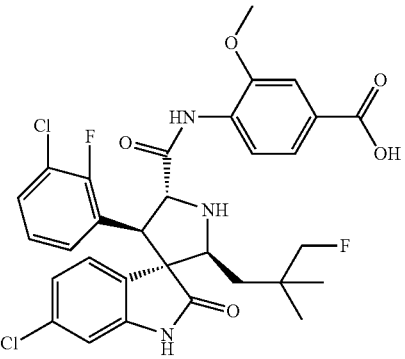

C$_{31}$H$_{29}$Cl$_2$F$_2$N$_3$O$_5$
Mol. Wt.: 632.48

(4-carboxyl-2-methoxy-phenyl) (2'R,3R,3'S,5'S)-6-chloro-3'-(3-chloro-2-fluoro-phenyl)-5'-(3-fluoro-2,2-dimethyl-propyl)-2-oxo-spiro[indoline-3,4'-pyrrolidine]-2'-carboxamide (466 mg, 0.74 mmol) was dissolved in EtOAc (4 mL). To the stirred solution, (R)-N,N-dimethyl-1-phenylethanamine (Aldrich, 110 mg, 0.74 mmol) was added and the mixture was heated at 60° C. for 2 hr and gradually cooled to rt and stirred for overnight. The solid was filtered and dried to give the desired salt. 227 mg.

$^1$H NMR (300 MHz, DMSO). δ 10.71 (s, 1H), 10.57 (s, 1H), 8.35-8.45 (d, 1H, J=8.4 Hz), 7.72-7.77 (d, 1H, J=8.1 Hz), 7.55-7.70 (m, 3H), 7.41 (t, 1H, J=6.6 Hz), 7.15-7.34 (m, 6H), 7.03-7.07 (dd, 1H, J1=8.1 Hz, J2=1.8 Hz), 6.72 (d, 1H, J=1.8 Hz), 4.70 (m, 1H), 4.50-4.51 (d, 1H, J=9 Hz), 4.14-4.32 (d, 2H, J=47.7 Hz), 3.95 (s, 3H), 3.85-3.95 (m, 1H), 3.70-3.78 (m, 1H), 2.12 (s, 6H), 1.35-1.50 (dd, 1H, J1=13.8 Hz, J2=9.9 Hz), 1.25-1.32 (d, 3H), 1.0 (s, 3H), 0.92 (s, 3H), 0.60-0.80 (d, 1H, J=14 Hz).

The salt was suspended in EtOAc (8 mL) and 10 mL of 2N HCl was added with 1 mL of THF. The mixture was vigorously stirred at rt. The organic layer was separated and dried (Na$_2$SO$_4$). Removal of solvent under reduce pressure gave a white solid. 189 mg. %. $^1$H NMR (300 MHz, DMSO). δ 12.80 (s, br, 1H), 10.73 (s, 1H), 10.53 (s, 1H), 8.40-8.45 (d, 1H, J=8.7 Hz), 7.72-7.77 (d, 1H, J=7.8 Hz), 7.50-7.75 (m, 4H), 7.40 (t, 1H, J=6.6 Hz), 7.20 (t, 1H, J=8.1 Hz), 7.03-7.07 (d, 1H, J1=7.8 Hz), 6.71 (s, 1H), 4.70 (m, 1H), 4.50-4.53 (d, 1H, J=9.3 Hz), 4.14-4.32 (d, 2H, J=47.8 Hz), 3.95 (s, 3H), 3.85-3.95 (m, 1H), 3.70-3.78 (m, 1H), 1.35-1.45 (dd, 1H, J1=13.8 Hz, J2=9.9 Hz), 0.99 (s, 3H), 0.91 (s, 3H), 0.84-0.90 (d, 1H, J=14 Hz).

Example 22

Preparation of chiral (4-carbamoyl-2-methoxy-phenyl) (2'R,3R,3'S,5'S)-6-chloro-3'-(3-chloro-2-fluoro-phenyl)-5'-(3-fluoro-2,2-dimethyl-propyl)-2-oxo-spiro[indoline-3,4'-pyrrolidine]-2'-carboxamide

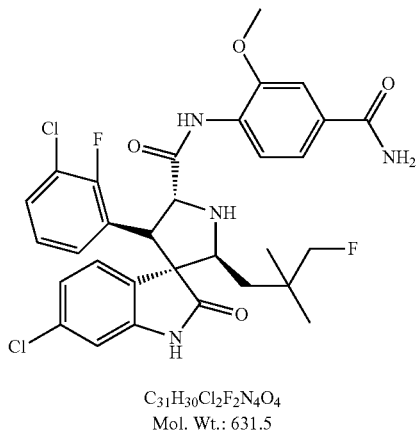

$C_{31}H_{30}Cl_2F_2N_4O_4$
Mol. Wt.: 631.5

To a stirred solution of 4-[(2'R,3R,3'S,5'S)-6-chloro-3'-(3-chloro-2-fluoro-phenyl)-5'-(3-fluoro-2,2-dimethyl-propyl)-2-oxo-spiro[indoline-3,4'-pyrrolidine]-2'-carbonyl]amino-3-methoxy-benzoic acid (70 mg, 0.11 mmol) in THF (3 mL), CDI (Aldrich, 38 mg, 0.22 mmol) was added and the mixture was stirred at rt for 1 hr. To the stirred solution, concentrated ammonia (38%, 2 mL) was added and the new mixture was stirred at rt for 15 min. The mixture was extracted with DCM (2×5 mL) and washed with 1 HCl. The extract was dried with sodium sulfate. Removal of solvent gave an off-white solid. 65 mg, 93%. $^1$H NMR (300 MHz, DMSO). 10.65 (s, 1H), 10.54 (s, 1 H), 8.33-8.40 (d, 1H, J=9.0 Hz), 7.96 (s, 1 H), 7.72-7.75(d, 1 H, J=7.8 Hz), 7.725 (s, 1H), 7.55-7.70 (m, 3 H, J=8.4 Hz), 7.5-7.55 (dd, 1H, J1=8.40, J2=1.5 Hz), 7.30-7.44 (t, 1 H, J=7.2 Hz), 7.33 (s, br, 1 H), 7.20 (t, 1 H, J=8.4 Hz), 7.03-7.07 (dd, 1 H, J1=8.4 Hz, J2=1.8Hz), 6.71 (d, 1 H, J=2.1Hz), 4.60-4.80 (m, 1H), 4.49-4.53 (d, 1 H, J=9.0 Hz), 4.14-4.40 (d, 2H, J=47.7 Hz), 3.95 (s, 3H), 3.85-3.95(m, 1 H), 3.70-3.78(m, 1 H), 1.35-1.45 (dd, 1H, J1=13.8 Hz, J2=9.9Hz), 0.99 (s, 3 H), 0.91 (s, 3H), 0.84-0.90 (d, 1H, J=14 Hz).

Example 23

Preparation of (R)-4,4,4-trifluoro-3-methylbutan-1-ol

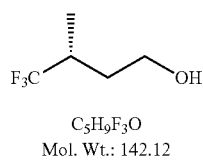

$C_5H_9F_3O$
Mol. Wt.: 142.12

(R)-4,4,4-trifluoro-3-methylbutanoic acid (Pigza et al, *J. Org. Chem.*, 2009, 74(15), 5510-5515, and WO2009/121919, 0.35 g, 2.24 mmol) was dissolved in THF (5 mL) and the solution was cooled to –78° C. Lithium aluminumtetrahydride (63 mg, 1.65 mmol) was added and the mixture was stirred at –78° C. for 1 h and then at rt for 20 min. The mixture was cooled to 0° C. and water was added followed by 4 N HCl. Extraction with ether (3×8 mL) and the extract was dried with sodium sulfate. Removal of solvent gave an oil. 0.23 g, 72%.

Example 24

Preparation of (R)-4,4,4-trifluoro-3-methylbutanal

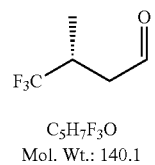

$C_5H_7F_3O$
Mol. Wt.: 140.1

To a stirred solution of oxylyl chloride (2.55 g, 20.1 mmol) in DCM (8 mL) was added DMSO (2.09 g, 26.72 mmol) slowly at –78° C. The mixture was stirred at –78° C. for 15 min. (R)-4,4,4-Trifluoro-3-methylbutan-1-ol (0.95 g, 6.68 mmol) was added with 2 mL of DCM and the mixture was stirred for 1 hr at –78° C. before Et$_3$N (4.06 g, 40.08 mmol) was slowly added. The mixture was gradually warmed to rt over 20 min. and 1N HCl was added. The DCM layer was separated and dried with sodium sulfate and filtered through a short pad of silica gel column. Removal of solvent (275 mm Hg/rt) gave an oil. 0.63 g, 67%.

Example 25

Preparation of (R,E)-ethyl 3-methoxy-4-(2-(4,4,4-trifluoro-3-methylbutylideneamino)acetamido)benzoate

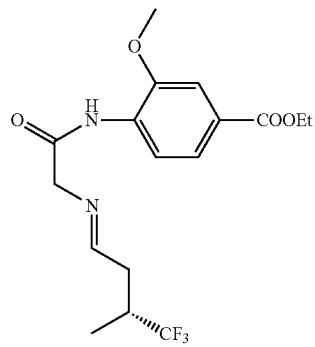

$C_{17}H_{21}F_3N_2O_4$
Mol. Wt.: 374.35

To a stirred suspension of ethyl 4-(2-aminoacetamido)-3-methoxybenzoate HCl salt (500 mg, 1.73 mmol) in MTBE (10 ML) was added triethylamine (210 mg, 2.08 mmol). The mixture was stirred for 30 min. at rt and (R)-4,4,4-trifluoro-3-methylbutanal (340 mg, 2.42 mmol) was added. The new mixture was stirred at rt for 16 hrs. The solid was filtered and washed with MTBE. The filtrate was washed with brine, water and dried with sodium sulfate. Removal of solvent gave a pale yellow oil which solidifies upon standing, 0.71 g, which was directly used for the next step. $^{1}$HNMR (CDCl$_3$, 300 MHz): δ 9.53 (s, br, 1H), 8.50-8.6 (d, 1H, J=8.7 Hz), 7.89 (s, 1H), 7.50-7.75 (d, 1H, J=9.0 Hz), 7.59 (s, 1H), 4.38-4.41 (q, 2H, 7.2 Hz), 4.24 (s, 2H), 3.97 (s, 3H), 2.84-3.0 (m, 1H), 2.70-2.84 (m, 1H), 1.38-1.48 (t, 1H, J=7.2 Hz), 1.25-1.32 (d, 3H, J=6.9 Hz).

Example 26

Preparation of chiral ethyl-4-[[(2'R,3'R,3'S,5'S)-6-chloro-3'-(3-chloro-2-fluoro-phenyl)-2-oxo-5'-[(2R)-3,3,3-trifluoro-2-methyl-propyl]spiro[indoline-2,4'-pyrrolidine]-2'-carbonyl]amino]-3-methoxy-benzoate

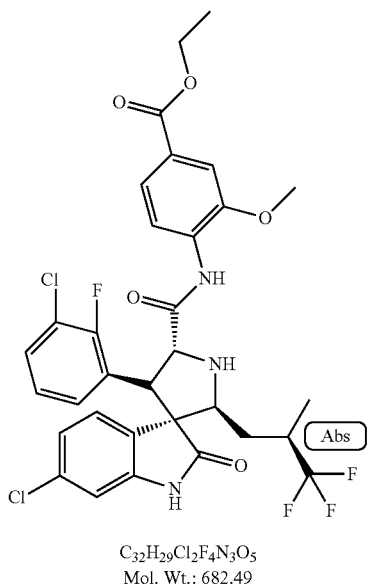

C$_{32}$H$_{29}$Cl$_2$F$_4$N$_3$O$_5$
Mol. Wt.: 682.49

A solution of DBU (Aldrich, 50 mg, 0.33 mmol), (R,E)-ethyl 3-methoxy-4-(2-(4,4,4-trifluoro-3-methylbutylidineamino)acetamido)benzoate (648 mg, 1.73 mmol) and (E)-3-(3-chloro-2-fluorobenzylidene)-6-chloroindolin-2-one (500 mg, 1.63 mmol) (Shu et al, Org. Process Res. Dev. 2013, 17, 247-256) in toluene (10 mL) was stirred at reflux under nitrogen for 24 hr. The reaction mixture was cooled and the solvent was reduced to about 6 mL. Chromatography (30% EtOAc/hexanes) gave two major products. The first component from the column was the mirror image isomer of the desired isomer. 250 mg, 23%. $^1$H NMR (300 MHz, DMSO): δ 10.71 (s, 1H), 10.63 (s, 1H), 8.40-8.50 (d, 1H, J=8.4 Hz), 7.07-7.82 (d, 1H, J=8.1 Hz), 7.59-7.75 (m, 3H), 7.40-7.59 (t, 1H, 7.2 Hz), 7.20-7.30 (t, 1H, J=8.1 Hz), 7.09-7.13 (dd, 1H, J1=8.4 Hz, J2=1.5 Hz), 6.77 (s, 1H), 4.60-4.80 (t, 1H, J=9.6 Hz), 4.40-4.60 (d, 1H, J=9.3 Hz), 4.30-4.40 (q, 2H, J=7.2 Hz), 4.18-4.26 (t, 1H, J=9.3 Hz), 3.90-4.10 (covered, 1H), 4.00 (s, 3H), 2.70-2.90 (m, 1H), 1.65-1.85 (t, 1H, J=11.4 Hz), 1.35-1.40 (t, 3H, J=6.9 Hz), 1.20-1.23 (d, 3H, J=6.6 Hz), 0.87-1.00 (t, 1H, J=11.1 Hz).

The second component from the column was desired product. 220 mg, 20%. $^1$H NMR (300 MHz, DMSO): δ 10.72 (s, 1H), 10.65 (s, 1H), 8.840-8.50 (d, 1H, J=8.4 Hz), 7.74-7.77 (d, 1H, J=8.1 Hz), 7.59-7.75 (m, 3H), 7.40-7.50 (t, 1H, 7.2 Hz), 7.20-7.30 (t, 1H, J=8.1 Hz), 7.09-7.13 (d, 1H, J=8.4 Hz), 6.77 (s, 1H). 4.72-4.80 (t, 1H, J=9.0 Hz), 4.57-4.60 (d, 1H, J=9.3 Hz), 4.30-4.45 (q, 2H, J=6.6 Hz), 4.15-4.26 (t, 1H, J=9.3 Hz), 3.90-4.10 (covered, 1H), 4.00 (s, 3H), 2.30-2.50 (m, 1H), 1.25-1.65 (m, overlapped, 2H), 1.35-1.41 (t, 3H, J=7.2 Hz), 1.26-1.29 (d, 3H, J=6.6 Hz).

Example 27

Preparation of chiral 4-[[(2'R,3R,3'S,5'S)-6-chloro-3'-(3-chloro-2-fluoro-phenyl)-2-oxo-5'-[(2R)-3,3,3-trifluoro-2-methyl-propyl]spiro[indoline-3,4'-pyrrolidine]-2'-carbonyl]amino]-3-methoxy-benzoic acid

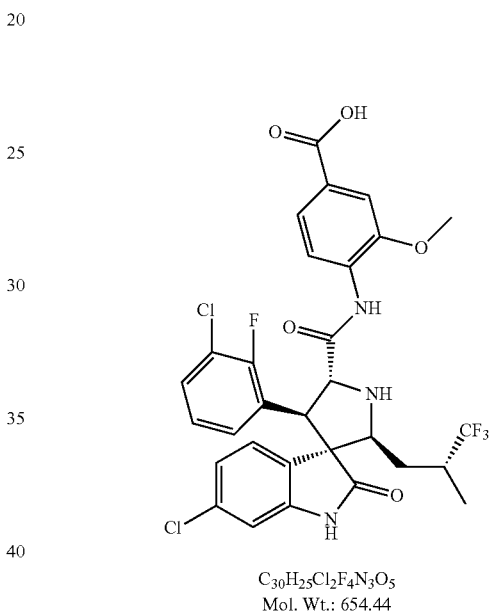

C$_{30}$H$_{25}$Cl$_2$F$_4$N$_3$O$_5$
Mol. Wt.: 654.44

Chiral ethyl 4-[[(2'R,3R,3'S,5'S)-6-chloro-3'-(3-chloro-2-fluoro-phenyl)-2-oxo-5'-[(2R)-3,3,3-trifluoro-2-methyl-propyl]spiro[indoline-3,4'-pyrrolidine]-2'-carbonyl]amino]-3-methoxy-benzoate (200 mg, 0.29 mmol) was dissolved in a mixture of THF (4 mL) and sodium hydroxide solution (75 mg NaOH in 1 mL of water). The new mixture was stirred at 60° C. for 21 hrs under nitrogen. Then an additional 25 mg of NaOH in 0.5 mL of water was added and the mixture was heated and stirred under nitrogen for 24 hrs. 1N HCl was added to make PH=5. The mixture was dried and extracted with EtOAc (3×6 mL) and dried (Na$_2$SO$_4$). Evaporation of solvent gave an off-white solid. 189 mg, 99%. (LC/MS MS(ES+) calculated for C$_{30}$H$_{25}$Cl$_2$F$_4$N$_3$O$_5$ (M+H)$^+$: 654.11, found, 654.12. $^1$HNMR (300 MHz, DMSO): δ 10.64 (s, 1H), 10.61 (s, 1H), 8.36-8.40 (d, 1H, J=9.0 Hz), 7.68-7.71 (d, 1H, J=7.8 Hz), 7.53-7.65 (m, 3H), 7.38-7.42 (t, 1H, 6.9 Hz), 7.16-7.22 (t, 1H, J=8.1 Hz), 7.04-7.08 (dd, 1H, J1=8.4 Hz, J2=1.5 Hz), 6.72 (d, 1H, J=1.8 Hz), 4.67-4.71 (d, 1H, J=9.1 Hz), 4.50-4.54 (d, 1H, J=9.6 Hz), 3.94 (s, 3H), 3.85-4.0 (m, 2H), 2.25-2.50 (m, 1H), 1.40-1.65 (m, 2H), 1.25-1.40 (m, 1H), 1.20-1.23 (d, 3H, J=6.6 Hz).

Example 28

Preparation of chiral (2'R,3R,3'S,5'S)-N-(4-carbamoyl-2-methoxy-phenyl)-6-chloro-3'-(3-chloro-2-fluoro-phenyl)-2-oxo-5'-[(2R)-3,3,3-trifluoro-2-methyl-propyl]spiro[indoline-3,4'-pyrrolidine]-2'-carboxamide

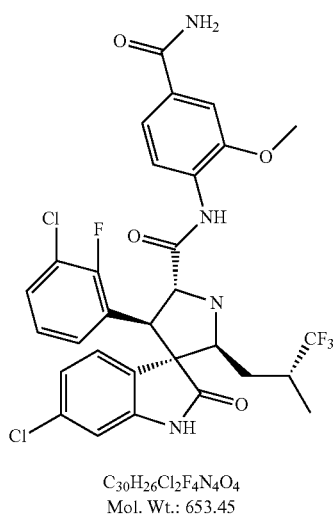 [SMILES: COc1cc(C(N)=O)ccc1NC(=O)[C@@H]1N[C@@H](C[C@@H](C)C(F)(F)F)[C@@]2(C(=O)Nc3cc(Cl)ccc32)[C@H]1c1cccc(Cl)c1F]

C30H26Cl2F4N4O4
Mol. Wt.: 653.45

Chiral 4-[[(2'R,3R,3'S,5'S)-6-chloro-3'-(3-chloro-2-fluoro-phenyl)-2-oxo-5'-[(2R)-3,3,3-trifluoro-2-methyl-propyl]spiro[indoline-3,4'-pyrrolidine]-2'-carbonyl]amino]-3-methoxy-benzoic acid (66 mg, 0.10 mmol) was dissolved in THF (3 mL). To the stirred solution, CDI (Aldrich, 33 mg, 0.20 mmol) was added and the mixture was stirred for 1 hr at rt. Then ammonia (30%, 2 mL) was added and the new mixture was stirred for 15 min. at rt. The mixture was extracted with EtOAc (3×10 mL) and concentrated. Chromatography of the residue (70% EtOAc/Hexanes) gave an off-white solid. 58 mg, 89%. LC/MS MS (ES+) calculated for $C_{30}H_{26}Cl_2F_4N_4O_4$ $(M+H)^+$: 653.13. Found, 653.19. $^1$HNMR (300 MHz, DMSO): δ 10.66 (s, 1H), 10.63 (s, 1H), 8.36-8.40 (d, 1H, J=9.0 Hz), 8.01 (s, br, 1H), 7.74-7.77 (d, 1H, J=8.1 Hz), 7.53-7.63 (m, 2H), 7.56-7.59 (d, 1H, J=8.1 Hz), 7.43-7.49 (t, 1H, 6.9 Hz), 7.38 (s, br, 1H), 7.22-7.28 (t, 1H, J=8.1 Hz), 7.10-7.14 (dd, 1H, J1=8.1 Hz, J2=1.8 Hz), 6.78 (d, 1H, J=1.8 Hz), 4.71-4.78 (dd, 1H, J1=9.9 Hz, J2=9.3 Hz), 4.50-4.54 (d, 1H, J=9.3 Hz), 4.14-4.21 (t, 1H, 10.5 Hz), 3.99 (s, 3H), 3.90-4.02 (m, 1H), 2.35-2.50 (m, 1H), 1.45-1.60 (m, 1H), 1.31-1.45 (m, 1H), 1.26-1.29 (d, 3H, J=6.6 Hz).

Example 29

Preparation of racemic tert-butyl (2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carboxylate

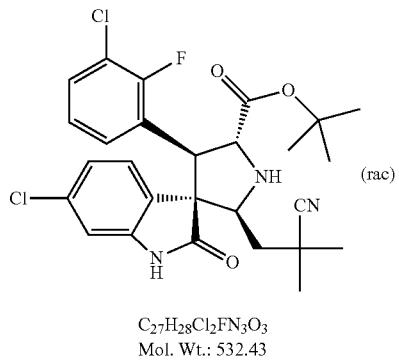 [SMILES: CC(C)(C#N)C[C@@H]1N[C@@H](C(=O)OC(C)(C)C)[C@H](c2cccc(Cl)c2F)[C@]12C(=O)Nc1cc(Cl)ccc12]

C27H28Cl2FN3O3
Mol. Wt.: 532.43

To a stirred solution of tert-butyl 2-[(E)-(3-cyano-3-methyl-butylidene)amino]acetate (20.2 g, 0.065 mol) in THF (800 mL) was added LiOH (0.80 g, 0.033 mol). The mixture was heated to 40° C. until it turned clear. Then a solution of tert-butyl 2-[(E)-(3-cyano-3-methyl-butylidene)aminoacetate (Shu et al, Org. Process Res. Dev. 2013, 17, 247-256; 15.4 g, 0.069 mol) in THF (100 mL) was added in one portion. The resulting mixture was stirred at 40° C. overnight and concentrated. The residue was purified by column chromatography to give 7.3 g of desired product. $^1$H NMR (DMSO, 400 MHz): δ 10.55 (s, 1H), 7.49-7.52 (m, 2H), 7.35-7.39 (t, 1H, J=7.6 Hz), 7.11-7.15 (t, 1H, J=7.6 Hz), 7.03-7.05 (d, 1H, J=6.4 Hz), 6.70 (s, 1H), 4.496 (br, 1H), 4.25-4.28 (d, 1H, 9.6 Hz), 3.88 (t, 1H), 3.28 (s, br, 1H), 1.58-1.65 (dd, 1H, J1=14 Hz, J2=10.8 Hz), 1.35 (s, 3H), 1.19 (s, 9H), 1.18 (s, 3H), 1.06-1.10 (d, 1H, J=14 Hz).

Example 30

Preparation of racemic (2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carboxylic acid

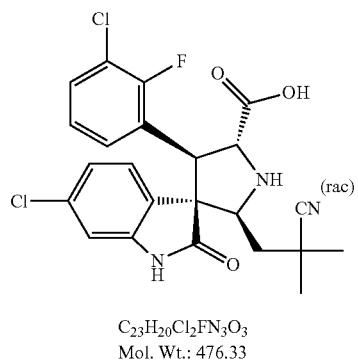 [SMILES: CC(C)(C#N)C[C@@H]1N[C@@H](C(=O)O)[C@H](c2cccc(Cl)c2F)[C@]12C(=O)Nc1cc(Cl)ccc12]

C23H20Cl2FN3O3
Mol. Wt.: 476.33

The mixture of racemic tert-butyl (2'R,3R,3'S,5'S)-6-chloro-3'-(3-chloro-2-fluoro-phenyl)-5'-(2-cyano-2-methylpropyl)-2-oxo-spiro[indoline-3,4'-pyrrolidine]-2'-carboxylate (25 g, 0.047 mmol) was dissolved in 30% THF/CH$_2$Cl$_2$ (70 mL) was stirred at at rt overnight. The solvent was removed and the residue was triturated in methyltert-butyl ether. The mixture was filtered and the filter cake was dried to gave 20 g white solid which was purified by chromatography to give 7.6 g white solid. Yield, 40%. $^1$H NMR (DMSO, 400 MHz): δ 10.61 (s, 1H), 7.56-7.58 (d, 1H, J=8.0 Hz), 7.49-7.53 (t, 1H, J=6.8 Hz), 7.37-7.41 (t, 2H, J=7.8 Hz), 7.13-7.19 (t, 1H, J=8.0 Hz), 7.07-7.09 (dd, 1H, J1=8.0 Hz, J2=2.0 Hz), 6.72 (d, 1H, J=2.0 Hz), 4.59-4.62 (d, 1H, J=10.0 Hz), 4.42-4.45 (d, 1H, J=10 Hz), 4.00-4.62 (d, 1H, J=9.6 Hz), 1.68-1.75 (q, 1H, J1=14.4 Hz, J2=10 Hz), 1.31 (s, 3H), 1.22 (s, 3H), 1.09 (d, 1H, J=14.4 Hz).

Example 31

Preparation of racemic methyl 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]benzoate

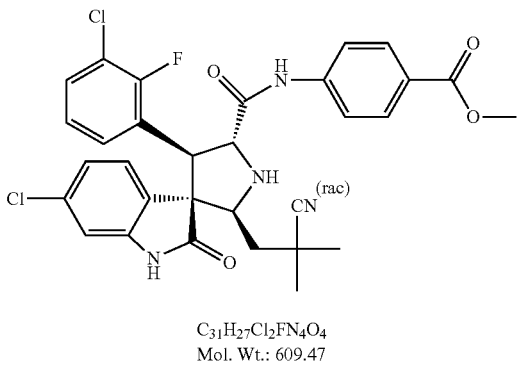 [SMILES: COC(=O)c1ccc(NC(=O)[C@@H]2N[C@@H](CC(C)(C)C#N)[C@@]3(C(=O)Nc4cc(Cl)ccc43)[C@H]2c2cccc(Cl)c2F)cc1]

C$_{31}$H$_{27}$Cl$_2$FN$_4$O$_4$
Mol. Wt.: 609.47

To a solution of (2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carboxylic acid (2.38 g, 5 mmol) in DMF (50 mL) was added HATU (Aldrich, 3.8 g, 10 mmol), DIPEA (Aldrich 2.58 g, 20 mmol) and methyl 4-aminobenzoate (Combi-Blocks, 1.2 g, 8 mmol). The mixture was stirred at rt overnight and the reaction was quenched with water. The mixture was extracted with EtOAc (2×50 mL) and the extract was combined and washed with brine (4×50 mL) and dried with Na$_2$SO$_4$. The solvent was removed and the residue was purified by column chromatography to give a white solid. 180 mg, 5.9%. $^1$H NMR (DMSO, 400 MHz): 610.67 (s, 1H), 10.43 (s, 1H), 7.91-7.94 (d, 2H, J=8.8 Hz), 7.74-7.77 (d, 2H, J=8.4 Hz), 7.66-7.69 (d, 1H, J=7.6 Hz), 7.57-7.61 (t, 1H, J=6.4 Hz), 7.36-7.40 (d, 1H, J=6.4 Hz), 7.15-7.18 (t, 1H, J=8.4 Hz), 7.07-7.08 (dd, 1H, J1=8.4 Hz, J2=1.6 Hz), 6.74 (s, 1H), 4.72-4.75 (t, 1H, J=8.8 Hz), 4.57-4.60 (d, 1H, J=10.0 Hz), 3.98-4.03 (t, 1H, J=9.6 Hz), 3.82 (s, 3H), 3.78 (m, 1H), 1.67-1.74 (dd, 1H, J1=14.0 Hz, J2=10.8 Hz), 1.34 (s, 3H), 1.27 (s, 3H), 1.08-1.12 (d, 1H, J=14.0 Hz).

Example 32

Preparation of racemic 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]benzoic acid

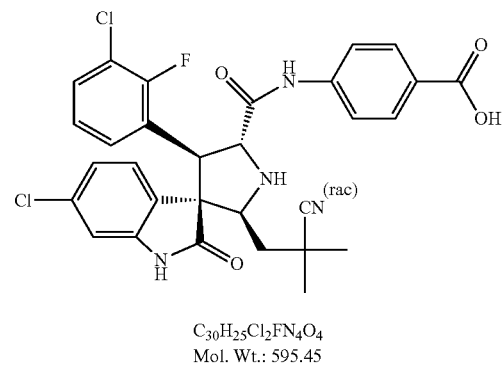 [SMILES: CC(C)(C#N)C[C@@H]1N[C@@H](C(=O)Nc2ccc(C(=O)O)cc2)[C@H](c2cccc(Cl)c2F)[C@]12C(=O)Nc1cc(Cl)ccc12]

C$_{30}$H$_{25}$Cl$_2$FN$_4$O$_4$
Mol. Wt.: 595.45

The solution of methyl 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]benzoate (130 mg, 0.21 mmol) and aqueous NaOH (2N, 0.60 mL) in THF (3 mL) was stirred at 80° C. for 1 hr. The mixture was cooled to rt and concentrated. The residue was treated with 1N HCl until PH reached 3. The mixture was extracted with ethyl acetate and THF. The extract was dried over sodium sulfate and filtered. The filtrate was concentrated to give 100 mg crude which was crystalized with EtOAc/PE to give 80 mg off-white solid. Yield, 64%. LC/MS MS (ES+) calculated for C$_{30}$H$_{25}$Cl$_2$FN$_4$O$_4$ (M–H): 594.12. Found 594. $^1$H NMR (DMSO, 400 MHz): δ 10.52 (s, 1H), 10.32 (s, 1H), 7.86-7.89 (d, 2H, J=8.4 Hz), 7.65-7.70 (m, 3H), 7.54-7.58 (t, 1H, J=6.4 Hz), 7.33-7.38 (t, 1H, J=6.4 Hz), 7.12-7.17 (d, 1H, J=7.2 Hz), 7.03-7.06 (d, 1H, J=9.6 Hz), 6.68 (s, 1H), 4.68-4.72 (d, 1H, J=9.6 Hz), 4.54-4.57 (d, 1H, J=8.8 Hz), 3.97-4.00 (d, 1H, J=9.6 Hz), 1.65-1.72 (q, 1H, J1=12.0 Hz, J2=9.6 Hz), 1.32 (s, 3H), 1.19 (s, 3H), 1.06-1.10 (q, 1H, J=14.0 Hz).

Example 33

Preparation of racemic (2'R,3R,3'S,5'S)-N-(4-carbamoylphenyl)-6-chloro-3'-(3-chloro-2-fluoro-phenyl)-5'-(2-cyano-2-methyl-propyl)-2-oxo-spiro[indoline-3,4'-pyrrolidine]-2'-carboxamide

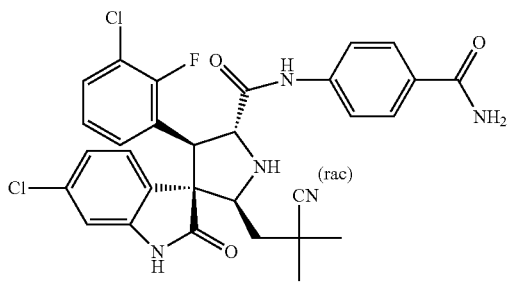

C$_{30}$H$_{26}$Cl$_2$FN$_5$O$_3$
Mol. Wt.: 594.46

To a solution of racemic (2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carboxylic acid (1.42 g, 3 mmol) in DMF (50 mL) was added CDI (Aldrich, 0.97 g, 6 mmol) followed by 4-aminobenzamide (0.41 g, 3 mmol) at 0° C. The mixture was stirred at rt overnight and filtered. The filter cake was dried and the crude product was chromatographed to give an off-white solid. 230 mg, 12.9%. LC/MS MS (ES+) calculated for $C_{30}H_{26}Cl_2FN_5O_3$ (M+H)$^+$: 594.14. Found, 594.18. $^1$H NMR (DMSO, 400 MHz): δ 10.52 (s, 1H), 10.26 (s, 1H), 7.81-7.84 (m, 3H), 7.62-7.69 (m, 3H), 7.54-7.59 (t, 1H, J=7.6 Hz), 7.22-7.38 (t, 1H, J=7.6 Hz), 7.22 (s, br, 1H), 7.13-7.17 (t, 1H, J=7.6 Hz), 7.03-7.06 (d, 1H, J=7.6 Hz), 6.68 (s, 1H), 4.69 (t, 1H, J=8.8 Hz), 4.53-4.56 (d, 1H, J=9.6 Hz), 3.95-4.00 (t, 1H, J=9.6 Hz), 3.76 (br, 1H), 1.66-1.72 (t, 1H, J1=14 Hz, J2=8.4 Hz), 1.32 (s, 3H), 1.19 (s, 3H), 1.06-1.10 (d, 1H, J=14.0 Hz).

Example 34

Preparation of racemic (2'R,3R,3'S,5'S)-6-chloro-3'-(3-chloro-2-fluoro-phenyl)-5'-(2-cyano-2-methyl-propyl)-N-[4-(2-hydroxyethoxy)phenyl]-2-oxo-spiro[indoline-3,4'-pyrrolidine]-2'-carboxamide

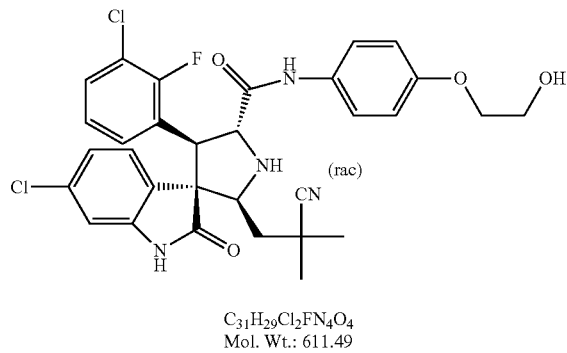 [SMILES: CC(C)(C#N)C[C@@H]1N[C@@H](C(=O)Nc2ccc(OCCO)cc2)[C@H](c2cccc(Cl)c2F)[C@]12C(=O)Nc1cc(Cl)ccc12]

$C_{31}H_{29}Cl_2FN_4O_4$
Mol. Wt.: 611.49

To a stirred solution of racemic (2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carboxylic acid (3.0 g, 6.3 mmol) in DMF (60 mL) was added HATU (Aldrich, 4.8 g, 12.6 mmol), DIPEA (Aldrich, 3.26 g, 25.2 mmol) and 2-(4-aminophenoxy)ethanol (0.91 g, 6 mmol). The mixture was stirred at rt overnight and the reaction was quenched with water. The mixture was extracted with EtOAc (2×50 mL) and the extract was washed with brine (4×50 mL) and dried with $Na_2SO_4$. Removal of solvent gave the crude which was purified by chromatography to give a white solid. 1.2 g, 32.7%. LC/MS MS (ES-F) calculated for $C_{31}H_{29}Cl_2FN_4O_4$ (M+H)$^+$: 611.15. Found 611.30. $^1$H NMR (DMSO, 400 MHz): 10.53 (s, 1H), 9.97 (s, 1H), 7.66-7.69 (d, 1H, J=8.8 Hz), 7.59-7.61 (t, 1H, J=6.4 Hz), 7.49-7.52 (d, 2H, J=8.4 Hz), 7.35-7.39 (t, 1H, J=7.2 Hz), 7.14-7.19 (t, 1H, J=7.6 Hz), 7.05-7.08 (d, 1H, J=8.4 Hz), 6.88-6.90 (d, 2H, J=8.8 Hz), 6.70 (s, 1H), 4.82-4.85 (t, 1H, J=5.2 Hz), 4.63-4.69 (t, 1H, J=9.6 Hz), 4.51-4.54 (d, 1H, J=9.6 Hz), 3.92-4.00 (m, 3H), 3.66-3.77 (m, 3H), 1.67-1.74 (dd, 1H, J1=13.6 Hz, J2=10.4 Hz), 1.34 (s, 3H), 1.22 (s, 3H), 1.10 (d, 1H, J=13.6 Hz).

Example 35

Preparation of racemic methyl 5-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]thiophene-2-carboxylate

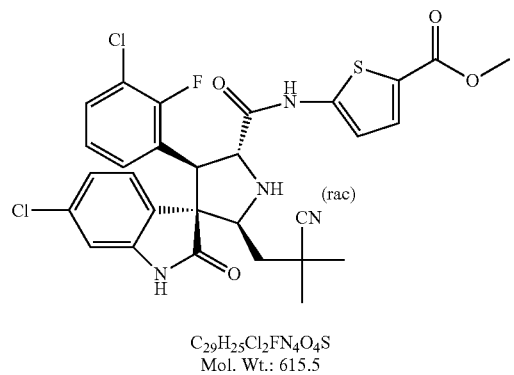 [SMILES: COC(=O)c1ccc(NC(=O)[C@@H]2N[C@@H](CC(C)(C)C#N)[C@@]3(C(=O)Nc4cc(Cl)ccc43)[C@H]2c2cccc(Cl)c2F)s1]

$C_{29}H_{25}Cl_2FN_4O_4S$
Mol. Wt.: 615.5

To a stirred solution of racemic (2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carboxylic acid (3.0 g, 6.3 mmol) in DMF (45 mL) was added HATU (Aldrich, 4.47 g, 11.8 mmol), DIPEA (Aldrich, 3.26 g, 25.2 mmol) and 2-(4aminophenoxy)ethanol (0.91 g, 6 mmol). The mixture was stirred at rt overnight and the reaction was quenched with water. The mixture was extracted with EtOAc (2×50 mL) and the extract was washed with brine (4×50 mL), dried over $Na_2SO_4$ and concentrated. The residue was purified by chromatography to give a white solid. 310 mg, 8.7%. $^1$H NMR (DMSO, 400 MHz): δ 11.33 (s, 1H), 10.51 (s, 1H), 7.52-7.63 (m, 3H), 7.32-7.36 (t, 1H, J=7.6 Hz), 7.11-7.15 (t, 1H, J=8.8 Hz), 7.02-7.05 (d, 1H, J=8.8 Hz), 7.11-7.14 (m, 1H), 6.76-6.78 (d, 1H, J=4 Hz), 6.68 (s, 1H), 4.76-4.81 (t, 1H, J=10 Hz), 4.54-4.57 (d, 1H, J=8.8 Hz), 3.93-3.98 (t, 1H, J=10.8 Hz), 3.73 (s, 3H), 3.60-3.71 (t, 1H, J=10.8 Hz), 1.63-1.69 (dd, 1H, J1=14.0 Hz, J2=10.0 Hz)), 1.31 (s, 3H), 1.19 (s, 3H), 1.08-1.15 (d, 1H, J=14.4 Hz).

Example 36

Preparation of racemic 5-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]thiophene-2-carboxylic acid

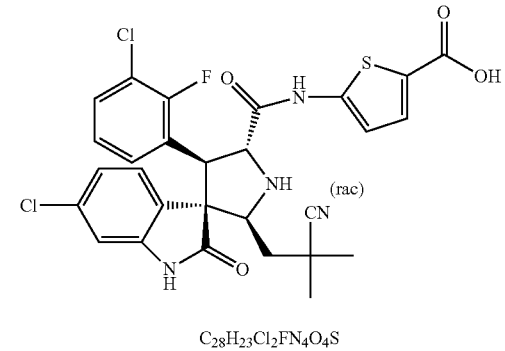

$C_{28}H_{23}Cl_2FN_4O_4S$
Mol. Wt.: 601.48

The solution of methyl 5-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]thiophene-2-carboxylate (150 mg, 0.24 mmol) and NaOH (2N, 0.72 mmol) in THF (3 mL) and MeOH (1 mL) was stirred at 80° C. for 1 hr. The mixture was cooled to rt and concentrated. The residue was treated with 1N HCl until PH reached 3. The mixture was extracted with EtOAc and THF (3:1) and the extract was dried over Na$_2$SO$_4$ and concentrated. The residue was chromatographed to give a white solid. 70 mg, 48.5%. $^1$H NMR (DMSO, 400 MHz): δ 11.13 (s, 1H), 7.57-7.64 (m, 2H), 7.34-7.39 (t, 1H, J=6.4 z), 7.13-7.18 (t, 1H, J=8.4 Hz), 7.00-7.06 (m, 2H), 6.86 (s, 1H), 6.57-6.59 (d, 1H, J=3.2 Hz), 4.76-4.80 (d, 1H, J=9.2 Hz), 4.54-4.57 (d, 1H, J=10.4 Hz), 3.93-3.97 (d, 1H, J=9.6 Hz), 1.65-1.72 (dd, 1H, J1=14.0 Hz, J2=10.8 Hz),1.33 (s, 3H), 1.12 (s, 3H), 1.08-1.12 (d, 1H, J=14.0 Hz).

Example 37

Preparation of racemic (2'R,3R,3'S,5'S)-N-(5-carbamoyl-2-thienyl)-6-chloro-3'-(3-chloro-2-fluoro-phenyl)-5'-(2-cyano-2-methyl-propyl)-2-oxo-spiro[indoline-3,4'-pyrrolidine]-2'-carboxamide

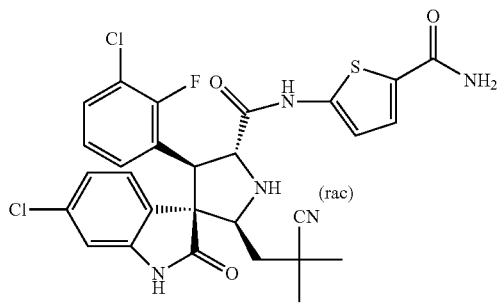

C$_{28}$H$_{24}$Cl$_2$FN$_5$O$_3$S
Mol. Wt.: 600.49

To a stirred solution of 5-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]thiophene-2-carboxylic acid (130 mg, 0.21 mmol) in THF (20 mL) was added CDI (Aldrich, 169 mmol, 1.1 mmol) at 5° C. The mixture was stirred at 35° C. for 6 hr before ammonium hydroxide (28%, 300 mg) was added. The mixture was further stirred overnight and treated with EtOAc (10 mL) and water. The organic layer was separated and dried over Na$_2$SO$_4$ and concentrated. The residue was purified by chromatography to give a white solid. 60 mg, 46%. $^1$H NMR (DMSO, 400 MHz): δ 11.20 (s, 1H), 10.59 (s, 1H), 7.76 (br, 1H), 7.64-7.67 (d, 1H, J=8.8 Hz), 7.51-7.59 (m, 2H), 7.37-7.41 (t, 1H, J=7.6 Hz), 7.15-7.20 (t, 1H, J=7.6 Hz), 7.07-7.10 (d, 1H, J=7.2 Hz), 6.72 (s, 1H), 4.81 (m, 1H), 4.56-4.59 (d, 1H, J=8.4 Hz), 3.99 (m, 1H), 3.70 (m, 1H), 1.66-1.72 (m, 1H), 1.34 (s, 3H), 1.21 (s, 3H), 1.12-1.16 (d, 1H, J=13.6 Hz).

Example 38

Preparation of racemic methyl 5-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]pyridine-2-carboxylate

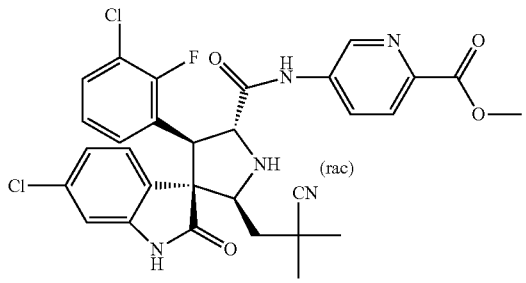

C$_{30}$H$_{26}$Cl$_2$FN$_5$O$_4$
Mol. Wt.: 610.46

To a stirred solution of racemic (2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carboxylic acid (2.38 g, 5.9 mmol) in DMF (45 mL) was added HATU (Aldrich, 3.80 g, 10.00 mmol), DIPEA (Aldrich, 2.58 g, 20 mmol) and methyl 5-amino-2-pyridinecarboxylate (0.72 g, 4.8 mmol). The mixture was stirred at rt overnight and the reaction was quenched with water. The mixture was extracted with EtOAc (2×100 mL) and the extract was washed with brine (4×100 mL), dried over Na$_2$SO$_4$ and concentrated. The residue was purified by chromatography to give a white solid. 200 mg, 7.0%. $^1$H NMR (DMSO, 400 MHz): δ 10.52-10.54 (d, 1H, J=3.6 Hz), 8.82-8.26 (d, 1H, J=2.4 Hz), 8.22-8.26 (dd, 1H, J1=8.4 Hz, J2=2.0 Hz), 8.02-8.05 (d, 1H, J=8.8 Hz), 7.64-7.66 (d, 1H, J=8.4 Hz), 7.54-7.58 (t, 1H, J=6.4 Hz), 7.36-7.38 (t, 1H, J=7.6 Hz), 7.13-7.18 (t, 1H, J=7.6 Hz), 7.04-7.07 (d, 1H, J=8.4 Hz), 6.68 (s, 1H), 4.71-4.77 (t, 1H, J=9.6 Hz), 4.56-4.59 (d, 1H, J=10.0 Hz), 3.96-4.02 (t, 1H, J=10.8 Hz), 3.82 (s, 3H), 3.75-3.82 (m, 1H), 1.65-1.72 (dd, 1H, J1=14.0 Hz, J2=9.6 Hz),1.31 (s, 3H), 1.19 (s, 3H), 1.07-1.11 (d, 1H, J=13.6 Hz).

Example 39

Preparation of racemic 5-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]pyridine-2-carboxylic acid

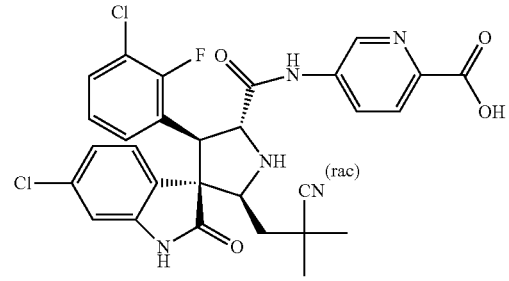

C$_{29}$H$_{24}$Cl$_2$FN$_5$O$_4$
Mol. Wt.: 596.44

The solution of methyl 5-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]pyridine-2-carboxylate (200 mg, 0.33 mmol) and NaOH (2N, 1 mL) in THF (4 mL) and MeOH (0.70 mL) was stirred at 80° C. for 1 hr. The mixture was cooled to rt and 1N HCl was added to make PH=3. The solid was filtered and dried and recrystallized from DCM/MeOH to give a white solid. 120 mg, 62%. $^1$H NMR (DMSO, 400 MHz): δ 10.52 (d, 2H), 8.82 (d, 1H, J=2.4 Hz), 8.22-8.25 (dd, 1H, J1=8.4 Hz, J2=2.0 Hz), 8.02-8.05 (d, 1H, J=8.8 Hz), 7.64-7.66 (d, 1H, J=8.4 Hz), 7.54-7.58 (t, 1H, J=6.4 Hz), 7.34-7.38 (t, 1H, J=7.2 Hz), 7.06-7.15 (t, 1H, J=8.4 Hz), 7.04-7.05 (d, 1H, J=8.8 Hz), 6.68 (s, 1H), 4.71-4.77 (t, 1H, J=9.6 Hz), 4.56-4.59 (d, 1H, J=10.0 Hz), 3.96-4.02 (t, 1H, J=10.8 Hz), 1.65-1.72 (dd, 1H, J1=14.0 Hz, J2=9.6 Hz), 1.32 (s, 3H), 1.18 (s, 3H), 1.07-1.11 (d, 1H, J=13.6 Hz).

Example 40

Preparation of 4-[2-(3-cyano-3,3-dimethyl-propylideneamino)-acetylamino]-3-methoxy-benzoic acid methyl ester

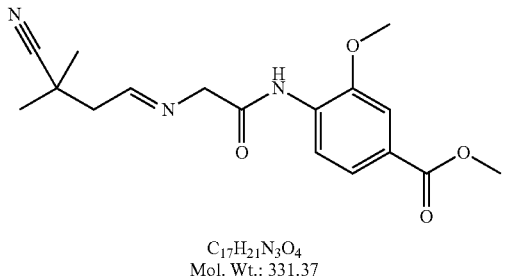 [SMILES: COC(=O)c1ccc(NC(=O)C/N=C/CC(C)(C)C#N)c(OC)c1]

C$_{17}$H$_{21}$N$_3$O$_4$
Mol. Wt.: 331.37

A mixture of 4-(2-amino-acetylamino)-3-methoxy-benzoic acid methyl ester (15.0 g, 0.047 mol), 2,2-dimethyl-4-oxo-butyronitrile (Combi-blocks, 4.7 g, 0.042 mol) and Et$_3$N (14.3 g, 0.141 mol) in DCM (300 mL) was refluxed for 3 hr. The reaction mixture was concentrated and the residue was chromatographed (EtOAc/Hexane, 2:1) to give 9.5 g white solid (yield: 61.0%). $^1$H NMR (CDCl$_3$, 400 MHz) δ 9.43 (s, 1H), 8.52-8.54 (d, 1H), 7.92-7.94 (q, 1H), 7.70-7.73 (q, 1H), 7.57-7.58 (d, 1H), 4.30 (s, 2H), 3.97 (s, 3H), 3.93 (s, 3H), 2.63-2.65 (d, 2H), 1.50 (s, 6H).

Example 41

Preparation of racemic methyl 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]-3-methoxy-benzoate

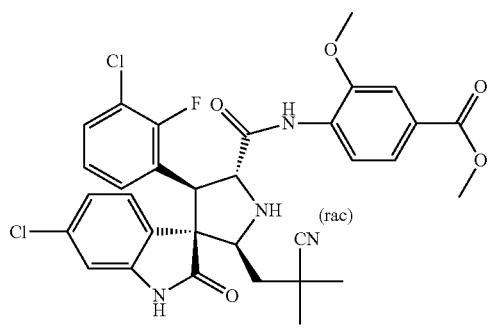

C$_{32}$H$_{29}$Cl$_2$FN$_4$O$_5$
Mol. Wt.: 639.5

A solution of DBU (Aldrich, 0.53 g, 3.49 mmol), 4-[2-(3-cyano-3,3-dimethyl-propylideneamino)-acetylamino]-3-methoxy-benzoic acid methyl ester (6.0 g, 18 mmol) and (E)-3-(3-chloro-2-fluorobenzylidene)-6-chloroindolin-2-one (5.25 g, 17 mmol) (Shu et al, Org. Process Res. Dev. 2013, 17, 247-256) in toluene (60 mL) was stirred at gentle reflux under N$_2$ overnight. The mixture was cooled to rt and concentrated. The residue was chromatographed (DCM/MeOH) to give a white solid. 2.20 g, 20%. LC/MS MS (ES+) calculated for C$_{32}$H$_{29}$Cl$_2$FN$_4$O$_5$ (M+H)$^+$: 639.3. $^1$H NMR (DMSO, 400 MHz): δ 10.68 (s, 1H), 10.54 (s, 1H), 8.41-8.43 (d, 1H, J=8.4 Hz), 7.72-7.74 (d, 1H, J=8.0 Hz), 7.57-7.63 (m, 3H), 7.37-7.41 (t, 1H, J=7.2 Hz), 7.16-7.20 (t, 1H, J=7.6 Hz), 7.03-7.06 (dd, 1H, J1=8.0 Hz, J2=2.0 Hz), 6.69-6.70 (d, 1H, J=1.6 Hz), 4.71-4.76 (t, 1H, J=9.2 Hz), 4.56-4.58 (d, 1H, J=9.2 Hz), 3.90-3.99 (m, 4H), 3.85 (s, 3H), 1.68-1.74 (dd, 1H, J1=14 Hz, J2=10 Hz), 1.45 (s, 3H), 1.35 (s, 3H), 1.17-1.24 (d, 1H, J=14 Hz).

Example 42

Preparation of racemic 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]-3-methoxy-benzoic acid

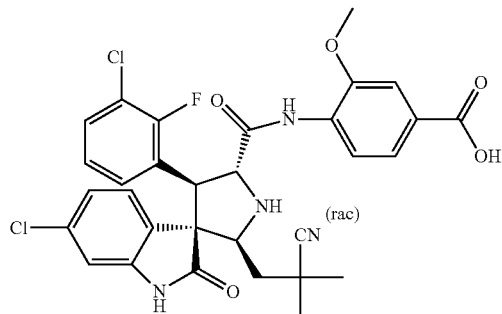

C$_{31}$H$_{27}$Cl$_2$FN$_4$O$_5$
Mol. Wt.: 625.47

To a stirred solution of racemic methyl 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]-3-methoxy-benzoate (256 mg, 0.40 mmol) in THF (1.5 mL) and MeOH (0.5 mL) was added NaOH (2M, 1.2 mL) at 0° C. The mixture was stirred at 80° C. for 1 hr, cooled to rt and concentrated. The residue was diluted with water and the mixture was treated with 1N HCl to PH=4. The solid was filtered and dried. Purification by column chromatography gave a white solid. 215 mg, 86%. LC/MS MS (ES+) calculated for C$_{31}$H$_{27}$Cl$_2$FN$_4$O$_5$ (M+H)$^+$: 625.13. Found, 625.9. $^1$H NMR (DMSO, 400 MHz): δ 10.66 (s, 1H), 10.57 (s, 1H), 8.38-8.40 (d, 1H, J=8.8 Hz), 7.72-7.74 (d, 1H, J=8.8 Hz), 7.57-7.63 (m, 3H), 7.37-7.41 (m, 1H), 7.16-7.20 (t, 1H, J=8.0 Hz), 7.04-7.06 (dd, 1H, J1=8.0 Hz, J2=2.0 Hz), 6.69-6.70 (d, 1H, J=2.0 Hz), 4.71-4.75 (t, 1H, J=9.2 Hz), 4.55-4.57 (d, 1H, J=9.2 Hz), 3.94-3.99 (m, 5H), 1.67-1.74 (dd, 1H, J1=14.0 Hz, J2=10.0 Hz), 1.45 (s, 3H), 1.34 (s, 3H), 1.16-1.20 (d, 1H, J=14.0 Hz).

Example 43

Preparation of racemic (2'R,3R,3'S,5'S)-N-(4-carbamoyl-2-methoxy-phenyl)-6-chloro-3'-(3-chloro-2-fluoro-phenyl)-5'-(2-cyano-2-methyl-propyl)-2-oxo-spiro[indoline-3,4'-pyrrolidine]-2'-carboxamide

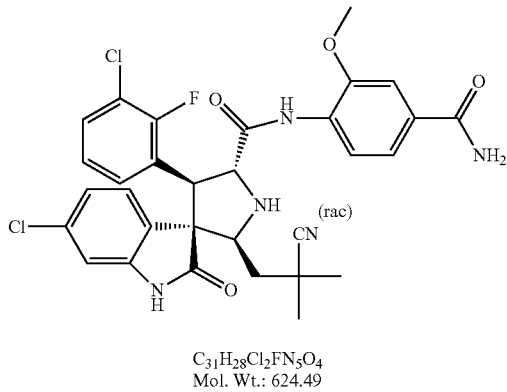 [SMILES: COc1cc(C(N)=O)ccc1NC(=O)[C@@H]1N[C@@H](CC(C)(C)C#N)[C@@]2(C(=O)Nc3cc(Cl)ccc32)[C@H]1c1cccc(Cl)c1F]

$C_{31}H_{28}Cl_2FN_5O_4$
Mol. Wt.: 624.49

To a stirred solution of racemic 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]-3-methoxy-benzoic acid (90 mg, 0.14 mmol) in THF (1 mL) was added CDI (Aldrich, 46.7 mg, 0.28 mmol). The mixture was stirred at rt for 1.5 hr and ammonia (28%, 190 mg, 2.80 mmol) was added. The mixture was stirred at rt overnight and extracted with EtOAc. The extract was washed with 1 N HCl, brine and water. It was dried over sodium sulfate and concentrated. The residue was purified by chromatography to give a solid. 80 mg, 92%. LC/MS MS (ES+) calculated for $C_{31}H_{28}Cl_2FN_5O_4$ (M+H)$^+$: 624.15. Found, 624.19. $^1$H NMR (DMSO, 400 MHz): δ 10.59 (s, 1H), 10.55 (s, 1H), 8.32-8.34 (d, 1H, J=8.8 Hz), 7.93 (s, 1H), 7.71-7.74 (d, 1H, J=8.0 Hz), 7.58-7.63 (m, 2H), 7.50-7.52 (d, 1H, J=8.4 Hz), 7.37-7.41 (t, 1H, J=7.2 Hz), 7.29 (s, 1H), 7.16-7.20 (t, 1H, J=8.0 Hz), 7.04-7.06 (dd, 1H, J1=8.0 Hz, J2=2.0 Hz), 6.70 (s, 1H), 4.70-4.72 (t, 1H, J=9.2 Hz), 4.54-4.56 (d, 1H, J=9.6 Hz), 3.93-3.98 (m, 5H), 1.70-1.71 (dd, 1H, J1=14.0 Hz. J2=10 Hz), 1.45 (s, 3H), 1.35 (s, 3H), 1.16-1.24 (d, 1H, J=14.0 Hz).

Example 44

Preparation of chiral 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]-3-methoxy-benzoic acid

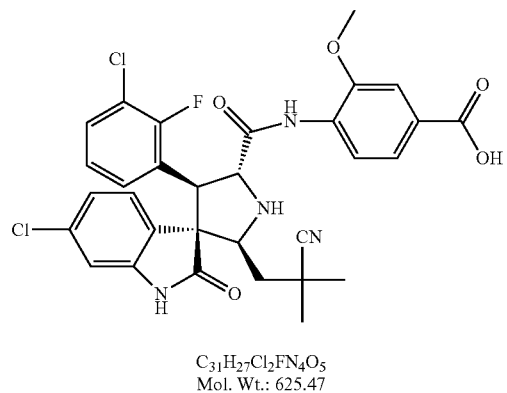 [SMILES: COc1cc(C(=O)O)ccc1NC(=O)[C@@H]1N[C@@H](CC(C)(C)C#N)[C@@]2(C(=O)Nc3cc(Cl)ccc32)[C@H]1c1cccc(Cl)c1F]

$C_{31}H_{27}Cl_2FN_4O_5$
Mol. Wt.: 625.47

Racemic 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]-3-methoxy-benzoic acid (100 mg) was separated by SFC to give the two enantiomers. Peak 1 (30 mg), peak 2 (23 mg).

Example 45

Preparation of methyl 4-[[2-(tert-butoxycarbonylamino)acetyl]amino]-3-fluoro-benzoate

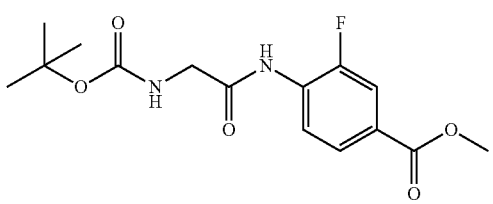

$C_{15}H_{19}FN_2O_5$
Mol. Wt.: 326.32

To a stirred solution of glycine tert-butylester (Aldrich, 26.1 g, 0.15 mol) in DMF (400 mL) was added HATU (Aldrich, 85 g, 0.22 mol), DIPEA (Aldrich, 96.3 g, 0.74 mol) and methyl 4-amino-3-fluorobenzoate (Combi-blocks, 22 g, 01.13 mol). The mixture was stirred at 70° C. overnight and then cooled to rt and partioned between EtOAc (2×500 mL) and water. The organic layer was washed with brine and dried over sodium sulfate and concentrated. The residue was chromatographed (EtOAc/Hexane, 5:1) to give a white solid. 18.7 g, 43%. $^1$H NMR (CDCl$_3$, 400 MHz): δ 8.63 (s, 1H), 8.40-8.44 (t, 1H, J=8.4 Hz), 7.79-7.81 (t, 1H, J=8.8 Hz), 7.71-7.74 (dd, 1H, J1=11.6 Hz, J2=1.6 Hz), 5.33 (s, 1H), 3.95-3.97 (d, 2H, J=6.4 Hz), 3.88 (s, 3H), 1.46 (s, 9H).

Example 46

Preparation of methyl 4-[(2-aminoacetyl)amino]-3-fluoro-benzoate 2,2,2-trifluoroacetic acid salt

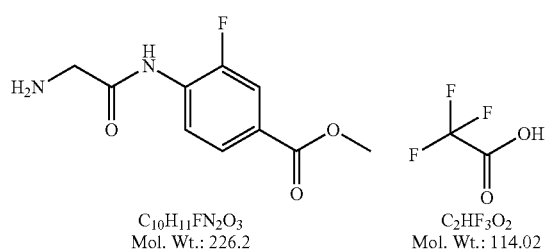

$C_{10}H_{11}FN_2O_3$          $C_2HF_3O_2$
Mol. Wt.: 226.2          Mol. Wt.: 114.02

To a stirred solution of methyl 4-[[2-(tert-butoxycarbonylamino)acetyl]amino]-3-fluoro-benzoate (18.7 g, 0.057 mol) in DCM (90 mL) was added TFA (30 mL) at 0° C. The mixture was stirred at rt overnight and concentrated to give 18.8 g off-white solid. Yield, 97%. The salt was directly used for the next step.

Example 47

Preparation of methyl 4-[[2-[(E)-(3-cyano-3-methyl-butylidene)amino]acetyl]amino]-3-fluoro-benzoate

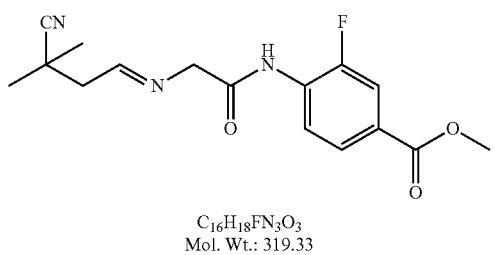 [SMILES: COC(=O)c1ccc(NC(=O)C/N=C/CC(C)(C)C#N)c(F)c1]

C₁₆H₁₈FN₃O₃
Mol. Wt.: 319.33

A mixture of methyl 4-[(2-aminoacetyl)amino]-3-fluoro-benzoate 2,2,2-trifluoroacetic acid salt (18.8 g, 57 mmol), 2,2-dimethyl-4-oxobutanenitrile (Combi-blocks, 7.6 g, 68 mmol) and Et₃N (23.1 g, 0.23 mol) in DCM (150 mL) was refluxed overnight, The reaction mixture was quickly washed with water, dried with sodium sulfate and concentrated to give an oil (18 g) which was directly used for the next step without further purification.

Example 48

Preparation of racemic methyl 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]-3-fluoro-benzoate

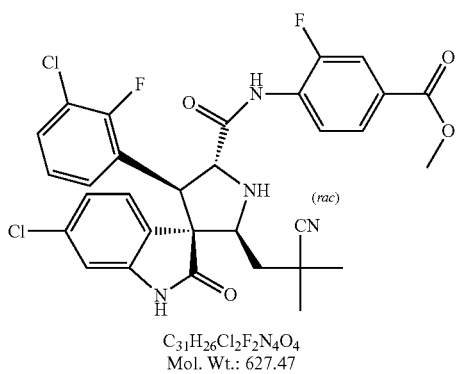 [SMILES: COC(=O)c1ccc(NC(=O)[C@@H]2N[C@@H](CC(C)(C)C#N)[C@@]3(C(=O)Nc4cc(Cl)ccc43)[C@H]2c2cccc(Cl)c2F)c(F)c1]

C₃₁H₂₆Cl₂F₂N₄O₄
Mol. Wt.: 627.47

A solution of DBU (Aldrich, 1.54 g, 10.1 mmol), 4-[2-(3-cyano-3,3-dimethyl-propylideneamino)-acetylamino]-3-fluoro-benzoic acid methyl ester (17.5 g, 55 mmol) and (E)-3-(3-chloro-2-fluorobenzylidene)-6-chloroindolin-2-one (15.2 g, 49 mmol) (Shu et al, *Org. Process Res. Dev.* 2013, 17, 247-256) in toluene (400 mL) was stirred at gentle reflux under N₂ overnight. The mixture was cooled to rt and concentrated. The residue was chromatographed (DCM/MeOH) to give a white solid. 8.7 g, 28%. ¹HNMR (DMSO, 400 MHz) δ 10.53 (s, 1H), 10.48 (s, 1H), 8.40-8.44 (t, 1H, J=7.6 Hz), 7.77-7.81 (m, 2H), 7.66-7.68 (d, 1H, J=8.0 Hz), 7.55-7.59 (t, 1H, J=6.8 Hz), 7.34-7.38 (m, 1H), 7.13-7.17 (t, 1H, J=8.0 Hz), 7.01-7.05 (dd, 1H, J1=8.0 Hz, J2=2.0 Hz), 6.67-6.68 (d, 1H, J=2.4 Hz), 4.73-4.78 (t, 1H, J=9.2 Hz), 4.58-4.60 (d, 1H, J=9.6 Hz), 3.91-3.96 (m, 1H), 3.82 (s, 3H), 1.65-1.71 (dd, 1H, J1=14 Hz, J2=10.0 Hz), 1.35 (s, 3H), 1.26 (s, 3H), 1.12 (d, 1H, J=14 Hz).

Example 49

Preparation of racemic 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]-3-fluoro-benzoic acid

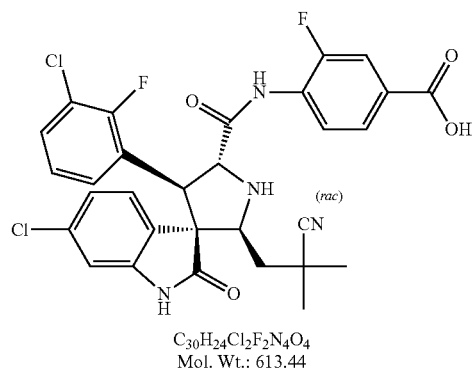 [SMILES: CC(C)(C#N)C[C@@H]1N[C@@H](C(=O)Nc2ccc(C(=O)O)cc2F)[C@H](c2cccc(Cl)c2F)[C@]12C(=O)Nc1cc(Cl)ccc12]

C₃₀H₂₄Cl₂F₂N₄O₄
Mol. Wt.: 613.44

To a stirred solution of methyl 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]-3-fluoro-benzoate (2.5 g, 4 mmol) in THF (60 mL) was added LiOH (0.38 g in 20 mL water). The mixture was stirred at 40° C. overnight, cooled to rt and treated with 1 N HCl to PH equals 2. The solid was filtered and the cake was dried to give the crude (1.7 g) which was purified by column chromatography to a white solid. 550 mg, 95%. ¹HNMR (DMSO, 400 MHz): δ 10.57 (s, 1H), 10.49 (s, 1H), 8.40-8.44 (t, 1H, J=8.0 Hz), 7.78-7.81 (m, 2H), 7.70-7.72 (d, 1H, J=8.0 Hz), 7.59-7.62 (t, 1H, J=7.2 Hz), 7.38-7.41 (t, 1H, J=7.2 Hz), 7.17-7.20 (t, 1H, J=8.0 Hz), 7.06-7.09 (dd, 1H, J1=8.0 Hz, J2=1.6 Hz), 6.71 (s, 1H), 4.77-4.79 (d, 1H, J=9.2 Hz), 4.60-4.63 (d, 1H, J=9.6 Hz), 4.04-4.07 (d, 1H, J=9.6 Hz), 1.68-1.74 (dd, 1H, J1=14 Hz, J2=10.0 Hz), 1.38 (s, 3H), 1.29 (s, 3H), 1.15-1.23 (d, 1H, J=14.0 Hz).

Example 50

Preparation of methyl 4-[[2-(tert-butoxycarbonylamino)acetyl]amino]-3-chloro-benzoate

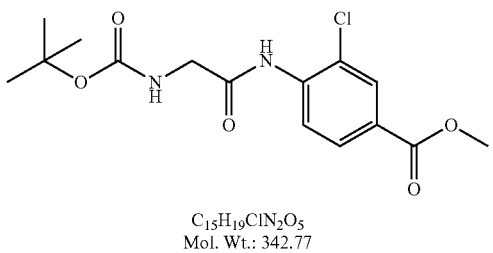

C₁₅H₁₉ClN₂O₅
Mol. Wt.: 342.77

To a stirred solution of glycine tert-butylester (Aldrich, 17.0 g, 0.096 mol) in DMF (350 mL) was added HATU (Aldrich, 65.7 g, 0.17 mol), DIPEA (Aldrich, 62 g, 0.48 mol) and methyl 4-amino-3-chlororobenzoate (Combi-blocks, 17 g, 0.091 mol). The mixture was stirred at 80° C. overnight and then cooled to rt and partioned between EtOAc (2×500 mL) and water (1000 mL). The organic layer was washed with brine and dried over sodium sulfate and concentrated. The residue was chromatographed (EtOAc/Hexane, 5:1) to give a white solid. 4.5 g, 35%. ¹H NMR (CDCl₃, 400 MHz): δ 8.77 (s, 1H), 8.51-8.53 (d, 1H, J=9.2 Hz), 8.04 (s, 1H), 7.91-7.94 (d, 1H, J=9.2 Hz), 5.22 (s, br, 1H), 3.96-3.98 (d, 2H, J=6.4 Hz), 3.88 (s, 3H), 1.43 (s, 9H).

Example 51

Preparation of methyl 4-[(2-aminoacetyl)amino]-3-fluoro-benzoate 2,2,2-trifluoroacetic acid salt

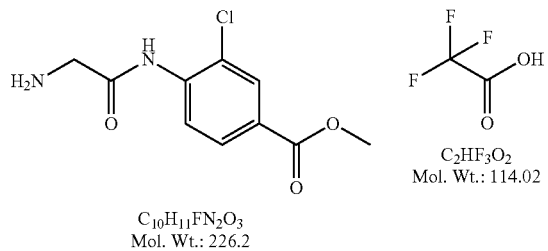 [SMILES: COC(=O)c1ccc(NC(=O)CN)c(Cl)c1 ; O=C(O)C(F)(F)F]

To a stirred solution of methyl 4-[[2-(tert-butoxycarbonylamino)acetyl]amino]-3-chloro-benzoate (9.5 g, 0.0277 mol) in DCM (50 mL) was added TFA (15 mL) at 0° C. The mixture was stirred at rt overnight and concentrated to give 9.0 g off-white solid. Yield, 91%. The salt was directly used for the next step. ¹HNMR (DMSO, 400 MHz): δ 8.47 (d, 1H, J=8.4 Hz), 7.91 (d, 1H, J=1.6 Hz), 7.86 (dd, 1H, J1=8.4 Hz, J2=1.6 Hz), 4.70 S, 1H), 3.80 (s, 3H), 3.34 (s, 2H).

Example 52

Preparation of methyl 4-[[2-[(E)-(3-cyano-3-methyl-butylidene)amino]acetyl]amino]-3-chloro-benzoate

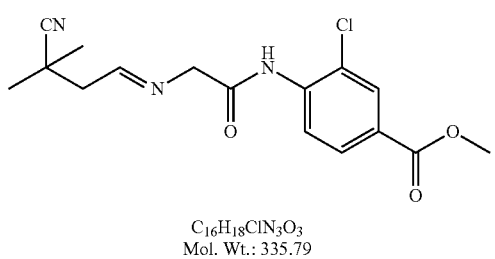

A mixture of methyl 4-[(2-aminoacetyl)amino]-3-chloro-benzoate 2,2,2-trifluoroacetic acid salt (9.0 g, 25 mmol), 2,2-dimethyl-4-oxobutanenitrile (Combi-blocks, 3.33 g, 30 mmol) and Et₃N (12.8, 130 mmol) in DCM (150 mL) was refluxed overnight, The reaction mixture was quickly washed with water, dried with sodium sulfate and concentrated to give an oil (8.0 g) which was directly used for the next step without further purification.

Example 53

Preparation of racemic methyl 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]-3-fluoro-benzoate

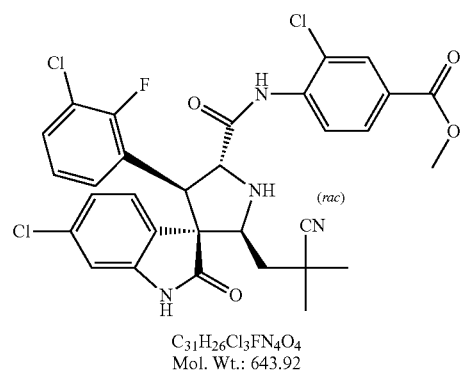 [SMILES: COC(=O)c1ccc(NC(=O)[C@@H]2N[C@@H](CC(C)(C)C#N)[C@@]3(C(=O)Nc4cc(Cl)ccc43)[C@H]2c2cccc(Cl)c2F)c(Cl)c1]

A solution of DBU (Aldrich, 0.62 g, 4 mmol), 4-[2-(3-cyano-3,3-dimethyl-propylideneamino)-acetylamino]-3-chloro-benzoic acid methyl ester (6.11 g, 20 mmol) and (E)-3-(3-chloro-2-fluorobenzylidene)-6-chloroindolin-2-one (6.11 g, 20 mmol) (Shu et al, Org. Process Res. Dev. 2013, 17, 247-256) in toluene (120 mL) was stirred at gentle reflux under N₂ for 4.5 hr. The mixture was cooled to rt and concentrated. The residue was treated with MeOH (120 mL) to give a light yellow solid, which was recrystallized from EtOAc/PE to give 3.4 g solid (27%). ¹HNMR (DMSO, 400 MHz) δ 10.77 (s, 1H), 10.53 (s, 1H), 8.53-8.55 (d, 1H, J=8.8 Hz), 8.02-8.03 (d, 1H, J=2.0 Hz), 7.89-7.91 (dd, 1H, J1=8.8 Hz, J2=1.6 Hz), 7.68-7.70 (d, 1H, J=8.0 Hz), 7.56-7.59 (t, 1H, J=6.8 Hz), 7.34-7.38 (t, 1H, J=7.6 Hz), 7.14-7.18 (t, 1H, J=8.0 Hz), 7.02-7.05 (dd, 1H, J1=8.0 Hz, J2=2.0 Hz), 6.66-6.67 (d, 1H, J=2.0 Hz), 4.76-4.81 (t, 1H, J=10 Hz), 4.59-4.62 (d, 1H, J=10.0 Hz), 4.60 (t, 1H, J=10.0 Hz), 4.04-4.10 (m, 1H), 3.82 (s, 3H), 1.68-1.73 (dd, 1H, J1=14.4 Hz, J2=10 Hz)), 1.37 (s, 3H), 1.28 (s, 3H), 1.12-1.17 (d, 1H, J=14.4 Hz).

Example 54

Preparation of racemic 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]-3-chloro-benzoic acid

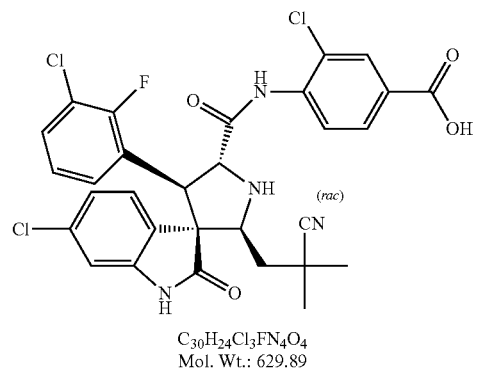 [SMILES: CC(C)(C#N)C[C@@H]1N[C@@H](C(=O)Nc2ccc(C(=O)O)cc2Cl)[C@H](c2cccc(Cl)c2F)[C@]12C(=O)Nc1cc(Cl)ccc12]

To a stirred solution of methyl 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]-3-chloro-benzoate (2.52 g, 4 mmol) in THF (60 mL) was added LiOH (0.38 g in 20 mL water). The mixture was stirred at 40° C. overnight, cooled to rt and treated with 1 N HCl to PH equals 2. The solid was filtered and the cake was dried to give the crude (2.1 g) which was purified by column chromatography to give a white solid. 700 mg, 28% (95% purity by HPLC). $^1$HNMR (DMSO, 400 MHz) δ 10.76 (s, 1H), 10.57 (s, 1H), 8.52-8.54 (d, 1H, J=8.8 Hz), 8.02 (s, 1H), 7.88-7.91 (dd, 1H, J1=8.8 Hz, J2=1.6 Hz), 7.71-7.73 (d, 1H, J=8.0 Hz), 7.59-7.63 (t, 1H, J=7.2 Hz), 7.38-7.41 (t, 1H, J=7.2 Hz), 7.17-7.21 (t, 1H, J=8.0 Hz), 7.06-7.08 (dd, 1H, J1=8.0 Hz, J2=1.6 Hz), 6.71 (s, 1H), 4.81 (s, 1H), 4.62-4.64 (d, 1H, J=9.6 Hz), 4.09 (m, 1H), 3.99-4.00 (m, 1H), 1.70-1.76 (dd, 1H, J1=14.0 Hz, J2=10 Hz), 1.41 (s, 3H), 1.31 (s, 3H), 1.16-1.26 (d, 1H, J=14.0 Hz).

Example 55

Preparation of 4,4,4-trifluoro-3,3-dimethylbutan-1-ol

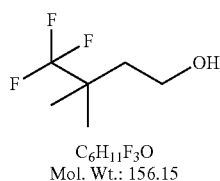

$C_6H_{11}F_3O$
Mol. Wt.: 156.15

To a solution of 4,4,4-trifluoro-3,3-dimethylbutanoic acid (US20100240663; 9.8 g, 58 mmol) in THF (150 mL) under nitrogen was added BH$_3$ (97 mL, 1M in THF, 97 mmol) in a drop-wise manner at 0° C. Then the mixture was stirred at rt for 2 hrs. After completion of reaction that was monitored by TLC (DCM/MeOH=10/1), MeOH was added to quenched the reaction at 10° C. Then the mixture was concentrated. The residue was washed with ethyl acetate and aqueous Na$_2$CO$_3$. The ethyl acetate phase was dried with anhydrous sodium sulfate and concentrated under reduced pressure. Purification by flash chromatography gave crude (2.3 g). $^1$H NMR (400 MHz, CDCl$_3$) δ 3.72 (t, J=7.6 Hz, 2H), 1.97 (br, 1H), 1.75 (t, J=7.6 Hz, 2H), 1.11 (s, 6H).

Example 56

Preparation of 4,4,4-trifluoro-3,3-dimethyl-butanal

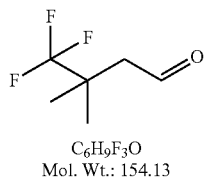

$C_6H_9F_3O$
Mol. Wt.: 154.13

To a stirred solution of oxalyl chloride (2.61 g, 20.56 mmol) in DCM (20 mL) was added DMSO (2.14 g, 27.4 mmol) in DCM (5 mL) slowly at −78° C. The mixture was stirred at −78° C. for 30 min. 4,4,4-Trifluoro-3,3-dimethyl-butan-1-ol (1.07 g, 6.85 mmol) in DCM (5 mL) was added and the mixture was stirred for 1 hr at −78° C. before Et$_3$N (4.16 g, 41.1 mmol) was slowly added. The mixture was gradually warmed to rt over 20 min. and 1N HCl was added. The DCM layer was separated and washed with sat. NaHCO$_3$ and brine, dried with sodium sulfate. The resulting solution was filtered through a short pad of silica gel column eluting with DCM. The collected solution directly used to next step. $^1$HNMR (CDCl$_3$, 300 MHz): δ 9.81-9.82 (t, 1H, J=1.2 Hz), 2.54-2.55 (d, 2H, J=2.4 Hz), 1.29 (s, 6H).

Example 57

Preparation of (E)-methyl 3-methoxy-4-(2-(4,4,4-trifluoro-3,3-dimethylbutylideneamino) acetamido) benzoate

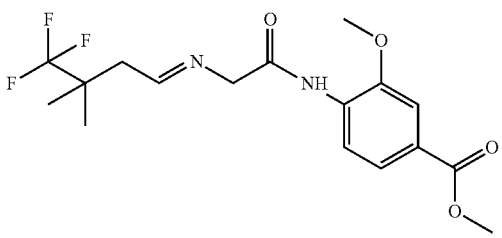

$C_{17}H_{21}F_3N_2O_4$
Mol. Wt.: 374.35

To a stirred suspension of methyl 4-(2-aminoacetamido)-3-methoxybenzoate HCl salt (500 mg, 1.82 mmol) in MTBE (8 mL) was added triethylamine (220 mg, 2.18 mmol). The mixture was stirred for 30 min. at rt and 4,4,4-trifluoro-3,3-dimethyl-butanal (420 mg, 2.73 mmol) was added. The mixture was stirred at rt for 18 hrs. The solid was filtered and washed with MTBE. The filtrate was washed with water and brine, dried with sodium sulfate. Removal of solvent gave a pale yellow solid (0.59 g, 86.8% yield) which was directly used for the next step. $^1$HNMR (CDCl$_3$, 300 MHz): δ 9.42 (s, br, 1H), 8.52-8.55 (d, 1H, J=8.4 Hz), 7.82-7.86 (t, 1H, J=4.8 Hz), 7.73-7.69 (dd, 1H, J1=8.1 Hz, J2=1.5 Hz), 7.57-7.58 (d, 1H, J=1.8 Hz), 4.26 (s, br, 2H), 3.96 (s, 3H), 3.92 (s, 3H), 2.57-2.58 (d, 2H, J=5.1 Hz), 1.26 (s, 6H).

Example 58

Preparation of racemic methyl-4-[[(2'R,3'R,3'S,5'S)-6-chloro-3'(3-chloro-2-fluoro-phenyl)-2-oxo-5'-(3,3,3-trifluoro-2,2-dimethyl-propyl)spiro[indoline-3,4'-pyrrolidine]-2'-carbonyl]amino]-3-methoxy-benzoate

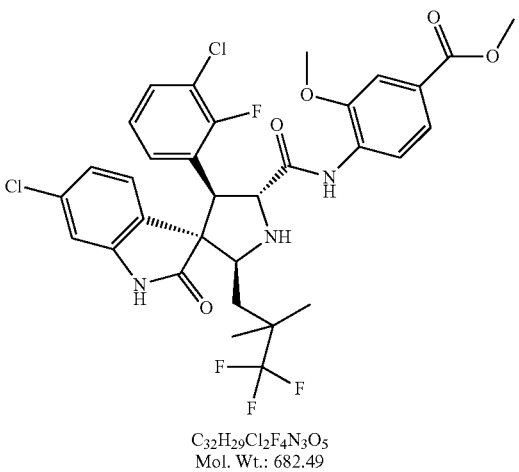 [SMILES: COC(=O)c1ccc(NC(=O)[C@@H]2N[C@@H](CC(C)(C)C(F)(F)F)[C@@]3(C(=O)Nc4cc(Cl)ccc43)[C@H]2c2cccc(Cl)c2F)c(OC)c1]

$C_{32}H_{29}Cl_2F_4N_3O_5$
Mol. Wt.: 682.49

A solution of DBU (Aldrich, 43 mg, 0.29 mmol), (E)-methyl 3-methoxy-4-(2-(4,4,4-trifluoro-3,3-dimethylbutyl-ideneamino)acetamido)benzoate (590 mg, 1.58 mmol) and (E)-3-(3-chloro-2-fluorobenzylidene)-6-chloroindolin-2-one (440 mg, 1.43 mmol) (Shu et al, Org. Process Res. Dev. 2013, 17, 247-256) in toluene (8 mL) was stirred at reflux under nitrogen for 18 hr. The reaction mixture was cooled to rt and then 2 mL of MeOH was added. To the resulting solution was added n-heptane (12 mL) dropwise. The suspension was stirred for an additional 2 h and then filtered. The filter cake was washed with toluene/n-heptane/MeOH (5:5:1) and dried to give product (0.53 g) as an off-white solid. Mother liquid was concentrated. The residue was purified by flash chromatography (35% EOAc in Hexane) to give 0.2 g of product. Total yield is 74.5%. $^1$H NMR (DMSO, 300 MHz): δ 10.68 (s, 1H), 10.53 (s, 1H), 8.39-8.42 (d, 1H, J=8.1 Hz), 7.72-7.75 (d, 1H, J=7.8 Hz), 7.56-7.59 (m, 3H), 7.35-7.40 (t, 1H, J=7.5 Hz), 7.14-7.19 (t, 1H, J=7.8 Hz), 7.02-7.05 (d, 1H, J=8.1 Hz), 6.69 (s, 1H), 4.64-4.70 (t, 1H, J=8.4 Hz), 4.49-4.52 (d, 1H, J=9.3 Hz), 4.00 (s, br, 2H), 3.91 (s, 3H), 3.82 (s, 3H), 1.57 (m, 1H), 1.30 (s, 3H), 1.01 (s, 3H), 0.97-1.01 (d, 1H, J=12.3 Hz).

Example 59

Preparation of racemic 4-[[(2'R,3R,3'S,5'S)-6-chloro-3'-(3-chloro-2-fluoro-phenyl)-2-oxo-5'-[(3,3,3-trifluoro-2,2-dimethyl-propyl)spiro[indoline-3,4'-pyrrolidine]-2'-carbonyl]amino]-3-methoxy-benzoic acid

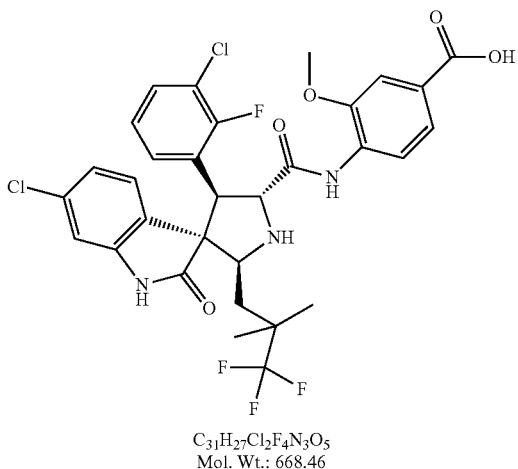 [SMILES: COc1cc(C(=O)O)ccc1NC(=O)[C@@H]1N[C@@H](CC(C)(C)C(F)(F)F)[C@@]2(C(=O)Nc3cc(Cl)ccc32)[C@H]1c1cccc(Cl)c1F]

C$_{31}$H$_{27}$Cl$_2$F$_4$N$_3$O$_5$
Mol. Wt.: 668.46

To a solution of methyl-4-[[(2'R,3'R,3'S,5'S)-6-chloro-3'-(3-chloro-2-fluoro-phenyl)-2-oxo-5'-(3,3,3-trifluoro-2,2-dimethyl-propyl)spiro[indoline-3,4'-pyrrolidine]-2'-carbonyl]amino]-3-methoxy-benzoate (210 mg, 0.31 mmol) in THF (5 mL) and water (1 mL) was added 50% NaOH (1.5 mL). After stirring at 60° C. for 18 hrs under nitrogen, THF was removed by vacuum. The resulting solution was acidified to PH=6 with 55% citric acid. After stirring at rt for 30 min, the solids were filtered, washed with water and dried to give acid (0.21 g, 100.0% Yield)$^1$HNMR (DMSO, 300 MHz): δ 10.74 (s, 1H), 10.55 (s, 1H), 8.25-8.27 (d, 1H, J=8.1 Hz), 7.73-7.75 (d, 1H, J=7.8 Hz), 7.55-7.62 (m, 2H), 7.47-7.49 (d, 1H, J=8.1 Hz), 7.35-7.40 (t, 1H, 7.8 Hz), 7.14-7.20 (t, 1H, J=8.4 Hz), 7.01-7.04 (dd, 1H, J1=7.8 Hz, J2=1.5 Hz), 6.73-6.74 (d, 1H, J=1.5 Hz), 4.65 (s, br, 1H), 4.47-4.50 (d, 1H, J=9.6 Hz), 3.97 (s, br, 2H), 3.87 (s, 3H), 1.57 (m, 1H), 1.32 (s, 3H), 1.02 (s, 3H), 0.97-1.01 (d, 1H, J=12.0 Hz).

Example 60

Preparation of racemic (2'R,3R,3'S,5'S)-N-(4-carbamoyl-2-methoxy-phenyl)-6-chloro-3'-(3-chloro-2-fluoro-phenyl)-2-oxo-5'-(3,3,3-trifluoro-2,2-dimethyl-propyl)spiro[indoline-3,4'-pyrrolidine]-2'-carboxamide

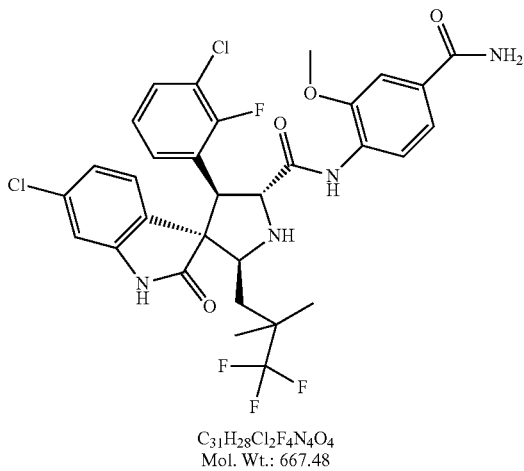 [SMILES: COc1cc(C(N)=O)ccc1NC(=O)[C@@H]1N[C@@H](CC(C)(C)C(F)(F)F)[C@@]2(C(=O)Nc3cc(Cl)ccc32)[C@H]1c1cccc(Cl)c1F]

C$_{31}$H$_{28}$Cl$_2$F$_4$N$_4$O$_4$
Mol. Wt.: 667.48

4-[[(2'R,3R,3'S,5'S)-6-chloro-3'-(3-chloro-2-fluoro-phenyl)-2-oxo-5'-[(2S)-3,3,3-trifluoro-2-methyl-propyl]spiro[indoline-3,4'-pyrrolidine]-2'-carbonyl]amino]-3-methoxy-benzoic acid (210 mg, 0.33 mmol) was dissolved in THF (4 mL). To the stirred solution, CDI (Aldrich, 110 mg, 0.66 mmol) was added and the mixture was stirred for 1 hr at rt. 60 mg of CDI was added and the mixture was stirred for an additional 1 hr. Then ammonia (30%, 2.5 mL) was added and the mixture was stirred for 1 hr. at rt. The mixture was extracted with EtOAc (2×10 mL) and the combined organic phase was washed with 1N HCl, sat. NaHCO$_3$ and brine, dried with sodium sulfate. Chromatography of the residue (85% EtOAc/Hexanes) gave an white solid (0.11 g, 52.4%). $^1$HNMR (DMSO, 300 MHz): δ 10.61 (s, 1H), 10.54 (s, 1H), 8.31-8.34 (d, 1H, J=8.4 Hz), 7.92 (s, br, 1H), 7.74-7.76 (d, 1H, J=8.1 Hz), 7.58-7.63 (m, 2H), 7.49-7.52 (d, 1H, J=8.7 Hz), 7.36-7.41 (t, 1H, 8.1 Hz), 7.28 (s, br, 1H), 7.15-7.21 (t, 1H, J=7.8 Hz), 7.03-7.06 (dd, 1H, J1=7.8 Hz, J2=1.5 Hz), 6.70 (d, 1H, J=1.8 Hz), 4.65-4.70 (t, 1H, J=8.7 Hz), 4.49-4.52 (d, 1H, J=9.9 Hz), 4.00-4.01 (m, 2H), 3.91 (s, 3H), 1.55-1.60 (m, 1H) 1.32 (s, 3H), 1.03 (s, 3H), 0.99-1.03 (d, 1H, J=13.5 Hz).

Example 61

Preparation of (S)-4,4,4-trifluoro-3-methyl-butan-1-ol

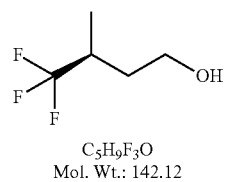

C$_5$H$_9$F$_3$O
Mol. Wt.: 142.12

To a solution of (S)-4-benzyl-3-((S)-4,4,4-trifluoro-3-methylbutanoyl)oxazolidin-2-one (Journal of Fluorine Chemistry, 1999, vol. 97, #1-2 p. 91-96. 27.1 g, 86 mmol) and MeOH (3.3 g, 103 mmol) in $Et_2O$ (780 mL) was added $LiBH_4$ (2.25 g in 10 mL THF) at 0° C. The mixture was stirred at 0° C. for 1 hr then at rt for 1 hr. After completion of reaction by TLC (PE/EA=2/1), NaOH (13.8 g in 150 mL $H_2O$) was added at 0-10° C. The $Et_2O$ phase was separated and the water phase was extracted with $Et_2O$ (200 mL). The combined organic phase was concentrated and the residue was distilled under reduced pressure. The fraction (74° C.-0.096 Mpa) was collected to afford a liquid (10.5 g, Yield 84%). $^1$H NMR (400 MHz, $CDCl_3$) δ 3.60-3.75 (m, 2H), 2.30-2.39 (m, 2H), 1.87-1.96 (m, 1H), 1.44-1.52 (m, 1H), 1.09 (d, J=7.2 Hz, 3H).

Example 62

Preparation of (S)-4,4,4-trifluoro-3-methylbutanal

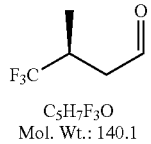

$C_5H_7F_3O$
Mol. Wt.: 140.1

To a stirred solution of oxalyl chloride (3.64 g, 28.7 mmol) in DCM (20 mL) was added DMSO (2.99 g, 38.28 mmol) in DCM (5 mL) slowly at −78° C. The mixture was stirred at −78° C. for 30 min. (S)-4,4,4-Trifluoro-3-methylbutan-1-ol (1.36 g, 9.57 mmol) in DCM (5 mL) was added and the mixture was stirred for 1 hr at −78° C. before $Et_3N$ (5.81 g, 57.42 mmol) was slowly added. The mixture was gradually warmed to rt over 20 min. and 1N HCl was added. The DCM layer was separated and washed with sat. $NaHCO_3$ and brine, dried with sodium sulfate. The resulting solution was filtered through a short pad of silica gel column eluting with DCM. The collected solution directly used to next step. $^1$HNMR ($CDCl_3$, 300 MHz): δ 9.82 (s, 1H), 2.54-2.58 (t, 1H, J=9.0 Hz), 2.21-2.24 (d, 2H, J=9.6 Hz), 1.21-1.23 (d, 3H, J=6.9 Hz).

Example 63

Preparation of (S,E)-methyl 3-methoxy-4-(2-(4,4,4-trifluoro-3-methylbutylideneamino) acetamido)benzoate

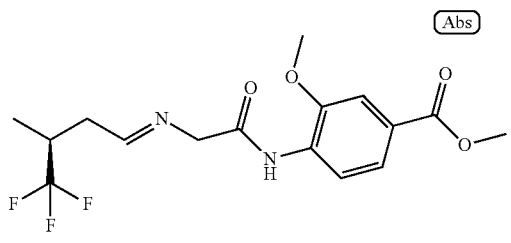

$C_{16}H_{19}F_3N_2O_4$
Mol. Wt.: 360.33

To a stirred suspension of methyl 4-(2-aminoacetamido)-3-methoxybenzoate HCl salt (1.75 g, 6.37 mmol) in MTBE (30 mL) was added triethylamine (0.77 g, 7.64 mmol). The mixture was stirred for 30 min. at rt and (S)-4,4,4-trifluoro-3-methylbutanal (1.61 g, 11.5 mmol) was added. The mixture was stirred at rt for 16 hrs. The reaction mixture was washed with water and brine, dried with sodium sulfate. Removal of solvent gave a pale yellow oil which solidifies upon standing (2.08 g, 90.0% Yield) which was directly used for the next step. $^1$HNMR ($CDCl_3$, 300 MHz): δ 9.50 (s, br, 1H), 8.51-8.54 (d, 1H, J=8.1 Hz), 7.86 (s, br, 1H), 7.68-7.72 (dd, 1H, J1=8.7 Hz, J2=1.8 Hz), 7.55-7.56 (d, 1H, J=1.8 Hz), 4.23 (s, br, 2H), 3.94 (s, 3H), 3.91 (s, 3H), 2.84-2.92 (m, 1H), 2.74-2.79 (m, 1H), 2.35-2.45 (m, 1H), 1.24-1.26 (d, 3H, J=6.9 Hz).

Example 64

Preparation of chiral methyl-4-[[(2'R,3'R,3'S,5'S)-6-chloro-3'(3-chloro-2-fluoro-phenyl)-2-oxo-5'-[(2S)-3,3,3-trifluoro-2-methyl-propyl]spiro[indoline-2,4'-pyrrolidine]-2'-carbonyl]amino]-3-methoxy-benzoate

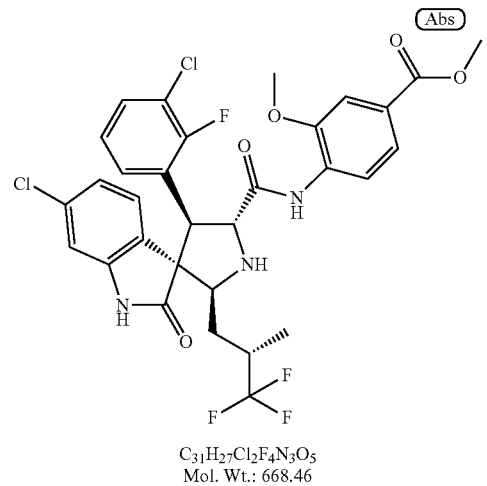 [SMILES: COC(=O)c1ccc(NC(=O)[C@@H]2N[C@@H](C[C@H](C)C(F)(F)F)[C@@]3(C(=O)Nc4cc(Cl)ccc43)[C@H]2c2cccc(Cl)c2F)c(OC)c1]

$C_{31}H_{27}Cl_2F_4N_3O_5$
Mol. Wt.: 668.46

A solution of DBU (Aldrich, 88.0 mg, 0.58 mmol), (S,E)-methyl 3-methoxy-4-(2-(4,4,4-trifluoro-3-methylbutylideneamino)acetamido)benzoate (1.15 g, 3.19 mmol) and (E)-3-(3-chloro-2-fluorobenzylidene)-6-chloroindolin-2-one (0.89 g, 2.88 mmol) (Shu et al, Org. Process Res. Dev. 2013, 17, 247-256) in toluene (10 mL) was stirred at reflux under nitrogen for 18 hr. The reaction mixture was cooled and the solvent was reduced to about 6 mL. Chromatography (40% EtOAc/hexanes) gave two major products. The first component out from the column was the desired isomer (0.88 g, 45.8% Yield). $^1$H NMR (DMSO, 300 MHz): δ 10.70 (s, 1H), 10.56 (s, 1H), 8.38-8.41 (d, 1H, J=8.4 Hz), 7.61-7.66 (m, 3H), 7.30-7.38 (m, 2H), 7.02-7.08 (m, 2H) 6.77 (s, 1H), 4.80-4.86 (t, 1H, J=9.3 Hz), 4.41-4.52 (q, 1H, J=12.3 Hz), 4.31-4.37 (t, 1H, J=9.0 Hz), 3.99 (s, 3H), 3.88 (s, 3H), 3.59-3.67 (m, 1H), 1.37-1.45 (t, 1H, J=11.4 Hz), 1.22-1.27 (t, 1H, J=6.9 Hz), 1.20-1.23 (d, 3H, J=7.2 Hz), 0.86-0.94 (t, 1H, J=11.4 Hz).

The second component from the column was undesired product. (0.97 g, 50.5% Yield). $^1$H NMR (DMSO, 300 MHz): δ 10.65 (s, 1H), 10.56 (s, 1H), 8.38-8.41 (d, 1H, J=8.4

Hz), 7.72-7.75 (d, 1H, J=8.4 Hz), 7.57-7.62 (m, 3H), 7.37-7.42 (t, 1H, 7.2 Hz), 7.16-7.21 (t, 1H, J=8.4 Hz), 7.04-7.07 (d, 1H, J=7.8 Hz), 6.69-6.70 (d, 1H, J=1.8 Hz). 4.63-4.69 (t, 1H, J=9.3 Hz), 4.55-4.58 (d, 1H, J=9.6 Hz), 4.12-4.19 (t, 1H, J=11.7 Hz), 4.01 (s, br., 1H), 3.95 (s, 3H), 3.84 (s, 3H), 1.65-1.72 (t, 1H, J=11.1 Hz), 1.21-1.24 (m, 1H), 1.14-1.16 (d, 3H, J=6.9 Hz), 0.84-0.92 (t, 1H, J=12.3 Hz).

Example 65

Preparation of chiral 4-[[(2'R,3R,3'S,5'S)-6-chloro-3'-(3-chloro-2-fluoro-phenyl)-2-oxo-5'-[(2S)-3,3,3-trifluoro-2-methyl-propyl]spiro[indoline-3,4'-pyrrolidine]-2'-carbonyl]amino]-3-methoxy-benzoic acid

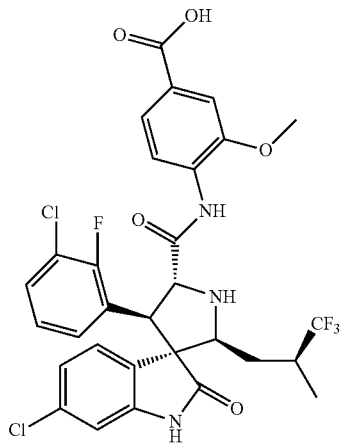

C$_{30}$H$_{25}$Cl$_2$F$_4$N$_3$O$_5$
Mol. Wt.: 654.44

Chiral methyl 4-[[(2'R,3R,3'S,5'S)-6-chloro-3'-(3-chloro-2-fluoro-phenyl)-2-oxo-5'-[(2S)-3,3,3-trifluoro-2-methyl-propyl]spiro[indoline-3,4'-pyrrolidine]-2'-carbonyl]amino]-3-methoxy-benzoate (0.68 g, 1.02 mmol) was dissolved in THF (10 mL) and water (2 mL) was added 50% NaOH (2.5 mL). After stirring at 60° C. for 18 hrs under nitrogen, THF was removed by vacuum. The resulting solution was acidified to PH=6 with 55% citric acid. After stirring at rt for 30 min, the mixture was filtered, and the collected solids were washed with water and dried to give acid (0.67 g, 100.0% Yield) $^1$HNMR (DMSO, 300 MHz): δ 10.58 (s, 1H), 8.30-8.33 (d, 1H, J=8.4 Hz), 7.76-7.79 (d, 1H, J=8.1 Hz), 7.53-7.68 (m, 3H), 7.40-7.45 (t, 1H, 7.5 Hz), 7.19-7.25 (t, 1H, J=8.4 Hz), 7.06-7.10 (dd, 1H, J1=7.8 Hz, J2=1.5 Hz), 6.75 (d, 1H, J=1.8 Hz), 4.66 (s, br, 1H), 4.57-4.60 (d, 1H, J=9.6 Hz), 3.89-4.02 (m, 1H), 3.94 (s, 3H), 3.63 (m, 1H), 1.68-1.79 (m, 1H), 1.23-1.27 (m, 1H), 1.18-1.20 (d, 3H, J=6.6 Hz), 0.87-0.95 (t, 1H, J=11.4 Hz).

Example 66

Preparation of chiral (2'R,3R,3'S,5'S)-N-(4-carbamoyl-2-methoxy-phenyl)-6-chloro-3'-(3-chloro-2-fluoro-phenyl)-2-oxo-5'-[(2S)-3,3,3-trifluoro-2-methyl-propyl]spiro[indoline-3,4'-pyrrolidine]-2'-carboxamide

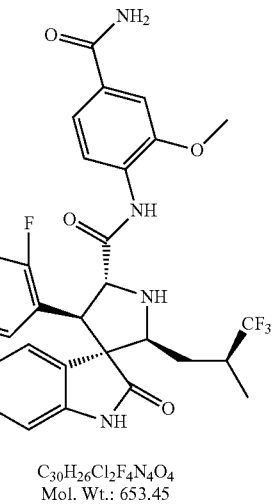

C$_{30}$H$_{26}$Cl$_2$F$_4$N$_4$O$_4$
Mol. Wt.: 653.45

Chiral 4-[[(2'R,3R,3'S,5'S)-6-chloro-3'-(3-chloro-2-fluoro-phenyl)-2-oxo-5'-[(2S)-3,3,3-trifluoro-2-methyl-propyl]spiro[indoline-3,4'-pyrrolidine]-2'-carbonyl]amino]-3-methoxy-benzoic acid (0.21 g, 0.33 mmol) was dissolved in THF (4 mL). To the stirred solution, CDI (Aldrich, 0.11 g, 0.66 mmol) was added and the mixture was stirred for 1 hr at rt. Then ammonia (30%, 2.5 mL) was added and the mixture was stirred for 30 min. at rt. The mixture was extracted with EtOAc (2×10 mL) and the combined organic phase was washed with 1N HCl, sat. NaHCO$_3$ and brine, dried with sodium sulfate. Chromatography of the residue (85% EtOAc/Hexanes) gave an white solid (0.11 g, 51.4%). $^1$HNMR (DMSO, 300 MHz): δ 10.55 (s, 2H), 8.29-8.31 (d, 1H, J=8.1 Hz), 7.93 (s, br, 1H), 7.71-7.75 (d, 1H, J=8.4 Hz), 7.56-7.58 (m, 2H), 7.48-7.51 (dd, 1H, J1=8.4 Hz, J2=1.5 Hz), 7.36-7.41 (t, 1H, 8.4 Hz), 7.36 (s, br, 1H), 7.15-7.21 (t, 1H, J=8.1 Hz), 7.03-7.06 (dd, 1H, J1=8.1 Hz, J2=1.8 Hz), 6.69 (d, 1H, J=1.8 Hz), 4.62-4.64 (m, 1H), 4.53-4.57 (d, 1H, J=9.3 Hz), 4.14 (s, br, 1H), 3.92 (s, 3H), 2.72 (s, br, 1H), 1.64-1.71 (t, 1H, J=10.5 Hz), 1.22 (s, br, 1H), 1.14-1.16 (d, 3H, J=6.9 Hz), 0.84-0.91 (t, 1H, J=11.4 Hz).

Example 67

Preparation of 5,7-dioxa-6-thia-spiro[2.5]octane 6-oxide

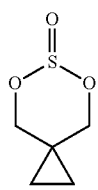

C₅H₈O₃S
Mol. Wt.: 148.18

To a stirred solution of (1-hydroxymethyl-cyclopropyl)-methanol (Combi-blocks, 10.0 g, 97.9 mmol) and triethylamine (22.0 g, 220 mmol) in DCM (120 mL) at −5° C. was added thionyl chloride (13.0 g, 110 mmol) dropwise over 30 min. The resulting suspension was stirred at −5° C. for an additional 2 h and then diluted with water (100 mL). The organic phase was separated, washed with brine, dried over sodium sulfate and filtered. The filtrate was dried under reduced pressure to give 5,7-dioxa-6-thia-spiro[2.5]octane 6-oxide as a white solid (13.5 g, 93%). $^1$HNMR (CDCl$_3$, 300 MHz): δ 5.26-5.30 (d, 2H, J=11.4 Hz), 3.06-3.10 (d, 2H, J=11.7 Hz), 0.84-0.89 (m, 2H), 0.49-0.54 (m, 2H).

Example 68

Preparation of (1-hydroxymethyl-cyclopropyl)-acetonitrile

C₆H₉NO
Mol. Wt.: 111.14

A mixture of 5,7-dioxa-6-thia-spiro[2.5]octane 6-oxide (13.6 g, 92 mmol) and finely powdered sodium cyanide (6.75 g, 138 mmole) in DMSO (30 mL) was stirred at reflux for 18 h. The resulting solution was cooled to room temperature, diluted with ether and washed with water, brine. The organic phase was separated, dried over sodium sulfate and filtered. The filtrate was concentrated to give (1-hydroxymethyl-cyclopropyl)-acetonitrile as a red oil (8.70 g, 85%). $^1$HNMR (CDCl$_3$, 300 MHz): δ 3.59 (s, 2H), 2.62 (s, 2H), 0.66-0.70 (m, 4H).

Example 69

Preparation of methane sulfonic acid 1-cyanomethyl-cyclopropylmethyl ester

C₇H₁₁NO₃S
Mol. Wt.: 189.23

To a stirred solution of (1-hydroxymethyl-cyclopropyl)-acetonitrile (5.1 g, 45.9 mmol) and triethylamine (5.6 g, 55.1 mmol) in DCM (30 mL) at 0° C. was added methane sulfonyl chloride (5.8 g, 50.5 mmol) dropwise over 30 min. The mixture was stirred at 0° C. for 2 h and then diluted with water (50 mL). The organic phase was separated, washed with brine, dried over sodium sulfate and filtered. The filtrate was dried under reduced pressure to give methane sulfonic acid 1-cyanomethyl-cyclopropylmethyl ester (7.2 g, 83%). $^1$HNMR (CDCl$_3$, 300 MHz): δ 4.15 (s, 2H), 3.07 (s, 3H), 2.58 (s, 2H), 0.80-0.82 (m, 4H).

Example 70

Preparation of (1-fluoromethyl-cyclopropyl)-acetonitrile

C₆H₈FN
Mol. Wt.: 113.13

To a stirred solution of methane sulfonic acid 1-cyanomethyl-cyclopropylmethyl ester (6.0 g, 31.7 mmol) in THF (10 mL) was added tetra-n-butylammonium fluoride (1 N in THF, 46.5 mL, 46.5 mmol) dropwise at room temperature over 1 h. After the end of the addition, the resulting solution was held at reflux for 1 h. The mixture was gradually cooled to room temperature over 20 min and then diluted with water (50 mL). The organic layer was separated and dried with sodium sulfate and filtered through a short pad of silica gel column. Removal of solvent (250 mm Hg/rt) gave (1-fluoromethyl-cyclopropyl)-acetonitrile as an oil. The volatile product contained diethyl ether was used in the next step without further evaporation. $^1$HNMR (CDCl$_3$, 300 MHz): δ 4.43 (s, 1H), (s, 1H), 2.64 (s, 2H), 0.80-0.81 (m, 4H).

Example 71

Preparation of (1-fluoromethyl-cyclopropyl)-acetaldehyde

C₆H₉FO
Mol. Wt.: 116.13

To a stirred solution of (1-fluoromethyl-cyclopropyl)-acetonitrile (500 mg, 4.42 mmol) in DCM (10 mL) was added DIBAL (1M in DCM, 4.42 mL, 4.42 mmol) slowly at −78° C. The mixture was stirred at −78° C. for 1.5 h. The reaction mixture was quenched with 5% acetic acid (20 mL) at −78° C. and then warmed to room temperature. The resulting suspension was added saturated ammonium chloride (10 mL) and extracted with DCM. The organic layer was separated, washed with saturated sodium bicarbonate, dried over sodium sulfate and filtered through a short pad of silica gel column. Removal of solvent (275 mm Hg/rt) gave (1-fluoromethyl-cyclopropyl)-acetaldehyde as a colorless oil. The volatile product contained DCM was used in the next step without further evaporation. ¹HNMR (CDCl₃, 300 MHz): δ 9.87 (s, 1H), 4.39 (s, 1H), 4.23 (s, 1H), 2.53 (s, 2H), 0.66-0.75 (m, 4H).

Example 72

Preparation of 4-{2-[(1-fluoromethyl-cyclopropyl methyl ene)-amino]-acetylamino}-3-methoxy-benzoic acid methyl ester

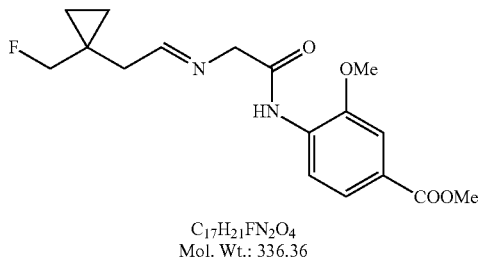 [SMILES: COC(=O)c1ccc(NC(=O)C/N=C/CC2(CF)CC2)c(OC)c1 ; "C17H21FN2O4Mol. Wt.: 336.36"]

C₁₇H₂₁FN₂O₄
Mol. Wt.: 336.36

To a stirred suspension of ethyl 4-(2-aminoacetamido)-3-methoxybenzoate HCl salt (500 mg, 1.82 mmol) in MTBE (10 ML) was added triethylamine (221 mg, 2.18 mmol). The mixture was stirred for 30 min at room temperature and (1-fluoromethyl-cyclopropyl)-acetaldehyde (318 mg, 2.73 mmol) was added. The resulting mixture was stirred at room temperature for 18 hrs. The solid was filtered and washed with MTBE. The filtrate was washed with brine, water and dried with sodium sulfate. Removal of solvent gave an off-white solid 0.55 g which was directly used for the next step. ¹HNMR (CDCl₃, 300 MHz): δ 9.43 (s, 1H), 8.50-8.53 (d, 1H, J=9.0 Hz), 7.87 (s, 1H), 7.66-7.69 (d, 1H, J=9.0 Hz), 7.54 (s, 1H), 4.35 (s, 1H), 4.19-4.21 (m, 3H), 3.88-3.93 (m, 6H), 2.46-2.47 (d, 1H, J=4.8 Hz), 0.62-0.68 (m, 4H).

Example 73

Preparation of racemic 4-{[6-chloro-4'-(3-chloro-2-fluoro-phenyl)-2'-(1-fluoromethyl-cyclopropylmethyl)-2-oxo-1,2-dihydro-spiro[indole-3,3'-pyrrolidin]e-5'-carbonyl]-amino}-3-methoxy-benzoic acid methyl ester

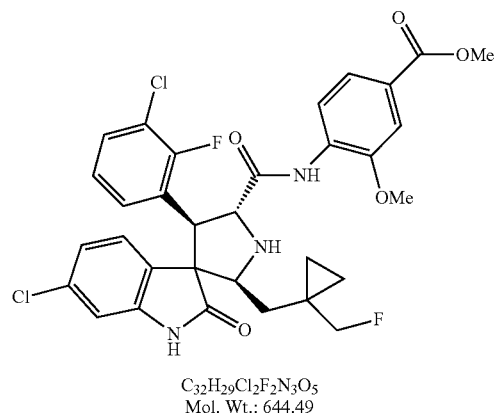 [SMILES: COC(=O)c1ccc(NC(=O)[C@@H]2N[C@@H](CC3(CF)CC3)C3(C(=O)Nc4cc(Cl)ccc43)[C@H]2c2cccc(Cl)c2F)c(OC)c1]

C₃₂H₂₉Cl₂F₂N₃O₅
Mol. Wt.: 644.49

A solution of DBU (Aldrich, 82 mg, 0.54 mmol), 4-{2-[(1-Fluoromethyl-cyclopropylmethylene)-amino]-acety lamino}-3-methoxy-benzoic acid methyl ester (1.00 g, 2.97 mmol) and (E)-3-(3-chloro-2-fluorobenzylidene)-6-chloroindolin-2-one (832 mg, 2.70 mmol) (Shu et al, Org. Process Res. Dev. 2013, 17, 247-256) in toluene (16 mL) was stirred at reflux under nitrogen for 19 hrs. The reaction mixture was cooled and the solvent was reduced to about 6 mL. Chromatography (30% EtOAc/hexanes) gave the desired product (451 mg, 26%). ¹H NMR (DMSO-d₆, 300 MHz): δ 10.70 (s, 1H), 10.50 (s, 1H), 8.41-8.43 (d, 1H, J=8.4 Hz), 7.68-7.71 (d, 1H, J=8.1 Hz), 7.57-7.61 (m, 3H), 7.35-7.40 (t, 1H, 7.2 Hz), 7.14-7.20 (t, 1H, J=8.1 Hz), 7.01-7.05 (dd, 1H, J₁=8.1 Hz, J₂=1.8 Hz), 6.67-6.68 (d, 1H, 1.8 Hz) 4.66-4.72 (t, 1H, J=9.0 Hz), 4.38-4.52 (m, overlapped, 2H), 4.22-4.33 (q, 1H, J₁=42.9 Hz, J₁=24.0 Hz, J₂=9.6 Hz), 3.96 (s, 3H), 3.88-3.91 (covered, 2H), 3.84 (s, 3H), 1.41-1.48 (dd, 1H, J₁=13.8 Hz, J₂=9.0 Hz), 1.05-1.09 (d, 1H, J=13.5 Hz), 0.33-0.65 (m, 4H).

Example 74

Preparation of racemic 4-{[6-chloro-4'-(3-chloro-2-fluoro-phenyl)-2'-(1-fluoromethyl-cyclopropyl methyl)-2-oxo-1,2-dihydro-spiro[indole-3,3'-pyrrolidin]e-5'-carbonyl]-amino}-3-methoxy-benzoic acid

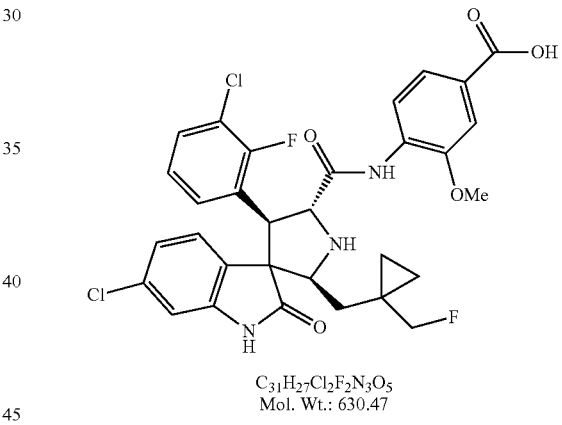

C₃₁H₂₇Cl₂F₂N₃O₅
Mol. Wt.: 630.47

4-{[6-Chloro-4'-(3-chloro-2-fluoro-phenyl)-2'-(1-fluoromethyl-cyclopropylmethyl)-2-oxo-1,2-dihydro-spiro[indole-3,3'-pyrrolidin]e-5'-carbonyl]-amino}-3-methoxy-benzoic acid methyl ester (200 mg, 0.31 mmol) was dissolved in a mixture of THF (10 mL), water (1 mL), and 50% sodium hydroxide solution (1.5 mL). The resulting solution was stirred at 60° C. for 1 d under nitrogen. The reaction mixture was diluted with water (1 mL) and then acidified to pH 6 with 55% citric acid (3 mL). After stirring at room temperature for 30 min, the mixture was filtered, and the collected solids were washed with water (10 mL) and dried to give an off-white solid. (160 mg, 83%) ¹HNMR (DMSO-d₆, 300 MHz): δ 10.68 (s, 1H), 10.50 (s, 1H), 8.38-8.41 (d, 1H, J=8.7 Hz), 7.68-7.71 (d, 1H, J=8.1 Hz), 7.56-7.62 (m, 3H), 7.35-7.40 (t, 1H, J=7.5 Hz), 7.14-7.19 (t, 1H, J=7.8 Hz), 7.01-7.05 (dd, 1H, J₁=7.8 Hz, J₂=1.8 Hz), 6.67-6.68 (d, 1H, J=1.8 Hz), 4.67-4.70 (d, 1H, J=9.6 Hz), 4.38-4.51 (m, overlapped, 2H), 4.22-4.33 (q, 1H, J₁=34.8 Hz, J₂=9.9 Hz) 3.94 (s, 3H), 3.88-3.92 (m, 2H), 1.41-1.49 (m, 1H), 1.04-1.09 (d, 1H, J=14.4 Hz), 0.33-0.63 (m, 4H).

Example 75

Preparation of racemic 6-chloro-4'-(3-chloro-2-fluoro-phenyl)-2'-(1-fluoromethyl-cyclopropyl methyl)-2-oxo-1,2-dihydro-spiro[indole-3,3'-pyrrolidine]-5-carboxylic acid (4-carbamoyl-2-methoxy-phenyl)-amide

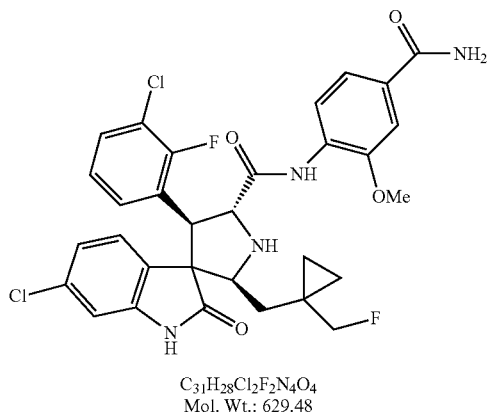 [SMILES: COc1cc(C(N)=O)ccc1NC(=O)[C@@H]1N[C@@H](CC2(CF)CC2)C2(C(=O)Nc3cc(Cl)ccc32)[C@H]1c1cccc(Cl)c1F]

$C_{31}H_{28}Cl_2F_2N_4O_4$
Mol. Wt.: 629.48

4-{[6-Chloro-4'-(3-chloro-2-fluoro-phenyl)-2'-(1-fluoromethyl-cyclopropylmethyl)-2-oxo-1,2-dihydro-spiro[indole-3,3'-pyrrolidin]e-5'-carbonyl]-amino}-3-methoxy-benzoic acid (100 mg, 0.16 mmol) was dissolved in THF (3 mL). To the stirred solution, CDI (Aldrich, 52 mg, 0.32 mmol) was added and the mixture was stirred for 3 h at room temperature. Ammonia hydroxide solution (30%, 2.5 mL) was added and the reaction mixture was stirred for 30 min at room temperature. The resulting suspension was diluted with ethyl acetate and water. The organic phase was separated, washed with brine, saturated $NH_4Cl$ and dried over sodium sulfate. Concentrated to give an off-white solid (90 mg, 90%). $^1$HNMR (DMSO-$d_6$, 300 MHz): δ 10.60 (s, 1H), 10.49 (s, 1H), 8.32-8.35 (d, 1H, J=8.7 Hz), 7.92 (s, br, 1H), 7.68-7.71 (d, 1H, J=7.8 Hz), 7.58-7.62 (m, 2H), 7.49-7.52 (d, 1H, J=8.4 Hz), 7.35-7.40 (t, 1H, 7.5 Hz), 7.29 (s, br, 1H), 7.14-7.19 (t, 1H, J=8.1 Hz), 7.02-7.04 (d, 1H, J=7.8 Hz), 6.68 (s, 1H), 4.65-4.70 (t, 1H, J1=9.0 Hz), 4.38-4.50 (m, overlapped, 2H), 4.22-4.34 (q, 1H, $J_1$=27.3 Hz, $J_2$=9.3 Hz), 3.94 (s, 3H), 3.87 (m, 2H), 1.41-1.49 (m, 1H), 1.04-1.09 (d, 1H, J=13.8 Hz), 0.35-0.62 (m, 4H).

Example 76

Preparation of chiral 4-[[(2'R,3R,3'S,5'S)-6-chloro-3'-(3-chloro-2-fluoro-phenyl)-5'-[[1-(fluoromethyl)cyclopropyl]methyl]-2-oxo-spiro[indoline-3,4'-pyrrolidine]-2'-carbonyl]amino]-3-methoxy-benzoic acid

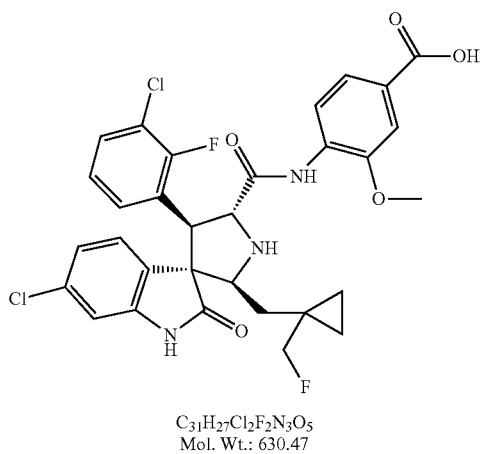 [SMILES: COc1cc(C(=O)O)ccc1NC(=O)[C@@H]1N[C@@H](CC2(CF)CC2)[C@@]2(C(=O)Nc3cc(Cl)ccc32)[C@H]1c1cccc(Cl)c1F]

$C_{31}H_{27}Cl_2F_2N_3O_5$
Mol. Wt.: 630.47

A mixture of (R)—N,N-dimethyl-1-phenylethanamine (0.89 g, 5.96 mmol) and rac-4-[[(2'R,3R,3'S,5'S)-6-chloro-3'-(3-chloro-2-fluoro-phenyl)-5'-[[2-(fluoromethyl)cyclopropyl]methyl]-2-oxo-spiro[indoline-3,4'-pyrrolidine]-2'-carbonyl]amino]-3-methoxy-benzoic acid (2.35 g, 3.73 mmol) in ethyl acetate (40 ml) was stirred at 80° C. for 1 h. The mixture was gradually cooled to room temperature over 4 h and stirred at room temperature for 2 d. The resulting suspension was filtered. The collected solids were washed with cold ethyl acetate and dried to give salt (0.74 g) as a white solid. The mother liquid was concentrated. The residue in ethyl acetate (20 ml) was stirred at 80° C. for 1 h, gradually cooled to 40° C. over 4 h, and stirred at 40° C. overnight. The resulting suspension was filtered. The collected solids were washed with cold ethyl acetate and dried to give the salt (0.20 g) Total weight 0.96 g; yield: 32%. 4-{[6-Chloro-4'-(3-chloro-2-fluoro-phenyl)-2'-(2-fluoromethyl-cyclopropylmethyl)-2-oxo-1,2-dihydro-spiro[indole-3,3'-pyrrolidin]e-5'-carbonyl]-amino}-3-methoxy-benzoic acid To a suspension of 4-{[6-Chloro-4'-(3-chloro-2-fluoro-phenyl)-2'-(2-fluoromethyl-cyclopropylmethyl)-2-oxo-1,2-dihydro-spiro[indole-3,3'-pyrrolidin]e-5'-carbonyl]-amino}-3-methoxy-benzoic acid dimethyl-((R)-1-phenylethyl) amine salt (0.91 g, 1.17 mmol) in ethyl acetate (40 ml) was added 1N HCl solution (7 ml). The mixture was stirred and organic solvent was removed. The solid was filtered and dried to give 4-{[6-Chloro-4'-(3-chloro-2-fluoro-phenyl)-2'-(2-fluoromethyl-cyclopropylmethyl)-2-oxo-1,2-dihydro-spiro[indole-3,3'-pyrrolidin]e-5'-carbonyl]-amino}-3-methoxy-benzoic acid (0.71 g, 96.0% yield, 99% ee) as a white solid. $^1$HNMR (DMSO, 300 MHz): δ 12.83 (br. s, 1H), 10.67 (s, 1H), 10.49 (s, 1H), 8.40-8.37 (d, 1H, J=8.7 Hz), 7.71-7.68 (d, 1H, J=8.4 Hz), 7.62-7.56 (m, 3H), 7.40-7.35 (t, 1H, 7.5 Hz), 7.19-7.16 (t, 1H, J=8.1 Hz), 7.04-7.01 (d, 1H, J1=8.4 Hz), 6.67 (s, 1H), 4.66 (d, br, 1H), 4.51-4.38 (m, overlapped, 2H), 4.33-4.22 (q, 1H, J=9.0 Hz) 3.94 (s, 3H), 3.87 (m, 2H), 1.48-1.40 (m, 1H), 1.09-1.04 (d, 1H, J=14.1 Hz), 0.61-0.34 (m, 4H).

Example 77

Preparation of chiral (2'R,3R,3'S,5'S)-N-(4-carbamoyl-2-methoxy-phenyl)-6-chloro-3'-(3-chloro-2-fluoro-phenyl)-5'-[[1-(fluoromethyl)cyclopropyl]methyl]-2-oxo-spiro[indoline-3,4'-pyrrolidine]-2'-carboxamide

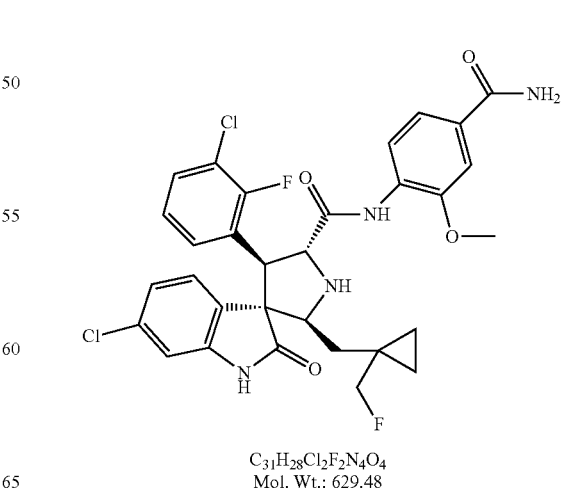

$C_{31}H_{28}Cl_2F_2N_4O_4$
Mol. Wt.: 629.48

4-{[6-Chloro-4'-(3-chloro-2-fluoro-phenyl)-2'-(2-fluoromethyl-cyclopropylmethyl)-2-oxo-1,2-dihydro-spiro[indole-3,3'-pyrrolidin]e-5'-carbonyl]-amino}-3-methoxy-benzoic acid dimethyl-((R)-1-phenylethyl) amine salt (800 mg, 1.03 mmol) was dissolved in THF (6 mL). To the stirred solution, CDI (Aldrich, 330 mg, 2.05 mmol) was added and the mixture was stirred for 2 hr at rt. Then ammonia (30%, 3.0 mL) was added and the mixture was stirred for 0.5 hr. at rt. The mixture was extracted with EtOAc (2×10 mL) and the combined organic phase was washed with 1N HCl, sat. NaHCO$_3$ and brine, dried with sodium sulfate. Chromatography of the residue (EtOAc) gave an white solid (0.64 g, 98.4% yield, 99% ee). $^1$HNMR (DMSO, 300 MHz): δ 10.59 (s, 1H), 10.47 (s, 1H), 8.33-8.30 (d, 1H, J=8.1 Hz), 7.91 (s, br, 1H), 7.69-7.67 (d, 1H, J=7.5 Hz), 7.57 (m, 2H), 7.51-7.48 (d, 1H, J=8.1 Hz), 7.39-7.34 (t, 1H, 7.5 Hz), 7.28 (s, br, 1H), 7.18-7.13 (t, 1H, J=8.4 Hz), 7.03-7.01 (d, 1H, J1=8.1 Hz), 6.66 (s, 1H), 4.66 (s, br, 1H), 4.49-4.46 (d, 1H, J=9.3 Hz), 4.40-4.24 (m, 2H), 3.92 (s, 3H), 3.86 (s, br, 2H), 1.42 (m. 1H) 1.07-1.03 (d, 1H, J=14.1 Hz), 0.61-0.33 (m, 4H).

Example 78

MDM2-p53 TR-FRET Binding Assays

Test compounds (12.34 uM stock in DMSO) were diluted three fold in series in DMSO and 2 ul per well were added into 384-well polypropylene plates (Matrix) in triplicates. GST-tag full length MDM2 (22 nM, 30.8 ul/well) in Assay Buffer (50 mM Tris-HCl, pH 7.4, 100 mM NaCl, 1 mM DTT and 0.2 mg/ml BSA) were added followed by 5 ul per well of 72 nM biotin p53 peptide (Biotin-Aca-SQETFSDL-WKLLPEN-OH) in Assay Buffer. The samples were incubated at room temperature for 30 min, and 2.5 ul per well of detection solution containing 16 nM europium (Eu) conjugated streptavidin (PerkinElmer) and 200 nM allophycocyanin (APC) conjugated anti-GST antibody (Columbia Biosciences) in Assay Buffer (without DTT) were added. The samples were incubated at room temperature for 40 min. Assay signals were monitored by reading excitation at 340 nm and emission fluorescence at 615 nm and 665 nm on an Envision reader. IC$_{50}$ values were calculated using Prism software (GraphPad). Examples are listed in the following.

| Example Number | TR-FRET (IC$_{50}$ nM) |
| --- | --- |
| 10 | IC$_{50}$ ≤ 7.2 |
| 11 | IC$_{50}$ ≤ 7.2 |
| 12 | IC$_{50}$ ≤ 7.2 |
| 13 | IC$_{50}$ ≤ 7.2 |
| 19 | IC$_{50}$ ≤ 3.6 |
| 20 | IC$_{50}$ ≤ 3.6 |
| 21 | IC$_{50}$ ≤ 3.6 |
| 22 | IC$_{50}$ ≤ 3.6 |
| 26 | IC$_{50}$ ≤ 7.2 |
| 27 | IC$_{50}$ ≤ 3.6 |
| 28 | IC$_{50}$ ≤ 3.6 |
| 65 | IC$_{50}$ ≤ 3.6 |
| 66 | IC$_{50}$ ≤ 3.6 |
| 73 | IC$_{50}$ ≤ 7.2 |
| 74 | IC$_{50}$ ≤ 7.2 |
| 75 | IC$_{50}$ ≤ 7.2 |
| 76 | IC$_{50}$ ≤ 7.2 |
| 77 | IC$_{50}$ ≤ 7.2 |

Example 79

Cellular data of selected compounds against SW480 and SJSA-1 was conducted according to the following protocol.

1. Methods:
1) Sources of the Used Cancer Cell Lines:

| Cell lines | Tissues | Sources | Culture medium |
| --- | --- | --- | --- |
| SW-480 | human colorectal cancer | West China University of Medical Sciences | L-15 + glutamine + 10% fetal bovine serum |
| SJSA-1 | human osteosarcoma | ATCC | RPMI1640 + HEPES + 10% fetal bovine serum |

2) Experimental Procedure:

Cells in the logarithmic growth phase were seeded into 96-well plates (Corning, 3599; 180 μL/well; 3000 cells/well for both SW480 and SJSA-1 cell lines) and cultured in an incubator (Thermo, 3111) for 24 h. Cells were then treated in triplicate by adding 20 μL/well solution containing different concentrations of the tested compounds in 5% CO2 at 37° C. for 5 days. After that, cells were treated for additional 4 h by adding 10 μL/well Cell Counting Kit-8 (CCK-8; DojinDo, CK04) solution. Finally, the absorbance was read at 450 nm with a microplate reader spectra-MAX190 (Molecular Devices, Sunnyvale, Calif.). The IC$_{50}$ value was determined with SofeMax Pro, a software equipped in this reader. The cell proliferation inhibition rate was calculated as: proliferation inhibition (%)=[1-(A450 treated/A450 control)]×100%.

2. Dissolution of the Tested Compounds:

All the tested compounds could be dissolved in DMSO at 10$^{-2}$ M (as stock solution). All compounds except Reference compound were dissolved well after being diluted in culture medium to 10$^{-4}$ M. Reference compound was in a suspension state after being diluted in medium to 10$^{-4}$ M and even being ultra-sonicated at 60° C. for 30 min but in a solution state at 33.33 μM. The compounds were diluted at 9 3-fold serial concentrations beginning at the initial concentration of 10 μM (i.e., the highest final concentration to treat the cells). The detailed drug dilution protocol is: Add 5 μL stock solution (10$^{-2}$ M) into 495 μL medium, transfer 125 μL of the resulting solution (100 μM) into 250 μL medium, and repeat this till the 9$^{th}$ resulting concentration of 15.2 nM. Pipet 20 μL of each drug dilution into cell plates.

| Example Number | IC$_{50}$ (nM) (SJSA-1) |
| --- | --- |
| 9a | 71 ≤ IC$_{50}$ ≤ 2500 |
| 9b | 71 ≤ IC$_{50}$ ≤ 550 |
| 10 | IC$_{50}$ ≤ 71.0 |
| 11 | IC$_{50}$ ≤ 71.0 |
| 12 | IC$_{50}$ ≤ 71.0 |
| 13 | IC$_{50}$ ≤ 71.0 |
| 19 | IC$_{50}$ ≤ 71.0 |
| 20 | IC$_{50}$ ≤ 71.0 |
| 21 | IC$_{50}$ ≤ 20.0 |
| 22 | IC$_{50}$ ≤ 20.0 |
| 26 | IC$_{50}$ ≤ 500 |
| 27 | IC$_{50}$ ≤ 20.0 |
| 28 | IC$_{50}$ ≤ 20.0 |
| 65 | IC$_{50}$ ≤ 20.0 |
| 66 | IC$_{50}$ ≤ 20.0 |
| 74 | IC$_{50}$ ≤ 20.0 |
| 75 | IC$_{50}$ ≤ 20.0 |
| 76 | IC$_{50}$ ≤ 20.0 |
| 77 | IC$_{50}$ ≤ 20.0 |

This invention described herein is of spiropyrrolidine compounds and methods of making the same. Although some embodiments have been discussed above, other implementations and applications are also within the scope of the following claims. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

What is claimed:

1. A compound of formula I, or a pharmaceutically acceptable salt thereof:

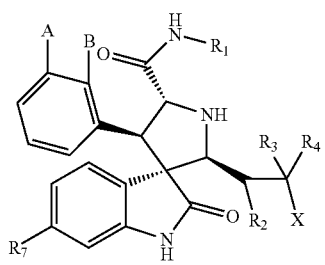

I wherein A are halogens and are independently selected from Cl and F and B are independently selected from Cl, H and F;

$R_1$ is aryl, substituted aryl, heteroaryl and substituted heteroaryl;

$R_2$ is hydrogen or it is a carbon-carbon bond with either X, $R_3$ or $R_4$;

$R_3$ and $R_4$ are independently selected from H, lower alkyl and substituted lower alkyls, cycloalkyls, substituted cycloalkyls, alkenyls, substituted alkenyls, alkyns, substituted alkyns, or they together can form a 3, 4, or 5 membered ring or one of them can form a C—C bond with $R_2$;

X is independently selected from F, CN, and

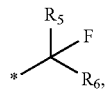

where $R_5$ and $R_6$ are independently selected from hydrogen and F; and $R_7$ is halogen and is selected independently from Cl, Br and F.

2. A compound of claim 1, or a pharmaceutically acceptable salt thereof, wherein
$R_2$ is H; $R_3$ and $R_4$ are both methyl; and X is CN.

3. A compound of claim 1, or a pharmaceutically acceptable salt thereof, wherein
$R_2$ forms a C—C bond with X; and $R_3$ and $R_4$ are independently selected from methyl, lower alkyl, substituted lower alkyl, alkenyl and substituted lower alkenyl, or they together can form a 3, 4, or 5 membered aliphatic ring.

4. A compound of claim 1, or a pharmaceutically acceptable salt thereof, which conform to formula II:

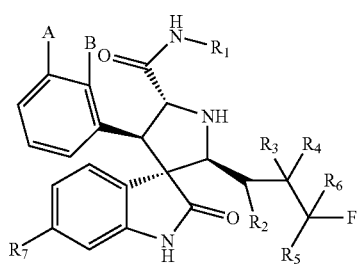

II wherein $R_5$ and $R_6$ are independently selected from hydrogen and F.

5. A compound of claim 4, or a pharmaceutically acceptable salt thereof, wherein $R_2$ is hydrogen; and $R_5$ and $R_6$ are both H.

6. A compound of claim 4, or a pharmaceutically acceptable salt thereof, wherein $R_2$ is hydrogen; $R_3$ and $R_4$ are both methyl; and $R_5$ and $R_6$ are both H.

7. A compound of claim 4, or a pharmaceutically acceptable salt thereof, wherein $R_2$ is H; $R_3$ and $R_4$ together form a 3, 4, or 5 membered aliphatic ring, such as a cyclopropyl ring; and $R_5$ and $R_6$ are both H.

8. A compound of claim 1, or a pharmaceutically acceptable salt thereof, which conform to formula III:

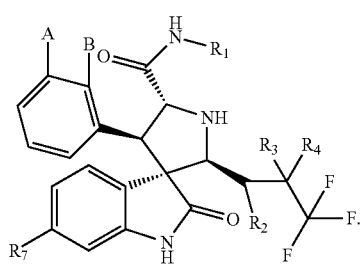

(III)

9. A compound of claim 1, or a pharmaceutically acceptable salt thereof, which conform to formula IV:

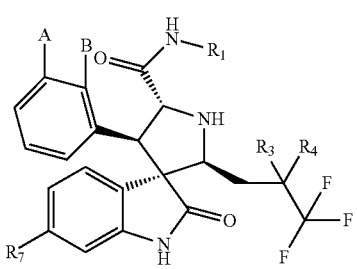

IV

A is independently selected from Cl, F, and Br; B is selected from F, H; and $R_3$ and $R_4$ are independently selected from H, and methyl.

10. A compound of claim 1, or a pharmaceutically acceptable salt thereof, wherein $R_1$ is, but not limited to, one of the following:

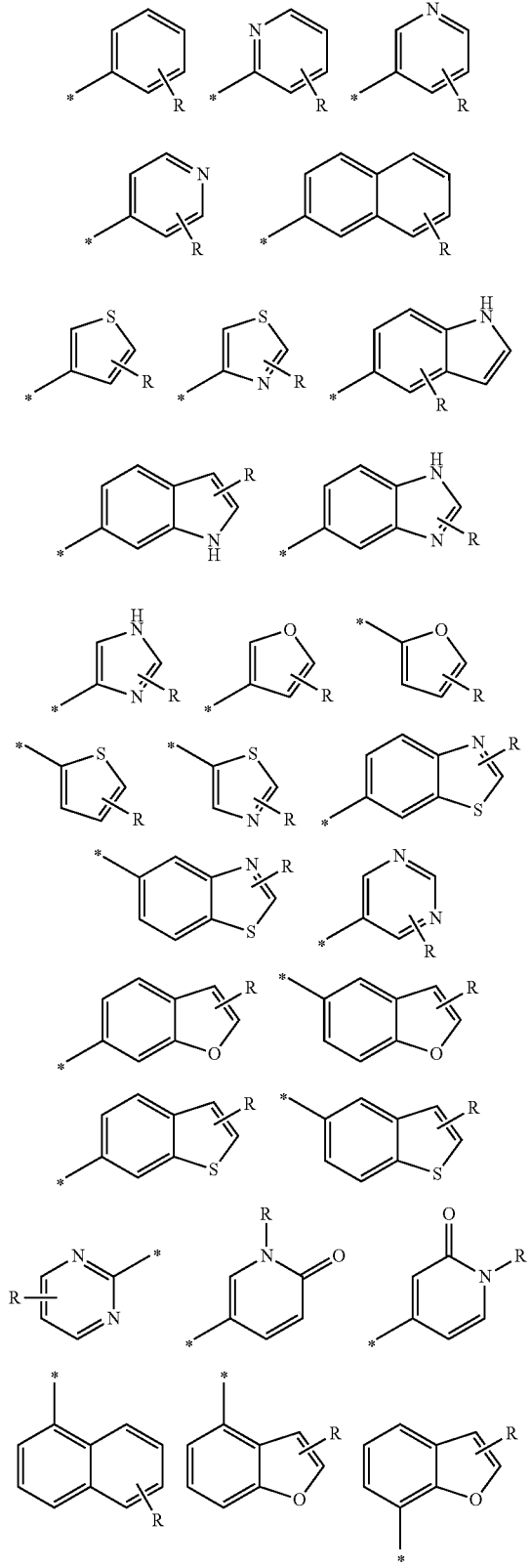

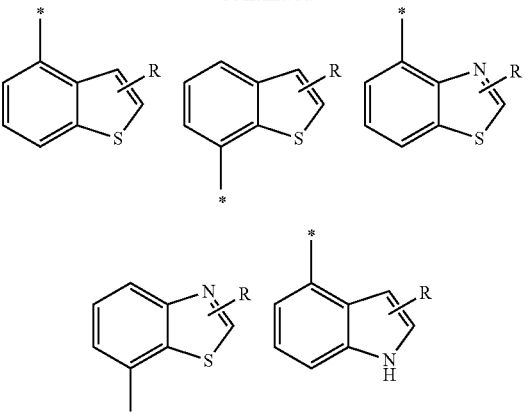

-continued

Where R is independently selected from groups of halogen, hydroxyl, hydrogen, lower alkyl, substituted lower alkyl, cycloalkyl, substituted cycloalkyl, lower alkoxy, substituted lower alkoxy, cyano, amino, substituted amino, substituted sulfonylamino, aminosulfonyl, substituted aminosulfonyl, hydroxycarbonyl, lower alkoxycarbonyl, aminocarbonyl, substituted aminocarbonyl, substituted carbonylamino, amidino, substituted amidino, guanidino, substituted guanidino, tetrazoles, substituted tetrazoles and can independently substitute any single position or multiple positions of the aryl/hetero aryl ring and preferably not to exceed three positions; Or when the substitution occurs at two adjacent positions, it can form a five or six membered hetero ring.

11. A compound of claim 10, or a pharmaceutically acceptable salt thereof, wherein $R_1$ is one of the following:

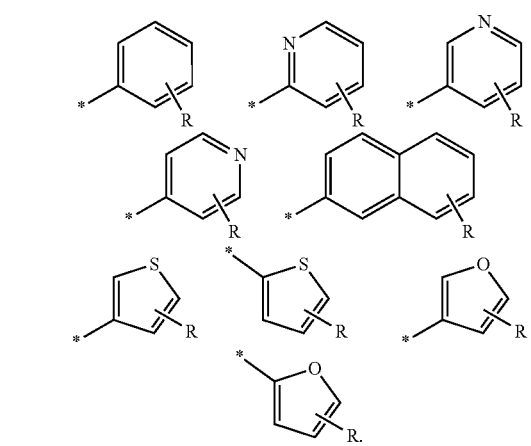

12. A compound of claim 10, or a pharmaceutically acceptable salt thereof, wherein $R_1$ is one of the following:

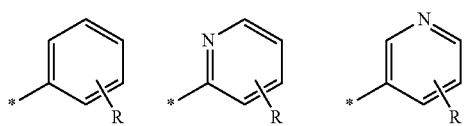

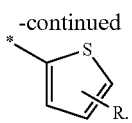

13. A compound of claim 10, or a pharmaceutically acceptable salt thereof, wherein R is independently selected from groups of halogen, lower alkyl, substituted lower alkyl, lower alkoxy, substituted lower alkoxy, cyano, aminosulfonyl, substituted aminosulfonyl, hydroxycarbonyl, lower alkoxycarbonyl, aminocarbonyl, substituted aminocarbonyl, and can independently substitute multiple positions of the aryl/heteroaryl ring; Where R is independently selected from groups of halogen, hydroxyl, hydrogen, lower alkyl, substituted lower alkyl, cycloalkyl, substituted cycloalkyl, lower alkoxy, substituted lower alkoxy, cyano, amino, substituted amino, substituted sulfonylamino, aminosulfonyl, substituted aminosulfonyl, hydroxycarbonyl, lower alkoxycarbonyl, aminocarbonyl, substituted aminocarbonyl, substituted carbonylamino, amidino, substituted amidino, guanidino, substituted guanidino, tetrazoles, substituted tetrazoles and can independently substitute any single position or multiple positions of the aryl/heteroaryl ring and preferably not to exceed three positions; Or when the substitution occurs at two adjacent positions, it can form a five or six membered hetero ring.

14. A compound of claim 1, or a pharmaceutically acceptable salt thereof, which is:

Racemic ethyl 4-[[(2'R,3R,3'S,5'S)-6-chloro-3'-(3-chloro-2-fluoro-phenyl)-5'-(2-methylprop-1-enyl)-2-oxo-spiro[indoline-3,4'-pyrrolidine]-2'-carbonyl]amino]-3-methoxy-benzoate;

Racemic 4-[[(2'R,3R,3'S,5'S)-6-chloro-3'-(3-chloro-2-fluoro-phenyl)-5'-(2-methylprop-1-enyl)-2-oxo-spiro[indoline-3,4'-pyrrolidine]-2'-carbonyl]amino]-3-methoxy-benzoic acid;

Racemic (2'R,3R,3'S,5'S)-N-(4-carbamoyl-2-methoxy-phenyl)-6-chloro-3'-(3-chloro-2-fluoro-phenyl)-5'-(2-methylprop-1-enyl)-2-oxo-spiro[indoline-3,4'-pyrrolidine]-2'-carboxamide;

Racemic ethyl 4-[[(2'R,3R,3'S,5'S)-6-chloro-3'-(3-chloro-2-fluoro-phenyl)-2-oxo-5'-[(2R)-3,3,3-trifluoro-2-methyl-propyl]spiro[indoline-3,4'-pyrrolidine]-2'-carbonyl]amino]-3-methoxy-benzoate;

Racemic 4-[[(2'R,3R,3'S,5'S)-6-chloro-3'-(3-chloro-2-fluoro-phenyl)-2-oxo-5'-[(2S)-3,3,3-trifluoro-2-methyl-propyl]spiro[indoline-3,4'-pyrrolidine]-2'-carbonyl]amino]-3-methoxy-benzoic acid;

Racemic 4-[[(2'R,3R,3'S,5'S)-6-chloro-3'-(3-chloro-2-fluoro-phenyl)-2-oxo-5'-[(2R)-3,3,3-trifluoro-2-methyl-propyl]spiro[indoline-3,4'-pyrrolidine]-2'-carbonyl]amino]-3-methoxy-benzoic acid;

Racemic (2'R,3R,3'S,5'S)-N-(4-carbamoyl-2-methoxy-phenyl)-6-chloro-3'-(3-chloro-2-fluoro-phenyl)-2-oxo-5'-[(2S)-3,3,3-trifluoro-2-methyl-propyl]spiro[indoline-3,4'-pyrrolidine]-2'-carboxamide;

Racemic (2'R,3R,3'S,5'S)-N-(4-carbamoyl-2-methoxy-phenyl)-6-chloro-3'-(3-chloro-2-fluoro-phenyl)-2-oxo-5'-[(2R)-3,3,3-trifluoro-2-methyl-propyl]spiro[indoline-3,4'-pyrrolidine]-2'-carboxamide;

Racemic (4-ethoxycarbonyl-2-methoxy-phenyl) (2'R,3R,3'S,5'S)-6-chloro-3'-(3-chloro-2-fluoro-phenyl)-5'-(3-fluoro-2,2-dimethyl-propyl)-2-oxo-spiro[indoline-3,4'-pyrrolidine]-2'-carboxamide;

Racemic 4-[(2'R,3R,3'S,5'S)-6-chloro-3'-(3-chloro-2-fluoro-phenyl)-5'-(3-fluoro-2,2-dimethyl-propyl)-2-oxo-spiro[indoline-3,4'-pyrrolidine]-2'-carbonyl]amino-3-methoxy-benzoic acid;

Racemic (4-carbamoyl-2-methoxy-phenyl) (2'R,3R,3'S,5'S)-6-chloro-3'-(3-chloro-2-fluoro-phenyl)-5'-(3-fluoro-2,2-dimethyl-propyl)-2-oxo-spiro[indoline-3,4'-pyrrolidine]-2'-carboxamide;

Chiral 4-[(2'R,3R,3'S,5'S)-6-chloro-3'-(3-chloro-2-fluoro-phenyl)-5'-(3-fluoro-2,2-dimethyl-propyl)-2-oxo-spiro[indoline-3,4'-pyrrolidine]-2'-carbonyl]-3-methoxy-benzoic acid;

Chiral (4-carbamoyl-2-methoxy-phenyl) (2'R,3R,3'S,5'S)-6-chloro-3'-(3-chloro-2-fluoro-phenyl)-5'-(3-fluoro-2,2-dimethyl-propyl)-2-oxo-spiro[indoline-3,4'-pyrrolidine]-2'-carboxamide;

Chiral ethyl-4-[[(2'R,3'R,3'S,5'S)-6-chloro-3'(3-chloro-2-fluoro-phenyl)-2-oxo-5'-[(2R)-3,3,3-trifluoro-2-methyl-propyl]spiro[indoline-2,4'-pyrrolidine]-2'-carbonyl]amino]-3-methoxy-benzoate;

Chiral 4-[[(2'R,3R,3'S,5'S)-6-chloro-3'-(3-chloro-2-fluoro-phenyl)-2-oxo-5'-[(2R)-3,3,3-trifluoro-2-methyl-propyl]spiro[indoline-3,4'-pyrrolidine]-2'-carbonyl]amino]-3-methoxy-benzoic acid;

Chiral (2'R,3R,3'S,5'S)-N-(4-carbamoyl-2-methoxy-phenyl)-6-chloro-3'-(3-chloro-2-fluoro-phenyl)-2-oxo-5'-[(2R)-3,3,3-trifluoro-2-methyl-propyl]spiro[indoline-3,4'-pyrrolidine]-2'-carboxamide;

Racemic tert-butyl (2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carboxylate;

Racemic (2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carboxylic acid;

Racemic methyl 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]benzoate;

Racemic 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]benzoic acid;

Racemic (2'R,3R,3'S,5'S)-N-(4-carbamoylphenyl)-6-chloro-3'-(3-chloro-2-fluoro-phenyl)-5'-(2-cyano-2-methyl-propyl)-2-oxo-spiro[indoline-3,4'-pyrrolidine]-2'-carboxamide;

Racemic (2'R,3R,3'S,5'S)-6-chloro-3'-(3-chloro-2-fluoro-phenyl)-5'-(2-cyano-2-methyl-propyl)-N-[4-(2-hydroxyethoxy)phenyl]-2-oxo-spiro[indoline-3,4'-pyrrolidine]-2'-carboxamide;

Racemic methyl 5-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]thiophene-2-carboxylate;

Racemic 5-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]thiophene-2-carboxylic acid;

Racemic (2'R,3R,3'S,5'S)-N-(5-carbamoyl-2-thienyl)-6-chloro-3'-(3-chloro-2-fluoro-phenyl)-5'-(2-cyano-2-methyl-propyl)-2-oxo-spiro[indoline-3,4'-pyrrolidine]-2'-carboxamide;

Racemic methyl 5-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]pyridine-2-carboxylate;

Racemic 5-[[(2'R,3R,3'S,5'S)-6-chloro-3'-(3-chloro-2-fluoro-phenyl)-5'-(2-cyano-2-methyl-propyl)-2-oxospiro[indoline-3,4'-pyrrolidine]-2'-carbonyl]amino]
pyridine-2-carboxylic acid;

Racemic methyl 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]-3-methoxy-benzoate;

Racemic 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]-3-methoxy-benzoic acid;

Racemic (2'R,3R,3'S,5'S)-N-(4-carbamoyl-2-methoxy-phenyl)-6-chloro-3'-(3-chloro-2-fluoro-phenyl)-5'-(2-cyano-2-methyl-propyl)-2-oxo-spiro[indoline-3,4'-pyrrolidine]-2'-carboxamide;

Chiral 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]-3-methoxy-benzoic acid Racemic methyl 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]-3-fluoro-benzoate;

Racemic 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]-3-fluoro-benzoic acid;

Racemic methyl 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]-3-fluoro-benzoate;

Racemic 4-[[(2'R,3R,3'S,5'S)-6-chloro-3'-(3-chloro-2-fluoro-phenyl)-5'-(2-cyano-2-methyl-propyl)-2-oxo-spiro[indoline-3,4'-pyrrolidine]-2'-carbonyl]amino]-3-chloro-benzoic acid;

Racemic methyl-4-[[(2'R,3'R,3'S,5'S)-6-chloro-3'(3-chloro-2-fluoro-phenyl)-2-oxo-5'-(3,3,3-trifluoro-2,2-dimethyl-propyl)spiro[indoline-3,4'-pyrrolidine]-2'-carbonyl]amino]-3-methoxy-benzoate;

Racemic 4-[[(2'R,3R,3'S,5'S)-6-chloro-3'-(3-chloro-2-fluoro-phenyl)-2-oxo-5'-[(3,3,3-trifluoro-2,2-dimethyl-propyl)spiro[indoline-3,4'-pyrrolidine]-2'-carbonyl]amino]-3-methoxy-benzoic acid;

Racemic (2'R,3R,3'S,5'S)-N-(4-carbamoyl-2-methoxy-phenyl)-6-chloro-3'-(3-chloro-2-fluoro-phenyl)-2-oxo-5'-(3,3,3-trifluoro-2,2-dimethyl-propyl)spiro[indoline-3,4'-pyrrolidine]-2'-carboxamide;

Chiral methyl-4-[[(2'R,3'R,3'S,5'S)-6-chloro-3'(3-chloro-2-fluoro-phenyl)-2-oxo-5'-[(2S)-3,3,3-trifluoro-2-methyl-propyl]spiro[indoline-2,4'-pyrrolidine]-2'-carbonyl]amino]-3-methoxy-benzoate;

Chiral 4-[[(2'R,3R,3'S,5'S)-6-chloro-3'-(3-chloro-2-fluoro-phenyl)-2-oxo-5'-[(2S)-3,3,3-trifluoro-2-methyl-propyl]spiro[indoline-3,4'-pyrrolidine]-2'-carbonyl]amino]-3-methoxy-benzoic acid;

Chiral (2'R,3R,3'S,5'S)-N-(4-carbamoyl-2-methoxy-phenyl)-6-chloro-3'-(3-chloro-2-fluoro-phenyl)-2-oxo-5'-[(2S)-3,3,3-trifluoro-2-methyl-propyl]spiro[indoline-3,4'-pyrrolidine]-2'-carboxamide;

Racemic 4-{[6-chloro-4'-(3-chloro-2-fluoro-phenyl)-2'-(1-fluoromethyl-cyclopropylmethyl)-2-oxo-1,2-dihydro-spiro[indole-3,3'-pyrrolidin]e-5'-carbonyl]-amino}-3-methoxy-benzoic acid methyl ester;

Racemic 4-{[6-chloro-4'-(3-chloro-2-fluoro-phenyl)-2'-(1-fluoromethyl-cyclopropylmethyl)-2-oxo-1,2-dihydro-spiro[indole-3,3'-pyrrolidin]e-5'-carbonyl]-amino}-3-methoxy-benzoic acid;

Racemic 6-chloro-4'-(3-chloro-2-fluoro-phenyl)-2'-(1-fluoromethyl-cyclopropyl methyl)-2-oxo-1,2-dihydro-spiro[indole-3,3'-pyrrolidine]-5'-carboxylic acid (4-carbamoyl-2-methoxy-phenyl)-amide;

Chiral 4-[[(2'R,3R,3'S,5'S)-6-chloro-3'-(3-chloro-2-fluoro-phenyl)-5'-[[1(fluoromethyl)cyclopropyl]methyl]-2-oxo-spiro[indoline-3,4'-pyrrolidine]-2'-carbonyl]amino]-3-methoxy-benzoic acid; or Chiral (2'R, 3R,3'S,5'S)-N-(4-carbamoyl-2-methoxy-phenyl)-6-chloro-3'-(3-chloro-2-fluoro-phenyl)-5'-[[1-(fluoromethyl)cyclopropyl]methyl]-2-oxo-spiro[indoline-3,4'-pyrrolidine]-2'-carboxamide.

15. A pharmaceutical composition, comprising a compound of claim 1, and a pharmaceutically acceptable salt, pro-drug or excipient.

16. A method of treating a proliferative disorder characterized by over expression of MDM2 comprising administering to a subject an effective amount of a compound of claim 1, or a pharmaceutically acceptable salt thereof, wherein the proliferative disorder is breast, colon, colorectal, leukemia, melanoma, neuroblastoma, pancreatic, prostate, kidney, breast, osteosarcoma or lung cancer.

17. A compound of claim 6, or a pharmaceutically acceptable salt thereof, wherein $R_1$ is:

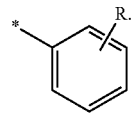

18. A compound of claim 7 or a pharmaceutically acceptable salt thereof, wherein $R_1$ is:

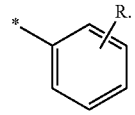

19. A compound of claim 9 or a pharmaceutically acceptable salt thereof, wherein $R_1$ is:

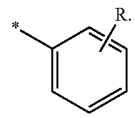

20. A method of inhibiting MDM2 comprising administering to a subject in need thereof an effective amount of a compound of claim 1 or a pharmaceutically acceptable salt thereof.

* * * * *